(12) United States Patent
Emanuele et al.

(10) Patent No.: US 9,757,411 B2
(45) Date of Patent: Sep. 12, 2017

(54) POLOXAMER THERAPY FOR HEART FAILURE

(71) Applicant: Mast Therapeutics, Inc., San Diego, CA (US)

(72) Inventors: R. Martin Emanuele, San Diego, CA (US); Santosh Vetticaden, San Diego, CA (US); Patrick Keran, Cardiff, CA (US)

(73) Assignee: Aires Pharmaceuticals, Inc., Austin, TX (US)

( * ) Notice: Subject to any disclaimer, the term of this patent is extended or adjusted under 35 U.S.C. 154(b) by 0 days.

(21) Appl. No.: 14/793,662

(22) Filed: Jul. 7, 2015

(65) Prior Publication Data

US 2016/0000822 A1   Jan. 7, 2016

Related U.S. Application Data

(63) Continuation-in-part of application No. PCT/US2014/045627, filed on Jul. 7, 2014.

(60) Provisional application No. 62/126,400, filed on Feb. 27, 2015, provisional application No. 62/021,691, filed on Jul. 7, 2014.

(51) Int. Cl.
| | |
|---|---|
| A61F 2/00 | (2006.01) |
| A61K 31/765 | (2006.01) |
| A61K 45/06 | (2006.01) |
| A61K 9/00 | (2006.01) |

(52) U.S. Cl.
CPC ............ *A61K 31/765* (2013.01); *A61K 45/06* (2013.01); *A61K 9/0024* (2013.01)

(58) Field of Classification Search
None
See application file for complete search history.

(56) References Cited

U.S. PATENT DOCUMENTS

| | | | |
|---|---|---|---|
| 4,522,811 A | 6/1985 | Eppstein et al. | 514/2 |
| 4,801,452 A | 1/1989 | Hunter | 424/94.63 |
| 4,837,014 A | 6/1989 | Hunter et al. | 424/78 |
| 4,873,083 A | 10/1989 | Hunter et al. | 424/83 |
| 4,879,109 A | 11/1989 | Hunter | 424/83 |
| 4,897,263 A | 1/1990 | Hunter | 424/83 |
| 4,937,070 A | 6/1990 | Hunter | 424/83 |
| 4,997,644 A | 3/1991 | Hunter | 424/83 |
| 5,017,370 A | 5/1991 | Hunter | 424/83 |
| 5,028,599 A | 7/1991 | Hunter | 424/83 |
| 5,030,448 A | 7/1991 | Hunter | 514/83 |
| 5,032,394 A | 7/1991 | Hunter | 424/83 |
| 5,039,520 A | 8/1991 | Hunter | 424/83 |
| 5,041,288 A | 8/1991 | Hunter | 424/83 |
| 5,047,236 A | 9/1991 | Hunter | 424/83 |
| 5,064,643 A | 11/1991 | Hunter | 424/83 |
| 5,071,649 A | 12/1991 | Hunter | 424/83 |
| 5,078,995 A | 1/1992 | Hunter | 424/83 |
| 5,080,894 A | 1/1992 | Hunter | 424/83 |
| 5,089,260 A | 2/1992 | Hunter | 424/83 |
| 5,523,492 A | 6/1996 | Emanuele et al. | 568/606 |
| 5,567,859 A | 10/1996 | Emanuele et al. | 568/624 |
| 5,605,687 A | 2/1997 | Lee | 424/78.06 |
| 5,691,387 A | 11/1997 | Emanuele et al. | 568/723 |
| 5,696,298 A | 12/1997 | Emanuele et al. | 568/623 |
| 5,800,711 A | 9/1998 | Reeve et al. | 210/639 |
| 5,990,241 A | 11/1999 | Emanuele et al. | 525/88 |
| RE36,665 E | 4/2000 | Emanuele et al. | 568/624 |
| RE37,285 E | 7/2001 | Emanuele et al. | 514/723 |
| 6,359,014 B1 | 3/2002 | Emanuele et al. | 514/723 |
| 6,747,064 B2 | 6/2004 | Emanuele et al. | 514/44 |
| RE38,558 E | 7/2004 | Emanuele et al. | 568/623 |
| 6,761,824 B2 | 7/2004 | Reeve et al. | 210/639 |
| 6,977,045 B2 | 12/2005 | Reeve et al. | 210/639 |
| 7,846,426 B2 | 12/2010 | Metzger et al. | 424/78.38 |
| 8,372,387 B2 | 2/2013 | Markham et al. | 424/78.31 |
| 8,580,245 B2 | 11/2013 | Metzger et al. | 424/78.38 |
| 8,852,568 B2 | 10/2014 | Ng et al. | 424/78.3 |
| 2002/0183398 A1 | 12/2002 | Emanuele et al. | 514/44 |
| 2003/0206910 A1 | 11/2003 | Nicol et al. | 514/44 |
| 2004/0258718 A1 | 12/2004 | Meadows et al. | 424/70.15 |
| 2005/0095221 A1 | 5/2005 | Balasubramanian et al. | 424/78.38 |
| 2007/0237740 A1 | 10/2007 | Reddington et al. | 424/78.38 |
| 2008/0260681 A1 | 10/2008 | Metzger et al. | 424/78.38 |
| 2008/0269449 A1 | 10/2008 | Chattopadhyay et al. | 526/329.7 |
| 2009/0246162 A1 | 10/2009 | Markham et al. | 424/400 |
| 2010/0178269 A1 | 7/2010 | Markham et al. | 424/78.18 |
| 2011/0033412 A1 | 2/2011 | Ng et al. | 424/78.3 |
| 2011/0044935 A1 | 2/2011 | Metzger et al. | 424/78.38 |
| 2011/0212047 A1* | 9/2011 | Hunter | A61K 31/337 424/78.17 |

(Continued)

FOREIGN PATENT DOCUMENTS

| | | |
|---|---|---|
| WO | WO 94/08596 | 4/1994 |
| WO | WO 2006/037031 | 4/2006 |

(Continued)

OTHER PUBLICATIONS

U.S. Appl. No. 14/793,670, filed Jul. 7, 2015.
U.S. Appl. No. 14/793,730, filed Jul. 7, 2015.
Letter/Written Disclosure of the Supplemental Information Disclosure Statement for the above-referenced application, filed herewith Sep. 24, 2015, 2 pages.
Sabbah et al., "A canine model of chronic heart failure produced by multiple sequential coronary microembolizations," Am J Physiol 260:H1379-H1384 (1991).

(Continued)

*Primary Examiner* — Susan Tran

(74) *Attorney, Agent, or Firm* — Think IP, PC; Robert Prince

(57) ABSTRACT

Provided methods of administering poloxamer 188 for treating heart failure by only a single short relatively high dose infusion, or by regimen that includes the single infusion followed by additional infusions at intervals of 1-4 weeks.

37 Claims, 19 Drawing Sheets

(56) References Cited

U.S. PATENT DOCUMENTS

| | | | |
|---|---|---|---|
| 2013/0129662 A1 | 5/2013 | Markham et al. | 424/78.31 |
| 2013/0177524 A1 | 7/2013 | Emanuele et al. | 424/78.31 |
| 2014/0056839 A1 | 2/2014 | Zhang et al. | 424/78.06 |
| 2015/0030559 A1 | 1/2015 | Ng et al. | 424/78.3 |
| 2015/0093368 A1 | 4/2015 | Emanuele et al. | 424/78.31 |
| 2015/0190421 A1 | 7/2015 | Markham et al. | 424/78.3 |

FOREIGN PATENT DOCUMENTS

| | | |
|---|---|---|
| WO | WO 2006/044738 | 4/2006 |
| WO | WO 2006/091941 | 8/2006 |
| WO | WO 2008/016640 | 2/2008 |
| WO | WO 2009/023177 | 2/2009 |
| WO | WO 2012/068079 | 5/2012 |
| WO | WO 2012/091361 | 7/2012 |
| WO | WO 2015/058013 | 4/2015 |

OTHER PUBLICATIONS

Sabbah et al., "Hemodynamic properties of a new-generation positive luno-inotropic agent for the acute treatment of advanced heart failure," Am J Cardiol 99:41A-46A (2007).

Sabbah et al., "Short (2 hour) intravenous infusion of purified poloxamer 188 (MST-188) elicits prolonged (1-2 weeks) improvement in LV ejection fraction and suppresses elevations of plasma Troponin-I and nt-pro Brain Natriuretic Peptide in dogs with advanced heart failure," J Cardiac Failure 20(8):S8-S9 (2014).

Schaer et al., "Beneficial effects of RheothRx injection in patients receiving thrombolytic therapy for acute myocardial infraction: results of a randomized, double-blind, placebo-controlled trial," Circulation 94:298-307 (1996).

Schaer et al., "Reduction in reperfusion-induced myocardial necrosis in dogs by RhethRx injection (poloxamer 188 N.F.), a hemorheological agent that alters neutrophil function," Circulation 90(6):2964-2975 (1994).

Shirakabe et al., "Clinical significance of matrix metalloproteinase (MMP)-2 in patients with acute heart failure," Int Heart J 51(6): 404-410 (2010).

Schmolka, I., "A review of block polymer surfactants," Am Oil Chem Soc 54:110-116 (1977).

Smith, H. and A. Nuttall, "Experimental models of heart failure," Cardiovasc Res 19(4):181-186 (1985).

Spurney et al., "Membrane sealant poloxamer P188 protects against isoproterenol induced cardiomyopathy in dystrophin deficient mice," BMC Cardiovascular Disorders 11:20 (2011), 10 pages.

Tamaki et al., "Interleukin-16 promotes cardiac fibrosis and myocardial stiffening in heart failure with preserved ejection fraction," PLoS One 8(7):e68893, 13 pages (2013).

Terry et al., "Oxidative cell membrane alteration. Evidence for surfactant-mediated sealing," Ann N.Y. Acad Sci 888:274-284 (1999), article first published online Feb. 6, 2006.

Townsend et al., "Chronic administration of membrane sealant prevents severe cardiac injury and ventricular dilation in dystrophic dogs," J Clin Invest 120:1140-1150 (2010).

Watanabe, M. and T. Okada, "Lysophosphadtidylcholine-induced myocardial damage is inhibited by pretreatment with poloxamer 188 in isolated rat heart," Mol Cell Biochem 248: 209-215 (2003).

Weiner et al., "Liposome-collagen gel matrix: a novel sustained drug delivery system," J Pharm Sci 74(9):922-925 (1985).

Yasuda et al., "Dystrophic heart failure blocked by membrane sealant poloxamer," Nature 436:1025-1029 (2005).

Jessop, P., "Asymmetric catalysis in supercritical fluids," *Supercritical Fluid Technology for Drug Product Development*, [edited by] Peter York et al., New York: Marcel Dekker, Inc., c2005, pp. 470-473.

Zaca et al., "Chronic monotherapy with rosuvastatin prevents progressive left ventricular dysfunction and remodeling in dogs with heart failure," J Am Coll Cardiol 50(6):551-557 (2007).

Zile et al., "New concepts in diastolic dysfunction and diastolic heart failure: Part 1: diagnosis, prognosis, and measurements of diastolic function," Circulation 105(11):1387-1393 (2002).

Zile et al., "Heart failure with preserved ejection fraction: is this diastolic heart failure?," J Am Coll Cardiol 41(9):1519-1522 (2003).

Zimmerli et al., "Urinary proteomic biomarkers in coronary artery disease," Mol Cell Proteomics 7(2):290-298 (2008).

Zhang et al., "Poloxamer 188 prolongs survival of hypotensive resuscitation and decreases vital tissue injury after full resuscitation," Shock 32(4):442-450 (2009).

International Search Report and Written Opinion, mailed Aug. 19, 2014, in connection with International Patent Application No. PCT/US2014/045627, 12 pages.

Written Opinion, mailed Jan. 16, 2015, in connection with International Patent Application No. PCT/US2014/045627, 7 pages.

International Search Report and Written Opinion, mailed Sep. 8, 2015, in connection with International Patent Application No. PCT/US2015/039426, 17 pages.

International Search Report and Written Opinion, mailed Sep. 11, 2015, in connection with International Patent Application No. PCT/US2015/039418, 15 pages.

International Search Report and Written Opinion, mailed Sep. 8, 2015, in connection with International Patent Application No. PCT/US2015/039456, 15 pages.

International Search Report and Written Opinion, mailed Dec. 2, 2014, in connection with International Patent Application No. PCT/US2014/060982, 15 pages.

Response, filed Aug. 17, 2015, to International Search Report and Written Opinion, mailed Dec. 2, 2014, in connection with International Patent Application No. PCT/US2014/060982, 34 pages.

Mast Therapeutics Press Release Jan. 6, 2014, "Mast Therapeutics Announces Positive Data in Model of Heart Failure," [online][retrieved on May 20, 2014] Retrieved from:<URL:masttherapeutics.com/investors/news/?releaseid-1887966>, 2 pages.

Mast Therapeutics Press Release Feb. 18, 2014, "Mast Therapeutics Provides Additional Results from Nonclinical Heart Failure Study," [online][retrieved on May 20, 2014] Retrieved from:<URL:masttherapeutics.com/investors/news/?releaseid=1900672>, 3 pages.

Mast Therapeutics: United States Securities and Exchange Commission Form 10-K Annual Report Pursuant to Section 13 or 15(d) of the Securities Exchange Act of 1934, for the fiscal year ended Dec. 31, 2013 [online] [retrieved Aug. 26, 2015] Retrieved from <URL:masttherapeutics.com/investors/secfilings/?group=All &pg=6, 131 pages.

Mast Therapeutics, "A Brief History of MST-188," [online][retrieved on May 20, 2014] Retrieved from <URL:sec.gov/Archives/edgar/data/1160308/000119312514192551/d725005dex991.htm>, 2 pages.

Mast Therapeutics: United States Securities and Exchange Commission Form 8-K Current Report Pursuant to Section 13 or 15(d) of the Securities Exchange Act of 1934, Jun. 5, 2014 [online] [retrieved Aug. 27, 2015] Retrieved from <URL:masttherapeutics.com/investors/seefilings/?group=All$pg=2, 21 pages.

Mast Therapeutics, "Mast Therapeutics Corporate Overview Jun. 25, 2015," [online][retrieved on Aug. 27, 2015] Retrieved from <URL:sec.gov/Archives/edgar/data/1160308/000156459015005237/mstx-ex991_2015062554.htm>, 60 pages.

Mast Therapeutics Press Release Aug. 7, 2014, "Mast Therapeutics to present at the Canaccord Genuity 34th Annual Growth Conference on Aug. 14th," [online][retrieved on Aug. 20, 2014] retrieved from <URL:masttherapeutics.com/investors/news/?releaseid=1956499>, 2 pages.

Mast Therapeutics Press Release Jun. 16, 2014, "Mast Therapeutics initiates sub-study within phase 3 epic trial," [online][retrieved on Aug. 20, 2014] retrieved from <URL:masttherapeutics.com/investors/news/?releaseid=1939998>, 3 pages.

Mast Therapeutics Press Release Dec. 9, 2014, "Mast announces plans for development of Vepoloxamer (MST-188) in heart failure," [online][retrieved on Dec. 9, 2014] retrieved from <URL:masttherapeutics.com/investors/news/?releaseid=1996054>, 3 pages.

(56) References Cited

OTHER PUBLICATIONS

Mast Therapeutics Press Release Feb. 4, 2015, "Mast Therapeutics announces initiation of phase 2a studies of AIR001 in patients with heart failure with preserved ejection fraction (HFpEF)," [online][retrieved on Feb. 9, 2015] retrieved from <URL:mast-therapeutics.com/investors/news/?releaseid=2013429>, 3 pages.
Mast Therapeutics Press Release Feb. 11, 2015, "Mast Therapeutics announces new data supporting Vepoloxamer in embolic stroke," [online][retrieved on Feb. 11, 2015] retrieved from <URL:mast-therapeutics.com/investors/news/?releaseid=2015639>, 3 pages.
Mast Therapeutics Press Release Mar. 2, 2015, "Mast announces results from nonclinical study investigating repeat treatment with Vepoloxamer in advanced heart failure," [online][retrieved on Mar. 9, 2015] retrieved from <URL:masttherapeutics.com/investors/news/?releaseid=2021506>, 3 pages.
Mast Therapeutics Press Release Mar. 23, 2015, "Mast to develop Vepoloxamer (MST-188) in chronic heart failure," [online] [retrieved on Mar. 24, 2015] Retrieved from <URL:mast-therapeutics.com/investors/news/?releaseid=2027689>, 3 pages.
Culley, B., "Mast Therapeutics, Inc." presented at Canaccord Genuity 34th Annual Growth Conference on Aug. 14, 2014. Presentation. 32 pages.
Culley, B., "Mast Therapeutics, Inc." presented at the Rodman and Renshaw 16th Annual Global Investment Conference on Sep. 9, 2014. Presentation. 32 pages.
Sabbah et al., "Short (2 hour) intravenous infusion of Vepoloxamer (MST-188) elicits prolonged (1-2 weeks) improvement in biomarkers in dogs with advanced heart failure," Presented at American Heart Association Scientific Sessions, Nov. 19, 2014, 1 page.
Zhang et al., "Combination of vepoloxamer and tPA extends the therapeutic window of stroke," International Stroke Conference Feb. 11, 2015, 1 page.
Letter/Written Disclosure of the Information Disclosure Statement for the above-referenced application, filed herewith Sep. 23, 2015, 2 pages.
Adams et al., "Experimental evaluation of pluronic F68 (A non-ionic detergent) as a method of diminishing systemic fat emboli resulting from prolonged cardiopulmonary bypass," Surg Forum 10:585-589 (1960).
Adams-Graves et al., "RheothRx (Poloxamer 188) Injection for the Acute Painful Episode of Sickle Cell Disease: A Pilot Study," Blood 90:2041-2046 (1997).
Armstrong et al., "Modulation of red blood cell aggregation and blood viscosity by the covalent attachment of pluronic copolymers," Biorheology 38:239-247 (2001).
Ballas et al., "Safety of purified poloxamer 188 in sickle cell anemia phase I study of a non-ionic surfactant in the management of acute chest syndrome," Hemoglobin 28(2):85-102 (2004).
Bentley et al., "Purification of Pluronic F-68 for perfluorochemical emulsification," J Pharmacy and Pharmacology 41(9): 661-663 (1988).
Borlaug B. and W. Paulus, "Heart failure with preserved ejection fraction: pathophysiology, diagnosis, and treatment," Eur Heart J. 32(6):670-679(2011).
Borlaug B. and M. Redfield, "Diastolic and systolic heart failure are distinct phenotypes within the heart failure spectrum," Circulation 123(18):2006-2013 (2011).
Burns et al., "Severe controlled hemorrhage resuscitation with small vol. poloxamer 188 in sedated miniature swine," Resuscitation 82:1453-1459 (2011).
Cooper et al., "The role of endomyocardial biopsy in the management of cardiovascular disease: a scientific statement from the American Heart Association, the American College of Cardiology, and the European Society of Cardiology Endorsed by the Heart Failure Society of America and the Heart Failure Association of the European Society of Cardiology," Eur Heart J 28(24):3076-3093 (2007).
Danielson et al., "Use of Pluronic F-68 to diminish fat emboli and hemolysis during cardiopulmonary bypass. A controlled clinical study," J Thorac Cardiovasc Surg 59(2):178-184 (1970).
Dodge et al., "Usefulness and limitations of radiographic methods for determining left ventricular volume," The American Journal of Cardiology 18(1):10-24 (1966).
Emanuele, R. M. and B. Balasubramaniam, "Differential effects of commercial-grade and purified poloxamer 188 on renal function," Drugs R&D 14(2):73 -83 (2014).
Emanuele, R. M., "FLOCOR: a new anti-adhesive, rheologic agent," Expert Opin Investig Drugs 7(7):1193-1200 (1998).
Fareed et al., "Facilitation of urokinase-mediated fibrinolysis by MST-188," FASEB J 28(1): 833.7 (abstract).
Feldman et al., "The role of tumor necrosis factor in the pathophysiology of heart failure," J Am Coll Cardio. 35(3):537-544 (2000).
Grindel et al., "Distribution, metabolism, and excretion of a novel surface-active agent, purified poloxamer 188, in rats, dogs, and humans," J of Pharm Sci 90(9): 1936-1947 (2002).
Grindel et al., "Pharmacokinetics of a novel surface-active agent, purified poloxamer 188, in rat, rabbit, dog and man," Biopharm Drug Dispos 23:87-103 (2002).
Grover et al.,"The effect of Pluronic F-68 on circulatory dynamics and renal and carotid artery flow during hemorrhagic shock," J Surg Res 17:30-35 (1974).
Hymes et al., "The influence of an industrial surfactant Pluronic F-68, in the treatment of hemorrhagic shock," J Surg Res 11(4):191-197 (1971).
Ilsar et al., "Acute intravenous bolus injection of Poloxamer-188 improves left ventricular function in dogs with heart failure," J Am col. Cardiol 55 (Suppl. 1): A16.E146, 2 pages (2010).
IUPAC-IUB Commission on Bio-chemical Nomenclature Symbols for Amino-Acid Derivatives and Peptides, Biochemistry 11:1726-1732 (1972).
Juneman et al., "The effects of Poloxamer-188 on left ventricular function in chronic heart failure after myocardial infarction," Cardiovasc Pharmacol 60: 293-298 (2012).
Justicz et al., "Reduction of myocardial infarct size by poloxamer 188 and mannitol in a canine model," Am Heart J 122(3 Pt 1):671-680 (1991).
Karmarkar, "Poloxamers and their applications" Pharmainfo.net Published online Oct. 27, 2008; <URL:pharmainfo.net/pharma-student-magazine/poloxamers-and-their-applications-0 [retrieved Jul. 21, 2015], 31 pages.
Kiechl et al., "Chronic infections and the risk of carotid atherosclerosis: prospective results from a large population study," Circulation 103:1064-1070 (2001).
Krishnaswamy et al., "Utility of B-natriuretic peptide levels in identifying patients with left ventricular systolic or diastolic dysfunction," Am J Med 111(4):274-279 (2011).
Komegay et al., "Canine models of Duchenne muscular dystrophy and their use in therapeutic strategies," Mamm Genome 23(1-2):85-108 (2012).
Lane, T. A. and V. Krukonis, "Reduction in the toxicity of a compound of an artificial blood substitute by supercritical fluid fractionation," Transfusion 28:375-378 (1988).
Lee et al., "Surfactant-induced sealing of electropermeabilized skeletal muscle membranes in vivo," Proc Natl Acad Sci USA 89:4524-4528 (1992).
Little, W. C. and M. R. Zile, "HFpEF: cardiovascular abnormalities not just comorbidities," Circ Heart Fail 5(61:669-671 (2012).
Lourneço et al., "Higher C-reactive protein predicts worse prognosis in acute heart failure only in noninfected patients," Clin Cardiol 33(11):708-714 (2010).
Mayer et al., "Effects of poloxamer 188 in hemodynamics and survival in a rabbit model of hemorrhagic shock and retransfusion," Published Jun. 24, 1990[online] Retrieved from <URL:dtic.mil/dtic/tr/fulltext/u2/a224534.pdf [retrieved Aug. 25, 2014], 22 pages.
Mayer et al., "Effects of poloxamer 188 in a rabbit model of hemorrhagic shock," Database Biosis Biosciences Information Services, abstract, Database accession No. PREV199497408356, 2 pages (1994).
Mayer et al., "Effects of poloxamer 188 in a rabbit model of hemorrhagic shock," Ann Clin Lab Sci 24(4):302-311 (1994).

(56) References Cited

OTHER PUBLICATIONS

McDonald et al., "Hemodynamic, left ventricular structural and hormonal changes after discrete myocardial damage in the dog," J Am Coll Cardiol 19(2):460-467 (1992).

McMurray et al., "ESC Guidelines for diagnosis and treatment of acute and chronic heart failure," European Heart Journal 33:1787-1847 (2012).

Miller et al., "Diagnostic performance of coronary angiography by 64-row CT," N Engl J Med 359(22):2324-2336 (2008).

Moloughney, J. G. and N. Weisleder, "Poloxamer 188 (P188) as a membrane resealing reagent in biomedical applications," Recent Pat Biotechnol 6(3):200-211 (2012).

Nagayoshi et al., "Differences in oxidative stress markers based on the aetiology of heart failure: comparison of oxidative stress in patients with and without coronary artery disease," Free Radic Res 43(12):1159-1166 (2009).

National Institute of Health, *Guide for the Care and Use of Laboratory Animals*, NIH Publication No. 85-23. Revised 2011, 247 pages.

O'Keefe et al., "Poloxamer-188 as an adjunct to primary percutaneous transluminal coronary angioplasty for acute myocardial infarction," Am J Cardiol 78:747-750 (1996).

Owan et al., "Trends in prevalence and outcome of heart failure with preserved ejection fraction," N Engl J Med. 355(3):251-259 (2006).

Quinlan et al., "Poloxamer 188 failed to prevent exercise-induced membrane breakdown in mdx skeletal muscle fibers," Neuromuscular Disord 16(12): 855-864 (2006).

Raev, D., "Which left ventricular function is impaired earlier in the evolution of diabetic cardiomyopathy? An echocardiographic study of young type I diabetic patients," Diabetes Care 17(7):633-639 (1994).

Rastogi et al., "Myocardial transfection with naked DNA plasmid encoding hepatocyte growth factor prevents the progression of heart failure in dogs," Am J Phys Heart and Circ Phys 300:H1501- H1509 (2011).

Reeve, L., "The Poloxamers: Their Chemistry and Medical Applications" found in *Handbook of Biodegradable Polymers*, Domb et al., Eds., Harward Academic Publishers, OPA: Amsterdam, Chapter 12, pp. 231-249 (1997).

Riegger, A. J. G. and G. Liebau, "The renin-angiotensin-aldosterone system, antidiuretic hormone and sympathetic nerve activity in an experimental model of congestive heart failure in the dog," Clin Sci (Lond) 62(5):465-469 (1982).

\* cited by examiner

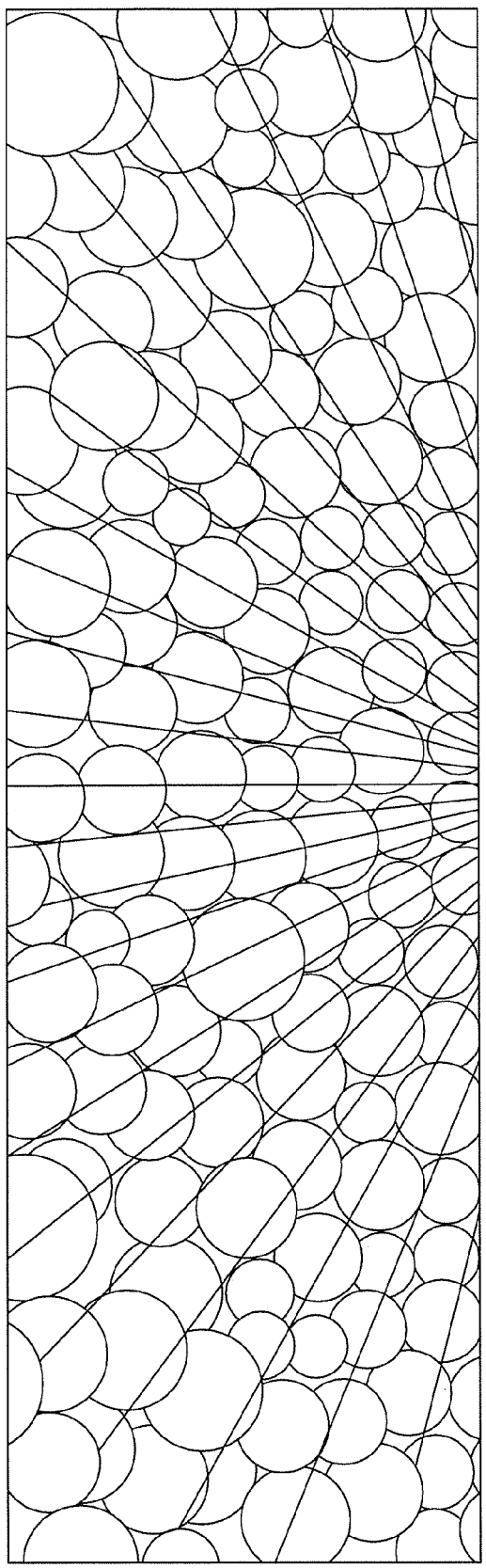

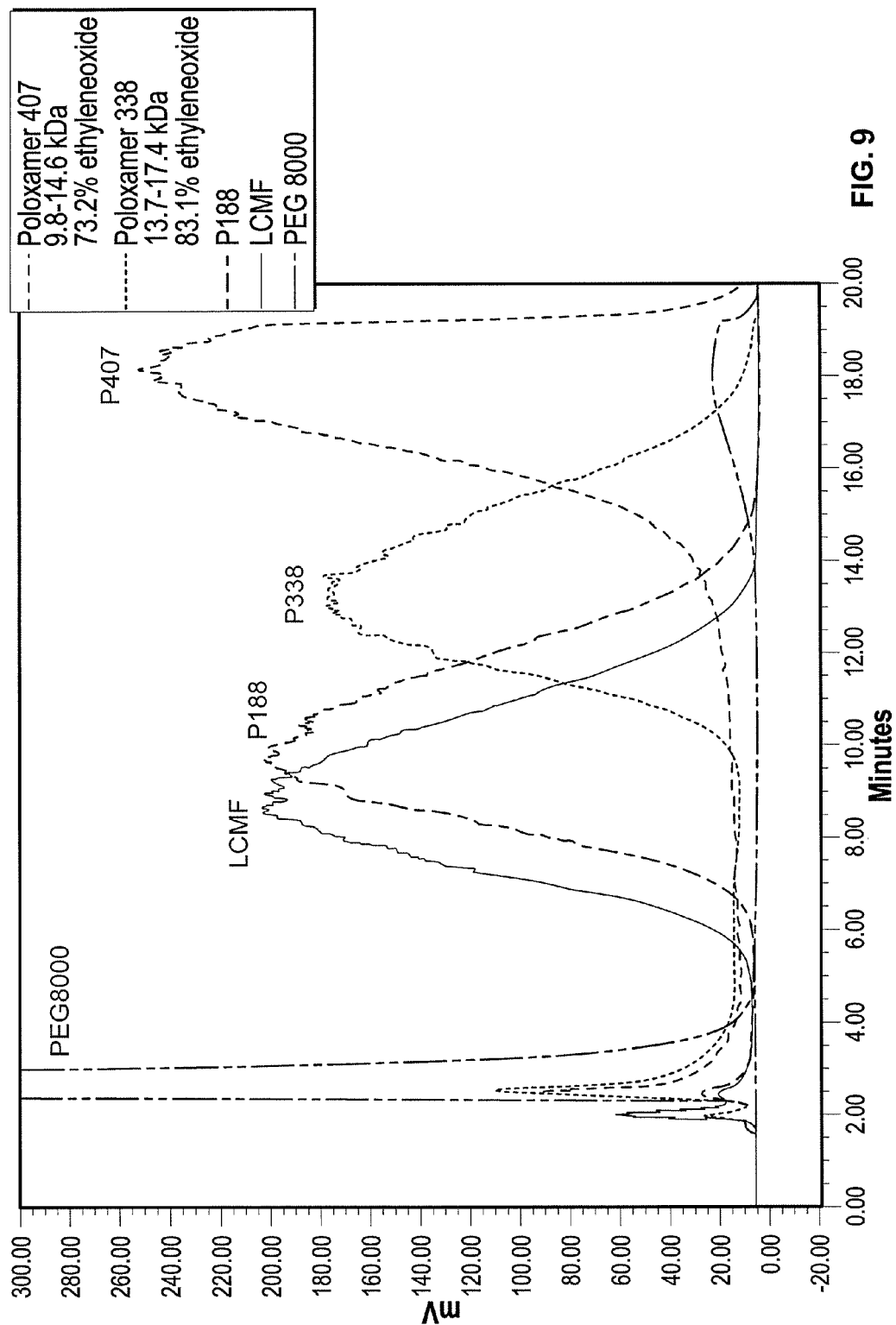

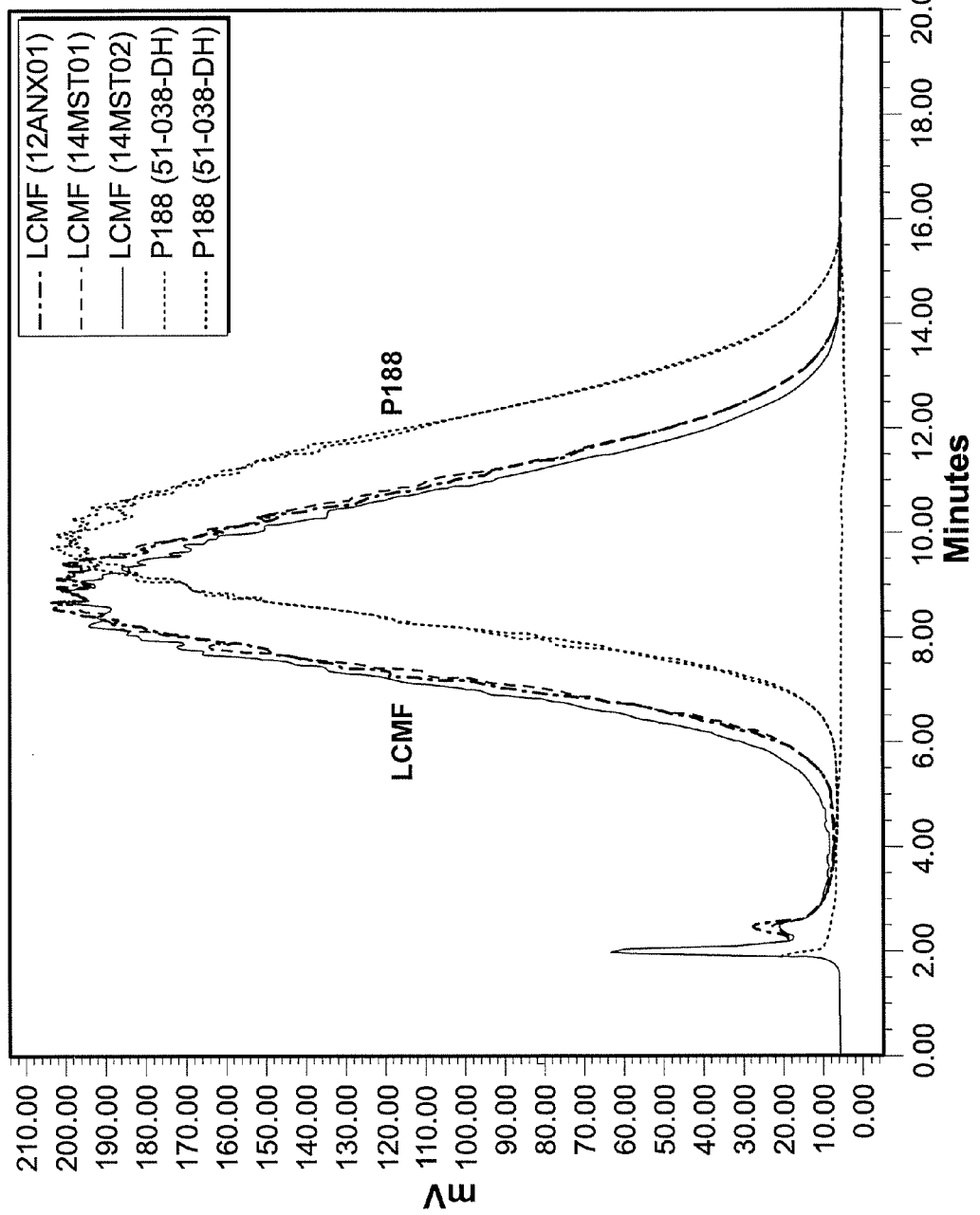

PROTOCOL

| Time | 0 | 2h | 24h | 1w | 2w | 3w | 3w+ 2h | 3w+ 24h | 4w | 5w | 6w |
|---|---|---|---|---|---|---|---|---|---|---|---|
| Drug Infusion | X | X | | | | X | X | | | | |
| Cardiac Cath | X | X | X | X | X | X | X | X | X | X | X |
| 2-D Echo | X | X | X | X | X | X | X | X | X | X | X |
| Blood Sample | X | X | X | X | X | X | X | X | X | X | X |
| Heart Tissue | | | | | | | | | | | X |

FIG. 11B

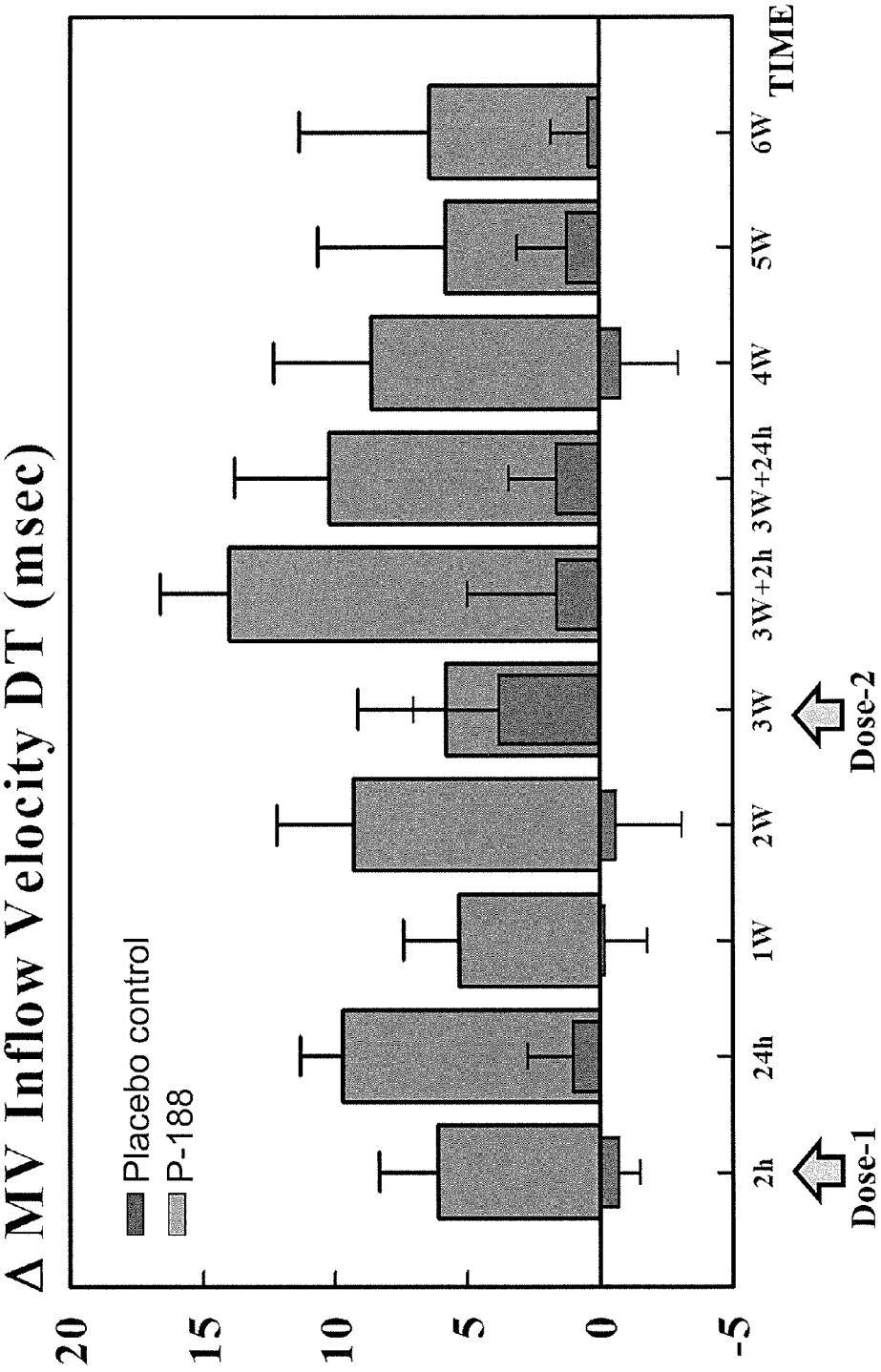
FIG. 12F  P-188 in Dogs with Advanced Heart Failure

US 9,757,411 B2

POLOXAMER THERAPY FOR HEART FAILURE

RELATED APPLICATIONS

Benefit of priority is claimed to U.S. Provisional Application Ser. No. 62/021,691, to R. Martin Emanuele, Santosh Vetticaden and Patrick Keran, filed Jul. 7, 2014, and entitled "POLOXAMER THERAPY FOR HEART FAILURE." Benefit of priority also is claimed to U.S. Provisional Application Ser. No. 62/126,400, to R. Martin Emanuele, Santosh Vetticaden and Patrick Keran, filed Feb. 27, 2015, and entitled "POLOXAMER THERAPY FOR HEART FAILURE." This application is a continuation-in-part of International PCT Application No. PCT/US14/45627, to R. Martin Emanuele, Santosh Vetticaden and Patrick Keran, filed Jul. 7, 2014, and entitled "POLOXAMER THERAPY FOR HEART FAILURE."

This application is related to International PCT Application No. PCT/US2015/039426, to R. Martin Emanuele, Santosh Vetticaden and Patrick Keran, filed the same day herewith, and entitled "POLOXAMER THERAPY FOR HEART FAILURE."

This application is related to U.S. Provisional Application Ser. No. 62/021,697, to R. Martin Emanuele and Mannarsamy Balasubramanian, filed Jul. 7, 2014, entitled "A POLOXAMER COMPOSITION FREE OF LONG CIRCULATING MATERIAL AND METHODS FOR PRODUCTION AND USES THEREOF." This application also is related to International PCT Application No. PCT/US2015/039418, to R. Martin Emanuele and Mannarsamy Balasubramanian, filed the same day herewith, and entitled "A POLOXAMER COMPOSITION FREE OF LONG CIRCULATING MATERIAL AND METHODS FOR PRODUCTION AND USES THEREOF." This application also is related to U.S. application Ser. No. 14/793,670, to R. Martin Emanuele and Mannarsamy Balasubramanian, filed the same day herewith, and entitled "A POLOXAMER COMPOSITION FREE OF LONG CIRCULATING MATERIAL AND METHODS FOR PRODUCTION AND USES THEREOF."

Where permitted, the subject matter of each application is incorporated by reference in its entirety.

FIELD OF THE INVENTION

Provided herein are methods and uses of treating heart failure using a single short term infusion of a poloxamer 188, such as a long-circulating material free (LCMF) poloxamer. The short term infusion can be repeated at intervals of not less than one week to sustain and/or improve the therapeutic effect.

BACKGROUND

Heart failure is a chronic, progressive condition in which heart muscle is unable to pump sufficient blood to meet the body's needs. A healthy heart pumps blood continuously through the circulatory system to deliver oxygen- and nutrient-rich blood to the body's cells and permit normal functioning. A variety of diseases and conditions, however, can weaken the heart and reduce its ability to deliver an adequate blood supply, such as hypertension, coronary artery disease and others. It is estimated that more than 20 million individuals worldwide, including five to six million in the United States (U.S.), suffer from heart failure. It is the most common diagnosis for hospital admission in the U.S. for patients over the age of 65.

Most existing therapies target indirect methods that reduce the workload on the heart, but do not directly improve heart function. For example, ACE inhibitors widen blood vessels (vasodilation) to lower blood pressure and reduce the resistance against which the heart must pump. These therapies, however, do not directly improve the heart's ability to contract normally. Existing therapies also provide only short-term symptomatic relief, and therefore require multiple repeat infusions at a high frequency. Hence, there is a need for alternative treatments for heart failure.

SUMMARY

Provided herein are methods of using a poloxamer, such as poloxamer 188, (see, e.g., U.S. Pat. No. 5,696,298), including the long circulating material free (LCMF) poloxamer described herein (see, also, copending U.S. application Ser. No. 14/793,670 and International PCT Application No. PCT/US2015/039418, which describe the LCMF poloxamer), for treating heart failure. For example, the method for treating heart failure in a subject includes: administering to the subject a composition comprising an amount of a polyoxyethylene/polyoxypropylene copolymer having the chemical formula $HO(C_2H_4O)_{a'}$—$(C_3H_6O)_b$—$(C_2H_4O)_aH$, where the copolymer preparation has been purified to remove low molecular weight impurities; a' and a are the same or different and each is an integer, whereby the hydrophile portion represented by $(C_2H_4O)$ constitutes approximately 60% to 90% or 60%-90% by weight of the compound; b is an integer, whereby the hydrophobe represented by $(C_3H_6O)$ has a molecular weight of about 1,200 Da to about 2,300 Da or 1,200 to 2,300 Da. In such methods, an effective dose of the poloxamer copolymer is administered as a single short term infusion which after at least one week, can be repeated one or more times. The subject can have diastolic or systolic heart failure. In particular aspects of the method, the subject has systolic heart failure. For example, the subject having systolic heart failure is identified for treatment if the subject has a left ventricular ejection fraction (LVEF) of less than 40%. In some embodiments, treatment is effected by only a single dose.

Provided herein is a single course of treatment in which a relatively high dose of 100 mg/kg or higher as described herein is administered as a relatively short infusion (the course of treatment). In some embodiments, this high dose infusion is administered only once. In other embodiments, this course treatment is administered once, with one or more additional courses of treatment administered at least 1 week after the first, generally up to 3-4 weeks after the first. The method and regimen and dosing described solves the problem of chronic treatment, in which multiple courses of treatment can be administered for a long time, as long as years. A dose of the polyoxyethylene/polyoxypropylene copolymer below 100 mg/kg is not effective. Consequently, it is advantageous to formulate the polyoxyethylene/polyoxypropylene copolymer for administration at a concentration of at least 15%, at least 20%, at least 25%, 10% to 25%, 22.5%, 10% to 20%, 15% to 20%, 15% to 30%, 15% to 28%, 20 to 23%, 15% to 25%, or 20 to 25% so that it can be administered in a relatively short infusion.

In accord with the methods herein, following the first course of treatment, if further treatment is to be administered, the second course is effected 7 days-28 days after the first treatment. A third and any subsequent treatments are administered 21-42 days after the prior administration. For each course of treatment, the gravimetric dose can be the same or different; the dose can be increased or decreased. The treatment generally is administered in less than 24 hours, less than 12 hours, less than 6 hours, less than 3 hours, and typically in 2-6 hours. A starting dose is in the range of 100 mg/kg to 675 mg/kg, such as 100 mg/kg to 600 mg/kg, 200 to 500 mg/kg, 350 to 500 mg/kg or 450 to 500 mg/kg. For example, assuming an average human weighs 70 kg, the dose is between about or is between 5 to 50 gms of the copolymer Provided are methods for treating heart failure by administering a single infusion of a polyoxyethylene/polyoxypropylene copolymer, whereby treatment is effected. An additional infusion can be administered at least one week and up to 3 or 4 weeks after the first infusion. The time between infusions can be increased. Dosage is effective for treatment, and, is typically, between 100 mg/kg and 675 mg/kg, administered as single infusion. Dosage can be titrated as needed during the course of treatment, including for subsequent treatments after the first treatment.

In particular, provided are methods for treating heart failure by: administering to a subject suspected of or experiencing heart failure, a composition comprising an amount of a polyoxyethylene/polyoxypropylene copolymer having the chemical formula $HO(C_2H_4O)_{a'}-(C_3H_6O)_b-(C_2H_4O)_aH$, where the polyoxyethylene/polyoxypropylene copolymer is as defined herein. For example, the polyoxyethylene/polyoxypropylene copolymer of the above formula is a poloxamer 188 that has been purified to remove low molecular weight impurities; a' and a are the same or different and each is an integer, whereby the hydrophile portion represented by $(C_2H_4O)$ constitutes approximately 60% to 90% or 60%-90% by weight of the compound; b is an integer, whereby the hydrophobe represented by $(C_3H_6O)$ has a molecular weight of about 1,200 Da to about 2,300 Da or 1,200 to 2,300 Da. The copolymer can be administered only once as a single infusion, or after one week or at least one week, the infusion is repeated least one more time. The dosage for each infusion can be the same or different, and can be determined by assessing the condition of the subject's heart. For example, a second infusion and any subsequent infusion of the polyoxyethylene/polyoxypropylene copolymer can be administered 2 to 3 weeks following the prior infusion, or the second infusion and any subsequent infusion is administered at 3-4 week intervals following the prior infusion. In some embodiments, the additional infusions can be administered at increasing intervals, such as increasing each by at least 1 week, whereby a third infusion is administered at 4-5, 5-6 or 4-6 weeks after the second infusion. The dosage is decreased with each infusion. Performance of the heart can be monitored between infusions. Performance of the heart can be assessed before each infusion, and, optionally, the dose can be decreased as the performance of the heart improves or adjusted based on the results of the assessment. Dosages can be between 100-675 mg/kg or between about 100 mg/kg and about 675 mg/kg, such as between 100-500 mg/kg or between about 100 mg/kg and about 500 mg/kg. A typical first dose is about or at 400-500 mg/kg. Each dose is administered as a single infusion during a period of less than 24 hours, less than 12 hours, less than 6 hours or less than 3 hours, or, for example, for 2-6 hours. Such time depends upon a variety of parameters, including the actual dosage, the concentration of the copolymer and the subject.

Heart failure can be manifested by a variety of symptoms. If necessary a subject for treatment can be identified prior to administering the poloxamer. These symptoms include, but are not limited to, the presence of one or more of arrhythmias, elevated blood pressure, narrowing arteries, catheterization, ischemia and altered cardiac output. The heart failure can be systolic heart failure. Systolic heart failure can be manifested by reduced left ventricular (LV) ejection fraction (EF), increased LV end-systolic volume, left ventricular hypertrophy or elevated LV end-systolic pressure. The heart failure can be diastolic heart failure. Diastolic heart failure can be manifested by increased myocardial mass with normal left ventricular chamber size or elevated LV end-diastolic pressure.

The polyoxyethylene/polyoxypropylene copolymer administered has the above-noted formula and can have a polydispersity value less than approximately 1.07. The polyoxyethylene/polyoxypropylene copolymer can have no more than 1.5% of the total components in the distribution of the co-polymer as low molecular weight components having an average molecular weight of less than 4,500 Daltons; and no more than 1.5% of the total components in the distribution of the co-polymer are high molecular weight components having an average molecular weight of greater than 13,000 Daltons. For example, the polyoxyethylene/polyoxypropylene copolymer can be one in which the molecular weight of the hydrophobe $(C_3H_6O)$ is about or is 1,750 Da.

The polyoxyethylene/polyoxypropylene copolymer can be one with the above-noted formula, where the hydrophobe represented by $(C_3H_6O)$ has a molecular weight of about 1,400 to 2,000 Da or 1,400 to 2,000 Da, and a hydrophile portion constituting approximately 70% to 90% or 70% to 90% by weight of the copolymer. The hydrophobe can have a molecular weight of 1,500 to 2,100 Da or 1,700 to 1,900 Da. In certain embodiments the average molecular weight of the polyoxyethylene/polyoxypropylene copolymer is approximately or is 8,400-8,800 Da. In particular, the copolymer is a poloxamer 188, particularly a poloxamer 188 in which low molecular weight impurities are removed. In other embodiments, the poloxamer is an LCMF poloxamer 188, which is described herein and in copending U.S. application Ser. No. 14/793,670 and International PCT Application No. PCT/US2015/039418, each filed the same day herewith.

For all embodiments, including all methods and uses and combinations and compositions, the polyoxyethylene/polyoxypropylene copolymer can be a long-circulating material-free (LCMF) poloxamer as described herein. In particular, the LCMF poloxamer includes those where the polyoxyethylene/polyoxypropylene copolymer has the formula: $HO(CH_2CH_2O)_{a'}-[CH(CH_3)CH_2O]_b-(CH_2CH_2O)_aH$, where each of a and a', which can be the same or different, is an integer such that the percentage of the hydrophile $(C_2H_4O)$ is between approximately or between 60% and 90% by weight of the total molecular weight of the copolymer; b is an integer such that the molecular weight of the hydrophobe $(C_3H_6O)$ is between approximately 1,300 and 2,300 Daltons; no more than 1.5% of the total components in the distribution of the co-polymer are low molecular weight components having an average molecular weight of less than 4,500 Daltons; no more than 1.5% of the total components in the distribution of the co-polymer are high molecular weight components having an average molecular weight of greater than 13,000 Daltons; the polydispersity value of the copolymer is less than approximately 1.07 or less than 1.07; and the circulating half-life of all components in the distribution of the co-polymer, when administered to a subject, particularly a human, is no more than 5.0-fold longer than the circulating half-life of the main component in the distribution of the co-polymer.

In some embodiments, the LCMF poloxamer for use in the methods and compositions and uses, is such that all components in the distribution of the co-polymer, when administered to a subject, have a circulating half-life in the plasma of the subject that is no more than 4.0-fold, 3.0-fold, 2.0 fold or 1.5-fold longer than the circulating half-life of the main component in the distribution of the co-polymer. In particular embodiments, all components in the distribution of the co-polymer, when administered to a subject, have a circulating half-life in the plasma of the subject that is no more than 1.5-fold longer than the circulating half-life of the main component in the distribution of the co-polymer. The LCMF poloxamer is one in which all of the components of the polymeric distribution clear from the circulation at approximately the same rate, such as where all components in the distribution of the co-polymer, when administered to a subject, have a circulating half-life in the plasma of the subject that is no more than the circulating half-life of the main component in the distribution of the co-polymer. For example, all components in the distribution of the co-polymer, when administered to a human subject, have a circulating half-life in the plasma of the subject that is no more than 30 hours, 25 hours, 20 hours, 15 hours, 10 hours, 9 hours, 8 hours or 7 hours, or, for example, all components in the distribution of the co-polymer, when administered to a human subject, have a half-life in the plasma of the subject that is no more than 10 hours.

The LCMF polyoxyethylene/polyoxypropylene copolymer has the above noted formula, where hydrophobe has a molecular weight of about 1,400 to 2,000 Da or 1,400 to 2,000 Da, and a hydrophile portion constituting approximately 70% to 90% or 70% to 90% by weight of the copolymer. In some embodiments, the molecular weight of the hydrophobe ($C_3H_6O$) is about or is 1,750 Da; in others or the same embodiments, the average molecular weight of the polyoxyethylene/polyoxy-propylene copolymer is 7680 to 9510 Daltons, such as about or at 8,400-8,800 Daltons. In the LCMF poloxamer, the percentage of high molecular weight components with a molecular weight of greater than or equal to 13,000 Daltons constitute less 1% of the total distribution of components of the poloxamer preparation; such preparation does not, when administered to a subject, result in a component with the longer half-life. In some embodiments, the percentage of high molecular weight components in the preparation greater than 13,000 Daltons constitutes less than 0.9%, 0.8%, 0.7%, 0.6%, 0.5% or less of the total distribution of components of the poloxamer preparation, and, that when administered, does not result in a component with the longer half-life. For all embodiments of the method herein, including the LCMF poloxamer, such as the LCMF P-188, as well as the compositions and uses, the poloxamer can have a polydispersity value of the polyoxyethylene/polyoxypropylene copolymer that is less than 1.06, 1.05, 1.04, 1.03 or less.

The LCMF poloxamer can be an LCMF P-188 poloxamer. It can be produced by a method such as a method that includes the steps of: a) introducing a poloxamer 188 solution into a suitable vessel, such as an extractor vessel, where the poloxamer is dissolved in a first alkanol to form a solution; b) contacting the poloxamer solution with an extraction solvent comprising a second alkanol and supercritical carbon dioxide under a temperature and pressure to maintain the supercritical carbon dioxide for a first defined period, where: the temperature is above the critical temperature of carbon dioxide but is no more than 40° C.; the pressure is 220 bars to 280 bars; and the alkanol is provided at an alkanol concentration that is 7% to 8% by weight of the total extraction solvent; c) increasing the concentration of the second alkanol in step b) in the extraction solvent a plurality of times in gradient steps over time of the extraction method, wherein, each plurality of times occurs for a further defined period; and in each successive step, the alkanol concentration is increased 1-2% compared to the previous concentration of the second alkanol; and d) removing the extraction solvent from the vessel, such as an extractor vessel, to thereby remove the extracted material from the raffinate poloxamer preparation.

Doses of the infusions depend upon the subject and other parameters, but typically range from about or at 100 mg/kg-675 mg/mg, including 100 mg/kg-500 mg/kg, such as 400 or 450 to 500 mg/kg. In certain embodiments, the first dose of the copolymer administered is at least or about at least 100 mg/kg, such as 100 mg/kg-675 mg/mg, including 100 mg/kg-500 mg/kg, such as 400 or 450 to 500 mg/kg. In some embodiments, the copolymer in each infusion that is administered is from or from about 200 mg/kg to 450 mg/kg. Assuming an average human weighs 70 kg, the dose is between about or is between 5-50 gms of the copolymer.

The concentration of the copolymer in the composition that is administered in each infusion can be at least 10.0 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 115 mg/mL, at least 130 mg/mL, at least 150 mg/mL, at least 200 mg/mL or at least 225 mg/mL, such as no more than 225 mg/mL. Exemplary ranges of the concentration of copolymer that is administered in each infusion is from or from about 150 mg/mL to 225 mg/mL. A typical volume administered is, for example, a volume that is 0.4 mL/kg to 3.0 mL/kg of the subject. The infusion can last up to 24 hours, such as from 1 to 24 hours, 2-10 hour, or 2-6 hours or 4-12 hours. Each infusion is repeated 1 week or more than 1 week up to 4 weeks following completion of the prior dose. For example, the infusion is repeated at least 7 days, 8 days, 9 days, 10 days, 11 days, 13 days or 14 days, 3 weeks or 4 weeks following completion of the prior dose. The dosage at each infusion can be the same as a prior dosage or different. The treatment can be continued for at least 1 week, 3 weeks, 1 month, 2 months, 3 months, 4 months, 5 months, 6 months, 7 months, 8 months, 9 months, 10 months, 11 months, a year or more.

The subject treated can have acute heart failure, such as, for example, acute decompensation. The subject treated can have chronic heart failure. The subject treated can have coronary artery disease, myocardial infarction or hypertension.

The methods can include treatment with a second (different) agent or treatment for treating heart failure. The agent can be administered with the infusion, in a separate composition, intermittently with the infusion, before an infusion or the first infusion, or other suitable regimen. Such second agents can be selected from among a diuretic, loop diuretic, a potassium sparing agent, a vasodilator, an ACE inhibitor, ARBs (angiotensin receptor blockers), an angiotensin II antagonist, Aldosterone antagonist, a positive inotrophic agent, a phosphodiesterase inhibitor, a beta-adrenergic receptor antagonist, a calcium channel blocker, a nitrate, an alpha blocker, a central alpha antagonist, a statin, Digoxin, Nitrates, chlorthalidone, amlodipine, lisinopril, doxazosin, and a combination of these agents. Treatment can include other types of treatment, such as provision of an implantable pacemakers, a defibrillator, and/or left ventricular assist device (LVAD). The heart failure can be systolic heart failure, such as systolic heart failure that is manifested by left ventricular (LV) ejection fraction (EF) is less than or equal to 40% or about 40%.

The above described methods can be implemented or described as compositions for use in treatment or a composition formulated as a medicament for use in treatment. The following description provides embodiments for the various uses. Hence, provided is a pharmaceutical composition for use in treating heart failure in subject identified or selected to have heart failure, where: the composition formulated for administration as a single infusion that is administered only one time, or optionally is repeated after 1 week. The composition comprises an amount of a polyoxyethylene/polyoxypropylene copolymer having the chemical formula $HO(C_2H_4O)_{a'}—(C_3H_6O)_b—(C_2H_4O)_aH$, where: the copolymer preparation has been purified to remove low molecular weight impurities; a' and a are the same or different and each is an integer, whereby the hydrophile portion represented by $(C_2H_4O)$ constitutes approximately 60% to 90% or 60%-90% by weight of the compound; b is an integer, whereby the hydrophobe represented by $(C_3H_6O)$ has a molecular weight of about 1,200 Da to about 2,300 Da or 1,200 to 2,300 Da. For example, the polyoxyethylene/polyoxypropylene can be formulated for single intravenous infusion of 100-675 mg/kg in a time period of 2-6 hours; for treatment effected by a single dose of the polyoxyethylene/polyoxypropylene, or for treatment effected at intervals of at least a week up to three weeks or four weeks.

The composition can be formulated for administration as a single infusion followed by a second infusion 2 to 3 weeks after the first infusion; or 3 weeks to 4 weeks after the first. The composition can be formulated for administration as a single infusion followed by a second infusion 2 to 3 weeks after the first infusion and further infusions, where the interval between infusions is increased for each infusion or is about the or the same, or is increased by at least 1 week, whereby a third infusion 4-5, 5-6 or 4-6 weeks after the second infusion. The dosage can be adjusted for each infusion. For example, the dosage can be decreased with each infusion or decreased after the first infusion only or other combinations of increasing and decreasing the dosage.

As with the methods, the heart failure can be manifested by presence of arrhythmias, elevated blood pressure, narrowing arteries, ischemia, catheterization and/or altered cardiac output. The heart failure can be systolic heart failure, such as systolic heart failure manifested by reduced left ventricular (LV) ejection fraction (EF), increased LV end-systolic volume, left ventricular hypertrophy or elevated LV end-systolic pressure. The heart failure can be diastolic heart failure, such as diastolic heart failure manifested by increased myocardial mass with normal left ventricular chamber size or elevated LV end-diastolic pressure.

As with the methods the polyoxyethylene/polyoxypropylene copolymer can be any described for use in the methods. This includes polyoxyethylene/polyoxypropylene copolymers that have a polydispersity value less than approximately 1.07; polyoxyethylene/polyoxypropylene copolymers, where no more than 1.5% of the total components in the distribution of the co-polymer are low molecular weight components having an average molecular weight of less than 4,500 Daltons; and/or no more than 1.5% of the total components in the distribution of the co-polymer are high molecular weight components having an average molecular weight of greater than 13,000 Daltons. For example, the polyoxyethylene/polyoxypropylene copolymer can be one in which the molecular weight of the hydrophobe $(C_3H_6O)$ is about or is 1,750 Da.

The polyoxyethylene/polyoxypropylene copolymer in the compositions can be one with the above-noted formula, where the hydrophobe represented by $(C_3H_6O)$ has a molecular weight of about 1,400 to 2,000 Da or 1,400 to 2,000 Da, and a hydrophile portion constituting approximately 70% to 90% or 70% to 90% by weight of the copolymer. The hydrophobe can have a molecular weight of 1,500 to 2,100 Da or 1,700 to 1,900 Da. In certain embodiments the average molecular weight of the polyoxyethylene/polyoxypropylene copolymer is approximately or is 8,400-8,800 Da. In particular embodiments, the copolymer is a poloxamer 188.

For all embodiments of the compositions for use, as described above for the methods, the polyoxyethylene/polyoxypropylene copolymer can be a long-circulating material-free (LCMF) poloxamer as described herein. In particular, the LCMF poloxamer includes those where the polyoxyethylene/polyoxypropylene copolymer has the formula: $HO(CH_2CH_2O)_{a'}—[CH(CH_3)CH_2O]_b—(CH_2CH_2O)_aH$, where a or a' is an integer such that the percentage of the hydrophile $(C_2H_4O)$ is between approximately 60% and 90% by weight of the total molecular weight of the copolymer; where a and a' are the same or different; where b is an integer such that the molecular weight of the hydrophobe $(C_3H_6O)$ is between approximately 1,300 and 2,300 Daltons; where no more than 1.5% of the total components in the distribution of the co-polymer are low molecular weight components having an average molecular weight of less than 4,500 Daltons and no more than 1.5% of the total components in the distribution of the co-polymer are high molecular weight components having an average molecular weight of greater than 13,000 Daltons; where the polydispersity value of the copolymer is less than approximately or less than 1.07; and the circulating half-life of all components in the distribution of the co-polymer, when administered to a subject, is no more than 5.0-fold longer than the circulating half-life of the main component in the distribution of the co-polymer.

In embodiments, the LCMF poloxamer in the compositions for use to treat heart failure is such that all components in the distribution of the co-polymer, when administered to a subject, have a circulating half-life in the plasma of the subject that is no more than 4.0-fold, 3.0-fold, 2.0 fold or 1.5-fold longer than the circulating half-life of the main component in the distribution of the co-polymer. In particular embodiments, all components in the distribution of the co-polymer, when administered to a subject, have a circulating half-life in the plasma of the subject that is no more than 1.5-fold longer than the circulating half-life of the main component in the distribution of the co-polymer. The LCMF poloxamer is one in which all of the components of the polymeric distribution clear from the circulation at approximately the same rate, such as where all components in the distribution of the co-polymer, when administered to a subject, have a circulating half-life in the plasma of the subject that is no more than the circulating half-life of the main component in the distribution of the co-polymer. For example, all components in the distribution of the co-polymer, when administered to a human subject, have a circulating half-life in the plasma of the subject that is no more than 30 hours, 25 hours, 20 hours, 15 hours, 10 hours, 9 hours, 8 hours or 7 hours, or, for example, all components in the distribution of the co-polymer, when administered to a human subject, have a half-life in the plasma of the subject that is no more than 10 hours.

The LCMF polyoxyethylene/polyoxypropylene copolymer in the compositions has the above noted formula, where hydrophobe has a molecular weight of about 1,400 to 2,000 Da or 1,400 to 2,000 Da, and a hydrophile portion constituting approximately 70% to 90% or 70% to 90% by weight of the copolymer. In some embodiments, the molecular weight of the hydrophobe ($C_3H_6O$) is about or is 1,750 Da; in others or the same embodiments, the average molecular weight of the polyoxyethylene/polyoxypropylene copolymer is 7,680 to 9,510 Daltons, such as about or at 8,400-8,800 Daltons. In the LCMF poloxamer, the percentage of high molecular weight components with a molecular weight of greater than or equal to 13,000 Daltons constitute less 1% of the total distribution of components of the poloxamer preparation; such preparation does not, when administered to a subject, result in a component with the longer half-life. In some embodiments, the percentage of high molecular weight components in the preparation greater than 13,000 Daltons constitutes less than 0.9%, 0.8%, 0.7%, 0.6%, 0.5% or less of the total distribution of components of the poloxamer preparation, and, when administered, does not result in a component with the longer half-life. For all embodiments of the method herein, including the LCMF poloxamer, such as the LCMF P188, as well as the compositions and uses, the poloxamer can have a polydispersity value of the polyoxyethylene/polyoxypropylene copolymer that is less than 1.06, 1.05, 1.04, 1.03 or less.

The LCMF poloxamer can be an LCMF P188 poloxamer, which can be produced by any suitable methods, including a method described herein, and detailed below that includes the steps of: a) introducing a poloxamer 188 solution into a suitable vessel, such as an extractor vessel, where the poloxamer is dissolved in a first alkanol to form a solution; b) contacting the poloxamer solution with an extraction solvent comprising a second alkanol and supercritical carbon dioxide under a temperature and pressure to maintain the supercritical carbon dioxide for a first defined period, where: the temperature is above the critical temperature of carbon dioxide but is no more than 40° C.; the pressure is 220 bars to 280 bars; and the alkanol is provided at an alkanol concentration that is 7% to 8% by weight of the total extraction solvent; c) increasing the concentration of the second alkanol in step b) in the extraction solvent a plurality of times in gradient steps over time of the extraction method, wherein, each plurality of times occurs for a further defined period; and in each successive step, the alkanol concentration is increased 1-2% compared to the previous concentration of the second alkanol; and d) removing the extraction solvent from the vessel, such as an extractor vessel, to thereby remove the extracted material from the raffinate poloxamer preparation.

The compositions are formulated for use to provide doses that typically range from about or at 100 mg/kg-675 mg/mg, including 100 mg/kg-500 mg/kg, such as 400 or 450 to 500 mg/kg. In certain embodiments, the composition is formulated for the first infusion to deliver least or about at least 100 mg/kg, such as 100 mg/kg-675 mg/mg, including 100 mg/kg-500 mg/kg, such as 400 or 450 to 500 mg/kg. In some embodiments, the compositions are formulated so that copolymer in each infusion is from or from about 200 mg/kg to 450 mg/kg. The concentration of the copolymer in the composition for each infusion can be at least 10.0 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 115 mg/mL, at least 130 mg/mL, at least 150 mg/mL, at least 200 mg/mL or at least 225 mg/mL, such as no more than 225 mg/mL. Exemplary ranges of the concentration of copolymer that is administered in each infusion is from or from about 150 mg/mL to 225 mg/mL. A typical volume of the composition for each infusion is, for example, a volume that is 0.4 mL/kg to 3.0 mL/kg of the subject. The composition can be formulated so that the infusion can last up to 24 hours, such as from 1 to 24 hours, less than 24 hours, including for example, 2-10 hour, or 2-6 hours or 4-12 hours. The compositions for use are formulated so that only a single infusion is required, or the infusion is repeated 1 week or more than 1 week up to 4 weeks following completion of the prior dose. For example, the composition for infusion is formulated so that it is repeated at least 7 days, 8 days, 9 days, 10 days, 11 days, 13 days or 14 days, 3 weeks or 4 weeks following completion of the prior dose. The dosage of the composition for infusion can be the same as a prior dosage or different. The treatment can be continued for a at least 1 week, 3 weeks, 1 month, 2 months, 3 months, 4 months, 5 months, 6 months, 7 months, 8 months, 9 months, 10 months, 11 months, a year or more.

The subject for whom the compositions are formulated are as described above for the methods, and can have acute heart failure, such as, for example, acute decompensation. The subject treated can have chronic heart failure. The subject treated can have coronary artery disease, myocardial infarction or hypertension.

The compositions can be formulated with or provided as a combination or kit with second agent or treatment for treating heart failure. The agent can be formulated for use with the copolymer composition or in a separate composition for administration, intermittently with the infusion, before an infusion or the first infusion, simultaneously with the infusion or other suitable regimen. Exemplary second agents include, but are not limited to, a diuretic, loop diuretic, a potassium sparing agent, a vasodilator, an ACE inhibitor, ARBs (angiotensin receptor blockers), an angiotensin II antagonist, Aldosterone antagonist, a positive inotrophic agent, a phosphodiesterase inhibitor, a beta-adrenergic receptor antagonist, a calcium channel blocker, a nitrate, an alpha blocker, a central alpha antagonist, a statin, a cardiac glycoside, Digoxin, Nitrates, chlorthalidone, amlodipine, lisinopril, doxazosin, and a combination of these agents. Treatment can include other types of treatment, such as provision of an implantable pacemakers, a defibrillator, and/or left ventricular assist device (LVAD). The heart failure can be systolic heart failure, such as systolic heart failure that is manifested by left ventricular (LV) ejection fraction (EF) is less than or equal to 40% or about 40%.

The copolymer in the composition for use can be formulated for administration of a dosage that is at least or about at least 100 mg/kg, such as, for example, from or from about 100 mg/kg to 675 mg/kg, or from or from about 200 mg/kg to 450 mg/kg. For example, copolymer can be formulated in the composition at a concentration for single dosage administration that is at least 10.0 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 115 mg/mL, at least 130 mg/mL, at least 150 mg/mL, at least 200 mg/mL or at least 225 mg/mL, such as a concentration for single dosage administration that is no more than 225 mg/mL, such as where the copolymer is formulated at a concentration for single dosage administration that is from or from about 150 mg/mL to 225 mg/mL. The composition can be formulated for administration of a volume that is 0.4 mL/kg to 3.0 mL/kg, and/or such that the copolymer is formulated for infusion to the subject for a time period of less than 24 hours, less than 12 hours, less than 6 hours, less then 3 hours or a time period of 1 to 24 hours, or 2-6 hours or 1-12 hours, or 3-5 hours or 4 hours to 12 hours. The composition containing the copolymer can be formulated so that it can be administered only once, or repeated 1 week to 4 weeks following completion of the prior dose, such as at least 7 days, 8 days, 9 days, 10 days, 11 days, 13 days or 14 days following completion of the prior dose. As noted, the composition can be for treatment of acute heart failure.

Among the uses of the compositions is treatment of acute decompensation and for treatment of chronic heart failure. For example, composition is used for treatment of coronary artery disease, myocardial infarction or hypertension. For all conditions, the composition is formulated to be administered only once, or for administration once followed by additional infusions after a least a week or more than a week, generally up to 3 or 4 weeks after a prior infusion. The compositions can contain the copolymer with a second agent for treating heart failure, or each can be provided as separate composition in a combination or kit. As with the methods, the second agent, for example, can be a diuretic, loop diuretic, a potassium sparing agent, a vasodilator, an ACE inhibitor, ARBs (angiotensin receptor blockers), an angiotensin II antagonist, Aldosterone antagonist, a positive ionotrophic agent, a phosphodiesterase inhibitor, a beta-adrenergic receptor antagonist, a calcium channel blocker, a nitrate, an alpha blocker, a central alpha antagonist, a statin, a cardiac glycoside, Digoxin, Nitrates, chlorthalidone, amlodipine, lisinopril, doxazosin, and a combination of these agents.

The composition is used for infusion only one time to effect treatment. In other embodiments, the composition containing the copolymer can be administered in a regimen in which after one week or at least one week, the infusion of the copolymer is repeated at least one more time. The intervals between infusions can be the same or different, can be at least a week up to 3 or 4 weeks, or the interval can be increased by at least 1 week, whereby a third infusion is administered at 4-5 weeks after the second infusion or the interval can be increased by at least 1 week, whereby a third infusion is administered at 5-6 weeks after the second infusion.

The compositions for use for treatment are formulated so that the infusion(s) is completed in less than 24 hours, such as less than 12 hours, less than 6 hours, less than 3 hours, including for example, 2-6 hours.

For the methods and compositions for use and compositions the second infusion of the copolymer can be administered 7 days-28 days after the first dose; if a third and subsequent infusions are administered, the third and any subsequent infusion are administered 21-42 days after the prior infusion. For all of the compositions, uses thereof and methods, for each infusion, the gravimetric dose of the copolymer can be the same or different. The status of the condition patient's heart can be assessed and the dose is adjusted as needed.

BRIEF DESCRIPTION OF THE DRAWINGS

The drawings described herein are for illustrative purposes only of selected embodiments and not all possible implementations, and are not intended to limit the scope of the present disclosure.

FIG. 5 shows one embodiment of the cross section of stainless spheres of different sizes in a solvent distribution bed.

FIG. 9 shows a Reverse Phase High Performance Liquid Chromatography (RP-HPLC) chromatogram comparing profiles of compositions of 15% LCMF 188 with 15% P188 (available under the trademark Flocor®), relative to other poloxamers and polymers (of different hydrophobicity/hydrophilicity) showing that the LCMF188 is more hydrophilic than the P188.

FIG. 10 shows a RP-HPLC chromatogram comparing different lots of LCMF poloxamer 188 with purified poloxamer 188 confirming the difference in hydrophilicity.

FIGS. 11A-B Depict the protocol for the study assessing the effects of repeat administration of the Poloxamer 188. Details are set forth in Example 6.

FIGS. 12A-F Depict the results, described in Example 6, of the study.

DETAILED DESCRIPTION

Figure 1:
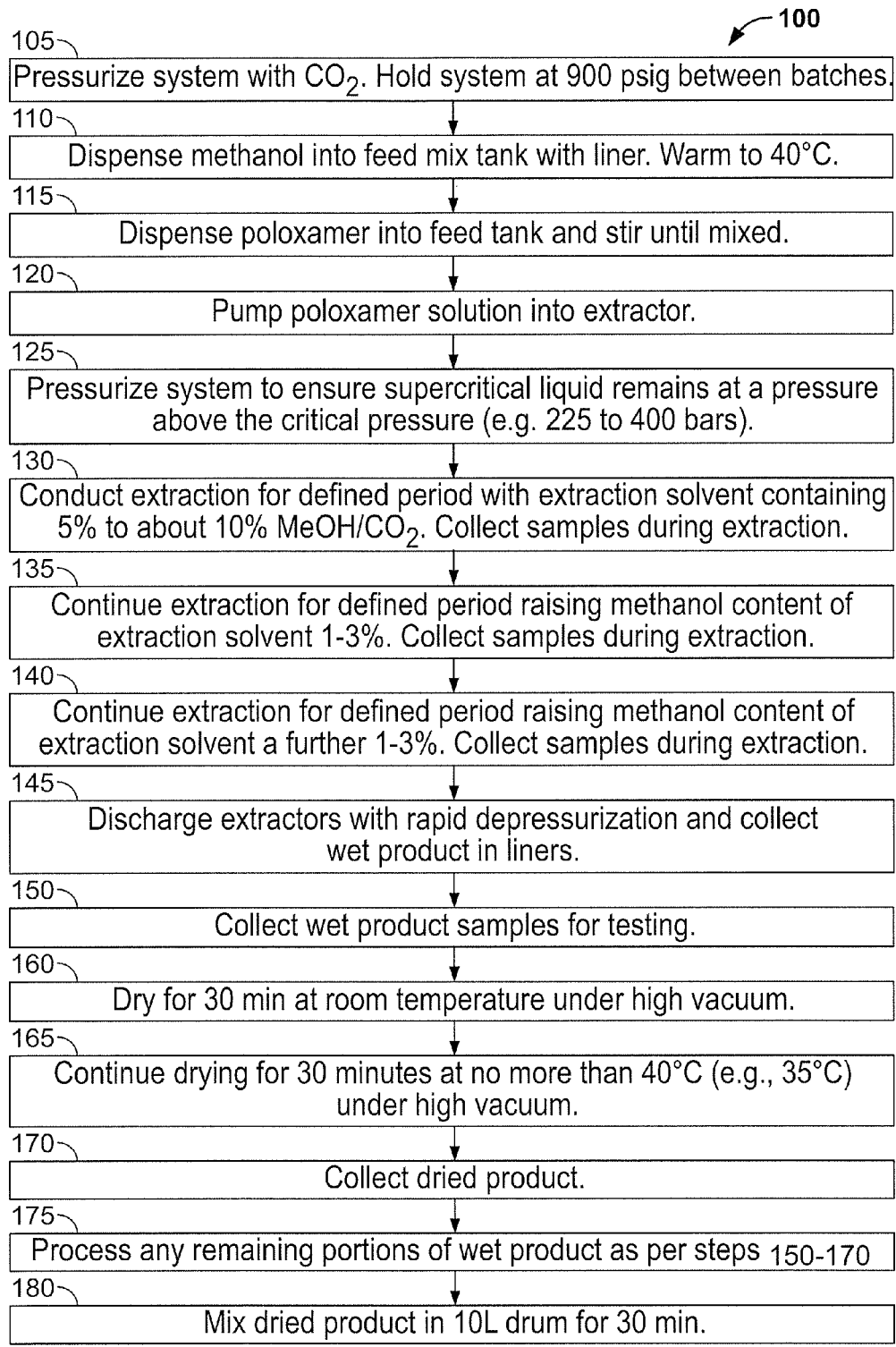
FIG. 1 is a general process 100 for supercritical fluid extraction (SFE) of a poloxamer.

Outline
  A. Definitions
  B. Heart Failure and Cytoprotective Activity of Poloxamer 188
    1. Heart Failure
    2. Cytoprotective Activity of Poloxamer 188 Against Heart Failure
    3. Single Infusion Therapy of Poloxamer 188
    4. Multiple infusions of P-188
  C. POLOXAMERS AND PURIFIED POLOXAMERS
    1. Poloxamer 188 (P-188)
    2. Molecular Diversity of Poloxamer 188
      a. Low Molecular Weight Components
      b. Components Resulting in Long Circulating Half-Life
    3. Long Circulating Material Free (LCMF) Poloxamer
    4. Extraction Method For Purifying Poloxamers
      a. Processes For Extraction
        i. Supercritical Methods
        ii. High Pressure Methods
      b. Extraction Vessel and System
      c. Extraction and Removal of Extractants d. Exemplary Methods for Preparation of Purified Poloxamers
   i. Removal of Low Molecular Weight (LMW) Components
   ii. Preparation of Long Circulating Material Free (LCMF) Poloxamer
   iii. Methods for Confirming the Identity of LCMF Poloxamers
D. Pharmaceutical Compositions, Dosages and Administration
E. Methods of Assessing Heart Function and Activity of Poloxamer Treatment or Monitoring Therapies
F. Methods Of Treatment and Therapeutic Uses
G. Combination Therapies
H. Examples A. Definitions Unless defined otherwise, all technical and scientific terms used herein have the same meaning as is commonly understood by one of skill in the art to which the invention(s) belong. All patents, patent applications, published applications and publications, Genbank sequences, databases, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it understood that such identifiers can change and particular information on the internet can come and go, but equivalent information can be found by searching the internet. Reference thereto evidences the availability and public dissemination of such information.

As used herein, poloxamers are synthetic block copolymers of ethylene oxide and propylene oxide. A "polyoxyethylene/polyoxypropylene copolymer," "PPC" or "poloxamer" refers to a block copolymer containing a central block of polyoxypropylene (POP) flanked on both sides by blocks of polyoxyethylene (POE) having the following chemical formula:

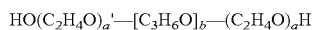

where: a' and a can be the same or different and each is an integer such that the hydrophile portion represented by ($C_2H_4O$) (i.e. the polyoxyethylene portion of the copolymer) constitutes approximately 60% to 90% by weight of the copolymer, such as 70% to 90% by weight of the copolymer; and b is an integer such that the hydrophobe represented by ($C_3H_6O)_b$ (i.e. the polyoxypropylene portion of the copolymer) has a molecular weight of approximately 950 to 4,000 Daltons (Da), such as about 1,200 to 3,500 Da, for example, 1,200 to 2,300 Da, 1,500 to 2,100 Da, 1,400 to 2,000 Da or 1,700 to 1,900 Da. For example, the molecular weight of the hydrophile portion can be between 5,000 and 15,000 Da. Exemplary poloxamers having the general formula described above include poloxamers wherein a or a' is an integer 5-150 and b is an integer 15-75, such as poloxamers wherein a is an integer 70-105 and b is an integer 15-75. Poloxamers include poloxamer 188 (e.g., those sold under the trademarks Pluronic F-68, Flocor®, Kolliphor® and Lutrol®).

The nomenclature of the polyoxyethylene/polyoxypropylene copolymer relates to its monomeric composition. The first two digits of a poloxamer number, multiplied by 100, gives the approximate molecular weight of the hydrophobic polyoxypropylene block. The last digit, multiplied by 10, gives the approximate weight percent of the hydrophilic polyoxyethylene content. For example, poloxamer 188 describes a polymer containing a polyoxypropylene hydrophobe of about 1,800 Da with a hydrophilic polyoxyethylene block content of about 80% of the total molecular weight.

Poloxamers can be synthesized in two steps, first by building the polyoxypropylene core, and then by addition of polyoxyethylene to the terminal ends of the polyoxypropylene core. Because of variation in the rates of polymerization during both steps, a poloxamer can contain heterogeneous polymer species of varying molecular weights. The distribution of polymer species can be characterized using standard techniques including, but not limited to, gel permeation chromatography (GPC).

As used herein, Poloxamer 188 (also called P-188 or P188) refers to a polyoxyethylene/polyoxypropylene copolymer that has the following chemical formula:

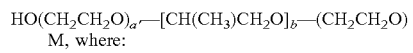
M, where:

a' and a can be the same or different and each is an integer such that the hydrophile portion represented by ($C_2H_4O$) (i.e. the polyoxyethylene portion of the copolymer) constitutes approximately 60% to 90%, such as approximately 80% or 81%; and b is an integer such that the hydrophobe represented by ($C_3H_6O$) has a molecular weight of approximately 1,300 to 2,300 Da, such as 1,400 to 2,000 Da, for example approximately 1,750 Da. For example, a is about 79 and b is approximately or is 28. The average total molecular weight of the compound is approximately 7,680 to 9,510 Da, such as generally 8,400-8,800 Da, for example about or at 8,400 Da. Poloxamer 188 is a preparation that can contain a heterogeneous distribution of polymer species that primarily vary in overall chain length of the polymer, but also include truncated polymer chains with unsaturation, and certain low molecular weight glycols. Included among poloxamer 188 molecules are those that exhibit a species profile (e.g., determined by GPC) containing a main peak and "shoulder" peaks on both sides representing low molecular weight (LMW) polymer species and high molecular weight (HMW) polymer species. Poloxamer 188 also refers to materials that are purified to remove or reduce species other than the main component.

As used herein, "main component" or "main peak" with reference to a poloxamer 188 preparation refers to the species of copolymer molecules that have a molecular weight of less than about 13,000 Da and greater than about 4,500 Da, with an average molecular weight of between about 7,680 to 9,510 Da, such as generally 8,400-8,800 Da, for example about or at 8,400 Da. Main peak species include those that elute by gel permeation chromatography (GPC) at between 14 and 15 minutes depending on the chromatography conditions (see U.S. Pat. No. 5,696,298).

As used herein, "low molecular weight" or "LMW" with reference to species or components of a poloxamer 188 preparation refers to components that have a molecular weight generally less than 4,500 Da. LMW species include those that elute by gel permeation chromatography (GPC) after 15 minutes depending on the chromatography conditions. (see U.S. Pat. No. 5,696,298). Such impurities can include low molecular weight poloxamers, poloxamer degradation products (including alcohols, aldehydes, ketones, and hydroperoxides), diblock copolymers, unsaturated polymers, and oligomeric glycols including oligo(ethylene glycol) and oligo(propylene glycol).

As used herein, "high molecular weight" or "HMW" with reference to species or components of a poloxamer 188 preparation refers to components that have a molecular weight generally greater than 13,000 Da, such as greater than 14,000 Da, greater than 15,000 Da, greater than 16,000 Da or greater. HMW species include those that elute by gel permeation chromatography (GPC) at between 13 and 14 minutes depending on the chromatography conditions (see U.S. Pat. No. 5,696,298).

As used herein, "polydispersity" or "Đ" refers to the breadth of the molecular weight distribution of a polymer composition. A monodisperse sample is defined as one in which all molecules are identical. In such a case, the polydispersity (Mw/Mn) is 1. Narrow molecular weight standards have a value of Đ near 1 and a typical polymer has a range of 2 to 5. Some polymers have a polydispersity in excess of 20. Hence, a high polydispersity value indicates a wide variation in size for the population of molecules in a given preparation, while a lower polydispersity value indicates less variation. Methods for assessing polydispersity are known in the art, and include methods as described in U.S. Pat. No. 5,696,298. For example, polydispersity can be determined from chromatograms. It is understood that polydispersity values can vary depending on the particular chromatogram conditions, the molecular weight standards and the size exclusion characteristics of gel permeation columns employed. For purposes herein, reference to polydispersity is as employed in U.S. Pat. No. 5,696,298, as determined from chromatograms obtained using a Model 600E Powerline chromatographic system equipped with a column heater module, a Model 410 refractive index detector, Maxima 820 software package (all from Waters, Div. of Millipore, Milford, Mass.), two LiChrogel PS-40 columns and a LiChrogel PS-20 column in series (EM Science, Gibbstown, N.J.), and polyethylene glycol molecular weight standards (Polymer Laboratories, Inc., Amherst, Mass.). It is within the level of a skilled artisan to convert any polydispersity value that is obtained using a different separation method to the values described herein simply by running a single sample on both systems and then comparing the polydispersity values from each chromatogram.

As used herein, "purified poloxamer 188" or "P188-P" or "purified long circulating material (LCM)-containing poloxamer 188" refers to a poloxamer 188 that has polydispersity value of the poloxamer of less than or about 1.07, such as less than or 1.05 or less than or 1.03, and is a purified poloxamer 188 that has a reduced amount low molecular weight components, but contains the long circulating material. A poloxamer 188 in which "low molecular weight material has been removed" or "low molecular weight material has been reduced," or similar variations thereof, refers to a purified poloxamer 188 in which there is a distribution of low molecular weight components of no more than or less than 3.0%, and generally no more than or less than 2.0% or no more than or less than 1.5% of the total distribution of components. Typically, such a poloxamer 188 exhibits reduced toxicity compared to forms of poloxamer 188 that contain a higher or greater percentage of low molecular weight components. The poloxamer 188 is purified to remove or reduce low molecular weight components. Commercially available and prior preparations of poloxamer, such as poloxamer 188, have a long circulating material (LCM) that, when administered to a human, has a half-life that is more than 5.0 fold the circulating half-life of the main component in the distribution of the copolymer.

An exemplary purified LCM-containing poloxamer 188 is poloxamer 188 available under the trademark FLOCOR® (see, also U.S. Pat. No. 5,696,298, which describes LCM-containing poloxamer 188). When the purified LCM-containing poloxamer 188 is administered as an intravenous injection to a human or an animal, GPC analysis of blood obtained from the treated subject exhibits two circulating peaks: a peak designated the main peak that comprises the main component of the polymeric distribution and a peak of higher molecular weight, compared to the main peak, that exhibits a substantially slower rate of clearance (more than 5-fold slower than the main peak, typically more than 30 hours and as much as 70 hours, as shown herein) from the circulation, i.e., a long circulating material (LCM).

As used herein, long circulating material (LCM) refers to material in prior poloxamer preparations that, upon administration to a subject, have a half-life in the subject, such as a human, that is substantially longer than the half-life of the main component of the poloxamer preparation. When administered to a human subject the LCM material in a poloxamer preparation has more than about or more than 5-fold the half life of the main component of the poloxamer preparation. The LCMF poloxamers as provided herein do not give rise to such long circulating material. There is no component that has a half-life that it 5-fold longer than the main component. For comparing poloxamers, components of corresponding poloxamers are compared, where a corresponding poloxamers have the same formula. For example, an LCMF poloxamer 188 is compared to a poloxamer 188.

As used herein, "long circulating material free" or "LCMF" with reference to poloxamer 188 refers to a purified poloxamer 188 preparation that has a reduced amount of low molecular weight components, as described above for purified poloxamer 188, and that, following intravenous administration to a subject, the components of the polymeric distribution clear from the circulation in a more homogeneous manner such that any long circulating material exhibits a half-life (in human subjects) that is no more than 5-fold longer than the circulating half-life ($t_{1/2}$) of the main peak. Thus, an LCMF is a poloxamer 188 that does not contain components, such as a high molecular weight components or low molecular weight components as described herein, that are or gives rise to a circulating material with a $t_{1/2}$ that, when administered to a human subject, is more than 5.0-fold greater than the $t_{1/2}$ of the main component, and generally no more than 4.0, 3.0, 2.0 or 1.5 fold greater than the half-life of the main component in the distribution of the copolymer. Typically, an LCMF poloxamer is a poloxamer in which all of the components of the polymeric distribution clear from the circulation at a more homogeneous rate.

As used herein, "distribution of copolymer" refers to the molecular weight distributions of the polymeric molecules in a poloxamer preparation. The distribution of molecular masses can be determined by various techniques known to a skilled artisan, including but not limited to, colligative property measurements, light scattering techniques, viscometry and size exclusion chromatography. In particular, gel permeation chromatography (GPC) methods can be employed that determine molecular weight distribution based on the polymer's hydrodynamic volume. The distribution of molecular weight or mass of a polymer can be summarized by polydispersity. For example, the greater the disparity of molecular weight distributions in a poloxamer, the higher the polydispersity.

As used herein, half-life, biological half-life, plasma half-life terminal half-life, elimination half-life or $t_{1/2}$ refer to the time that a living body requires to eliminate one half of the quantity of an administered substance through its normal channels of elimination. The normal channels of elimination generally include the body's cleansing through the function of kidneys and liver in addition to excretion functions to eliminate a substance from the body. Half-life can be described as the time it takes the blood plasma concentration of a substance to halve its steady state level, i.e. the plasma half-life. A half-life can be determined by giving a single dose of drug, usually intravenously, and then the concentration of the drug in the plasma is measured at regular intervals. The concentration of the drug will reach a peak value in the plasma and will fall as the drug is broken down and cleared from the blood. As used herein "Cmax" refers to the peak or maximal plasma concentration of a drug after administration.

As used herein, the "concentration of a drug at steady state" or "Css" refers to the concentration of drug at which the rate of drug elimination and drug administration are equal. It is achieved generally following the last of an infinite number of equal doses given at equal intervals. The time required to achieve a steady state concentration depends on the half-life of the drug. The shorter the half-life, the more rapidly steady state is reached. Typically it takes 3-5 half-lives to accumulate to greater than 90% of the final steady state concentrations.

As used herein, "impurities" refer to unwanted components in a poloxamer preparation. Typically impurities include LMW components less than 4,500 Daltons and high molecular weight components greater than 13,000 Daltons.

As used herein, "remove or reduce" with reference to a poloxamer component in a preparation refers to decreasing the weight percentage of the component in the poloxamer preparation relative to the initial percentage of the component. Generally, a poloxamer component is removed or reduced if the percentage by weight of the component to the total distribution of components is decreased by at least 1%, and typically at least 2%, 3%, 4%, 5%, or more. For example, most commercial preparations of a poloxamer 188 contain a LMW component (less than 4,500 Daltons) that is about 4% by weight of the total components in the distribution. The LMW component is reduced in a purified product if there is less than 3% by weight of the component, such as less than 2% or 1%.

As used herein, "solvent" refers to any liquid in which a solute is dissolved to form a solution.

As used herein, a "polar solvent" refers to a solvent in whose molecules there is either a permanent separation of positive and negative charges, or the centers of positive and negative charges do not coincide. These solvents have high dielectric constants, are chemically active, and form coordinate covalent bonds. Examples of polar solvents are alcohols and ketones.

As used herein, "feed" refers to a solute dissolved in a solvent.

As used herein, an "extraction solvent" refers to any liquid or supercritical fluid that can be used to solubilize undesirable materials that are contained in a poloxamer preparation. It is a solvent that can effect solvent extraction to separate a substance from one or more others based on variations in the solubilities. Generally an extraction solvent is immiscible or partially miscible with the solvent in which the substance of interest is dissolved. For example, an extraction solvent is one that does not mix or only partially mixes with a first solvent in which the substance of interest is dissolved, so that, when undisturbed, two separate layers form. Exemplary extraction solvents are supercritical liquids or high pressure liquids.

As used herein, the terms "supercritical liquid" and "supercritical fluid" include any compound, such as a gas, in a state above its critical temperature ($T_c$; i.e. the temperature, characteristic of the compound, above which it is not possible to liquefy the compound) and critical pressure ($p_c$; i.e., the minimum pressure which would suffice to liquefy the compound at its critical temperature). In this state, distinct liquid and gas phases typically do not exist. A supercritical liquid typically exhibits changes in solvent density with small changes in pressure, temperature, or the presence of a co-modifier solvent.

As used herein, "supercritical carbon dioxide" refers to a fluid state of carbon dioxide where it is held at or is above its critical temperature (about 31° C.) and critical pressure (about 74 bars). Below its critical temperature and critical pressure, carbon dioxide usually behaves as a gas in air or as a solid, dry ice, when frozen. At a temperature that is above 31° C. and a pressure above 74 bars, carbon dioxide adopts properties midway between a gas and a liquid, so that it expands to fill its container like a gas but with a density like that of a liquid.

As used herein, "critical temperature" or "critical point" refers to the temperature that denotes the vapor-liquid critical point, above which distinct liquid and gas phases do not exist. Thus, it is the temperature at and above which vapor of the substance cannot be liquified no matter how much pressure is applied. For example, the critical temperature of carbon dioxide is about 31° C.

As used herein, "critical pressure" refers to the pressure required to liquefy a gas at its critical temperature. For example, the critical pressure of carbon dioxide is about 74 bars.

As used herein, the term "high pressure liquid" includes a liquid formed by pressurizing a compressible gas into the liquid at room temperature or a higher temperature.

As used herein, a "co-modifier solvent" refers to a polar organic solvent that increases the solvent strength of an extraction solvent (e.g., supercritical fluid carbon dioxide). It can interact strongly with the solute and thereby substantially increase the solubility of the solute in the extraction solvent. Examples of co-modifier solvents include alkanols. Typically between 5% and 15% by weight of co-modified solvent can be used.

As used herein, the term "alkanol" includes simple aliphatic organic alcohols. In general, the alcohols intended for use in the methods provided herein include six or fewer carbon atoms (i.e., $C_1$-$C_6$ alkanols). The alkane portion of the alkanol can be branched or unbranched. Examples of alkanols include, but are not limited to, methanol, ethanol, isopropyl alcohol (2-propanol), and tert-butyl alcohol.

As used herein, "subcritical extraction" refers to processes using a fluid substances that would usually be gaseous at normal temperatures and pressures that are converted to liquids at higher pressures and lower temperatures. The pressures or temperatures are then normalized and the extracting material is vaporized leaving the extract. Extractant can be recycled.

As used herein, "extraction vessel" or "extractor" refers to a high-pressure vessel that is capable of withstanding pressures of up to 10,000 psig and temperatures of up to 200° C. The volume of the vessels can range from 2 mL to 5,000 L or larger, and generally is 1 L to 1,000 L, such as 5 L to 500 L. Extraction vessels generally are made out of stainless steel. Such devices are well known to a skilled artisan and available commercially.

As used herein, "isocratic" refers to a system in which an extraction solvent is used at a constant or near constant concentration.

As used herein, "gradient" or "gradient steps" refers to a system in which two or more extraction solvents are used that differ in their composition of components, typically by changes in concentration of one or more components. For example, the concentration of the alkanol solvent (e.g., methanol) is successively increased during the course of the extraction. Thus, the extraction solvent does not remain constant.

As used herein, "plurality" refers to a number of iterations of a process or step, A plurality is 2 or more. The number of repeats can be 2, 3, 4, 5, 6 or more.

As used herein, "extracted material" refers to the product containing the removed materials.

As used herein, "raffinate" refers to a product which has had a component or components reduced or removed. For example, the purified poloxamer in which extracted material has been removed.

As used herein, "batch method" or "batch extraction" refers to a process of extracting the solute from one immiscible layer by shaking the two layers until equilibrium is attained, after which the layers are allowed to settle before sampling. For example, a batch extraction can be performed by mixing the solute with a batch of extracting solvent. The solute distributes between the two phases. Once equilibrium is achieved, the mixing is stopped and the extract and raffinate phases are allowed to separate. In this method, the spent solvent can be stripped and recycled by distillation or fresh solvent can be added continuously from a reservoir.

As used herein, a "continuous method" or "continuous extraction" refers to a process in which there is a continuous flow of immiscible solvent through the solution or a continuous countercurrent flow of both phases. For example, a continuous extracting solvent is mixed with the solute. The emulsion produced in the mixer is fed into a settler unit where phase separation takes place and continuous raffinate and extract streams are obtained.

As used herein, "heart failure" refers to an abnormality of cardiac structure or function leading to failure of the heart to deliver oxygen at a rate commensurate with the requirements of the metabolizing tissues, despite normal filling pressure. The underlying cause of heart failure can be due to systolic ventricular dysfunction or abnormalities of ventricular diastolic function.

As used herein, the term "signs and symptoms of heart disease" or "signs and symptoms of heart failure" refers to signs and symptoms associated with heart failure as recognized by simple observation or by standard clinical tests. This, when combined with an individual's age and family history of heart disease, can lead to diagnosis of heart disease or heart failure. Examples of signs of heart disease include, but are not limited to, dyspnea, chest pain (angina), palpitations, syncope, edema, cyanosis and fatigue. Among these are those that can be subject to quantitative analysis, such as palpitations, cyanosis and others. Other symptoms include discomfort or pressure in the chest, radiating discomfort to the back, jaw, throat or arm, fullness or ingestion, sweating, nausea, vomiting, dizziness, weakness or shortness of breath and/or rapid or irregular heartbeats It is within the level of a skilled artisan, such as a treating physician, to identify a sign or symptom of heart disease.

As used herein, "acute decompensated heart failure" or "ADHF" refers to a worsening of the symptoms, typically shortness of breath (dyspnea), edema and fatigue, in a subject with existing heart disease. Typically, the symptoms require hospitalization.

As used herein, "left ventricular ejection fraction" or "LVEF" refers to the amount or percentage of blood pumped out of the total amount of blood in the left ventricle per beat. Thus, it is the percentage of blood pumped out of a filled left ventricle with each heartbeat. Generally, an LVEF>55% is normal, and lower than 50% is reduced. A skilled artisan is familiar with methods to assess or measure LVEF. Exemplary methods to measure EF include, but are not limited to, echocardiogram, cardiac catheterization, magnetic resonance imaging (MRI), computerized topography (CT) or nuclear medicine scan. EF can be measured as the stroke volume divided by end-diastolic volume.

As used herein, "diastole" refers to the cycle of heart pumping when the left ventricle fills with blood. The filling phase occurs when the heart muscle relaxes, allowing blood to enter and fill the left ventricle.

As used herein, "systole" refers to the cycle of heart pumping when the blood is forced out and the blood is emptied from the heart. The emptying phase occurs when the heart muscle contracts or squeezes to pump out or eject blood.

As used herein, "stroke volume" refers to the volume of blood pumped from one ventricle of the heart with each beat. Stroke volume is calculated as the end-diastolic volume minus the end-systolic volume.

As used herein, "end-diastolic volume" or "EDV" refers to the volume of blood in the ventricle at end load or filling in (i.e. diastole). Hence, it is the volume of blood just prior to the beat.

As used herein, "end-systolic volume" or "ESV" refers to the volume of blood in a ventricle at the end of contraction (i.e. systole) and the beginning of filling (i.e. diastole). Hence, it is the volume of the blood in the ventricle at the end of a beat.

ESV can be used to clinically measure systolic function. Methods of assessing or measuring ESV are well known to a skilled artisan and include, but are not limited to, an electrocardiogram (the end of the T wave), echocardiography, MRI or CT.

As used herein "systolic ventricular dysfunction" or "systolic heart failure" refers to reduced contraction and emptying of the left ventricle. It occurs when the hearts left ventricle does not pump enough blood out into the body on each beat. Systolic heart failure is characterized by a reduced ejection fraction. Hence, systolic heart failure also is classified as heart failure with reduced ejection fraction.

As used herein, "reduced ejection fraction," "heart failure with reduced ejection fraction" or "HFREF" refers to an ejection fraction of less than or equal to 50%, and generally less than or equal to 40%.

As used herein, "diastolic ventricular dysfunction" or "diastolic heart failure" refers to abnormal heart relaxation and filling of the left ventricle. It occurs when the heart does not relax properly so that the heart is not able to fill with blood. Diastolic heart failure is characterized by a preserved ejection fraction, and hence also can be classified as heart failure with preserved ejection fraction.

As used herein, "preserved ejection fraction," or "heart failure with preserved ejection fraction" or "HFPEF" refers to an ejection fraction of greater than or equal to 50%.

As used herein, "diseases and conditions associated with heart failure" refers to any condition associated with signs or symptoms of heart failure and that is confirmed by a diagnostic test of heart failure. Signs, symptoms and diagnostic tests for heart failure are well known to a skilled artisan. Symptoms of heart failure include, but are not limited to, breathlessness, ankle swelling or fatigue. Signs of heart failure include, but are not limited to, elevated jugular venous pressure, pulmonary crackles and displaced apex beat. Diagnostic tests for heart failure include, but are not limited to, abnormalities in the ability of heart to pump blood as determined by an electrocardiogram (EKG), an enlarged heart as determined by a chest x-ray, elevated levels of BNP in the blood, abnormal characteristics of heart size, shape, or blood flow as determined by an echocardiography (echo), abnormalities in pressure and blood flow in heart chambers as determined by cardiac catheterization, or abnormalities in blood flow as determined by coronary angiography. Exemplary of diseases and conditions associated with heart failure include, but are not limited to, ischemic heart disease (IHD; also called coronary heart disease), myocardial infarction, cardiomyopathy, high blood pressure, diseases of the heart valves, diseases of the pericardium, or arrhythmias.

As used herein the term "short term infusion(s)" means an intravenous infusion administered over a period of less than 24 hours.

As used herein, a "single infusion" refers to an infusion that provides an effective amount of a compound or pharmaceutical composition in only one infusion or administration.

As used herein, "pharmaceutical composition" includes a composition comprising a polyoxyethylene/polyoxypropylene copolymer described herein, such as an LCMF poloxamer, formulated as a pharmaceutically acceptable formulation and/or with one or more pharmaceutically acceptable excipients. In certain instances, the pharmaceutical composition comprises an aqueous injectable solution of the poloxamer buffered at a desired pH, such as 6-7 or 6 or about 6, with a suitable buffer. Exemplary of such buffers are any known to those of skill in the art to be biocompatible, such as citrate, including for example sodium citrate/citric acid. Suitable concentrations can be empirically determined, but typically range from 0.005 to 0.05 M, particularly about 0.01 M in an isotonic solution such as saline. In certain instances, pharmaceutical compositions useful in the methods herein are known to those of skill in the art for formulating poloxamer (see, e.g., Published International PCT Application No. WO 94/008596 and other such references and publications described herein).

As used herein, "treatment" refers to ameliorating or reducing symptoms associated with a disease or condition. Treatment means any manner in which the symptoms of a condition, disorder or disease are ameliorated or otherwise beneficially altered. Hence treatment encompasses prophylaxis, therapy and/or cure. Treatment also encompasses any pharmaceutical use of the compositions herein.

As used herein, "treating" a subject having a disease or condition means that a composition or other product provided or described herein is administered to the subject to thereby effect treatment thereof.

As used herein, amelioration of the symptoms of a particular disease or disorder by a treatment, such as by administration of a pharmaceutical composition or other therapeutic, refers to any lessening, whether permanent or temporary, lasting or transient, of the symptoms that can be attributed to or associated with administration of the composition or therapeutic.

As used herein, "prevention" or "prophylaxis" refers to methods in which the risk of developing disease or condition is reduced. Prophylaxis includes reduction in the risk of developing a disease or condition and/or a prevention of worsening of symptoms or progression of a disease, or reduction in the risk of worsening of symptoms or progression of a disease.

As used herein, an "effective amount" of a compound or pharmaceutical composition is an amount that is (a) sufficient to ameliorate, or in some manner how the subject feels, functions or survives (e.g., to reduce symptoms); (b) sufficient to achieve a desired physiological effect; and/or (c) sufficient to provide some other benefit; in each case, whether the improvement, effect or benefit is permanent, lasting, temporary, periodic, transitory or otherwise. Such amount can be administered as a single dosage or can be administered according to a dose schedule or regimen (e.g., repeat doses, continuous dosing), whereby it improves how the subject feels, functions or survives, and/or achieves a desired physiologic effect and/or provides other benefit.

As used herein, "subject" refers to any animal, regardless of class, order, family, genus or species (or any subcategory), such as, but not limited to: hominidae (such as humans); non-human primates (such as chimpanzees, gorillas and monkeys); rodentia (such as mice, rats, hamsters and gerbils); ruminants (such as goats, cows, deer, sheep); suidae (such as pigs); bovidae (such as bison); equus (such as horses); canidae (such as dogs); felidae (such as cats); in all cases, whether or not domesticated. Thus, a "subject" to be treated includes humans and non-human animals.

As used herein, a "combination" refers to any association between two or among more items. The association can be spatial, such as in a kit, or refer to the use of the two or more items for a common purpose.

As used herein, a "composition" refers to any mixture of two or more products or compounds. It can be a solution, a suspension, liquid, powder, a paste, aqueous or non-aqueous formulations or any combination thereof As used herein, an "article of manufacture" is a product that is made and sold. As used throughout this application, the term is intended to encompass modified protease polypeptides and nucleic acids contained in articles of packaging.

As used herein, "fluid" refers to any composition that can flow. Fluids thus encompass compositions that are in the form of semi-solids, pastes, solutions, aqueous mixtures, gels, lotions, creams and other such compositions.

As used herein, a "kit" refers to a packaged combination, optionally including reagents and other products and/or components for practicing methods using the elements of the combination. Kits optionally include instructions for use.

As used herein, the singular forms "a," "an" and "the" include plural referents unless the context clearly dictates otherwise.

As used herein, ranges and amounts can be expressed as "about" or "approximately" a particular value or range. About also includes the exact amount. Hence "about 0.05 mg/mL" means "about 0.05 mg/mL" and also "0.05 mg/mL."

As used herein, "optional" or "optionally" means that the subsequently described event or circumstance does or does not occur, and that the description includes instances where said event or circumstance occurs and instances where it does not. For example, an optionally substituted group means that the group is unsubstituted or is substituted.

As used herein "retention time" or $t_R$ means the time elapsed between the injection of a sample, such as an LCMF poloxamer 188 sample, onto a reverse phase column for reverse phase high performance liquid chromatography (RP-HPLC) and the peak response by the evaporative light scattering detector. The retention time is longer for more hydrophobic samples compared to less hydrophobic samples.

As used herein "capacity factor" or k' is determined by the following equation where $t_0$ is equal to the void time or the time a non retained substance passes through a reverse phase HPLC column (see Example 1 below):

$$k' = \frac{t_R - t_0}{t_0}.$$

LCM-containing purified poloxamer 188, such as the poloxamer sold under the trademark FLOCOR® has a mean retention time ($t_R$) of 9.883 and a k' of 3.697; whereas the LCMF poloxamer 188 has a mean retention time ($t_R$) of 8.897 and a mean k' of 3.202 (see Example 1)

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:1726).

B. Heart failure and cytoprotective activity of Poloxamer 188

Provided herein are methods of treating or ameliorating heart failure by administering to a subject that has heart failure a single short term infusion of a poloxamer, such as poloxamer 188 (P-188), for example any P-188 described herein. It is shown herein that the effects of the single short term infusion of P-188 persists for at least 168 hours (i.e. at least one week) and up to 3 weeks after the end of the infusion. The methods include repeat administration with a frequency of no more than once weekly. For example, administration of the poloxamer, such as P-188, can be repeated one or more times beginning at least one week after the end of the prior administration. Regimens include those in which the P-188 is administered 2 to 3 weeks after the first infusion, and then at increasing intervals between each infusion, such as, for example, administration of a third infusion at 4 to 6 weeks. In accord with the regimens, the initial infusion is typically at a dosage of or about 100-500 mg/kg, and generally 400 mg/kg to 500 mg/kg. The dosage can be the same or decreased with repeat administrations. Generally, the subject's heart function is monitored by standard methods, including any described or exemplified herein, throughout treatment. The dosage can be lowered as the subject's heart improves.

The methods provided herein can be used in the treatment of any disease or condition associated with heart failure, such as coronary artery disease, hypertension, myocardial infarction and other conditions associated with heart failure. In particular, the methods provided herein can be used in the treatment of subjects in which the left ventricular ejection fraction is below normal, such as subjects with systolic heart failure or in patients experiencing heart failure with preserved ejection fraction.

1. Heart Failure

Heart failure is caused by an impaired cardiac pump function that results in an inadequate systemic perfusion to meet the body's metabolic needs. Common causes of heart failure are related to conditions that weaken the heart muscle, thereby limiting blood from reaching the heart muscle and/or causing the heart to pump harder to keep blood circulating. For example, coronary artery disease, such as atherosclerosis, is associated with a build-up of cholesterol and fatty deposits in the heart's arteries, which limits blood from reaching heart muscles. Myocardial infarction, or heart attack, is associated with a block in arteries that supply blood to heart muscle, resulting in death of heart muscle tissue and weakening of the heart's ability to pump blood. Hypertension, or high blood pressure, causes the heart to pump harder to overcome increased resistance in order to achieve continued blood circulation, which causes the heart's chambers to enlarge and weaken.

Heart failure is generally divided into two types: systolic heart failure and diastolic heart failure. Systolic heart failure occurs when the heart fails to contract normally. The heart can take in blood but cannot fully pump out adequate blood due to weakened cardiac muscles. As a result, the volume of the blood pumping out to the whole body and lungs decreases and the heart, in particular the left ventricle, can become hypertrophic. On the other hand, diastolic heart failure occurs when the heart wall becomes too stiff to fill up the heart with blood. As a result, blood dams up in the left atrium and lung blood vessels, which could cause congestion.

A mechanism underlying cardiac muscle dysfunction in heart failure is abnormalities in cycling of calcium into myocytes, which regulates the ability of the heart to pump blood. Normally, calcium enters the cardiac myocyte from the outside through calcium channels, which triggers the release of calcium stored in the sarcoplasmic reticulum (SR) through calcium release channels called ryanodine receptors. The released calcium can bind to calcium-sensitive proteins that activate the interaction of actin and myosin in the myofilaments. The release of calcium triggers the heart to contract. Calcium is removed from the cytoplasm and back into the SR and also out through the plasma membrane, which shuts off contraction and initiates muscle relaxation. Impaired calcium release can cause decreased muscle contraction (systolic dysfunction) and defective calcium removal can hamper relaxation (diastolic dysfunction).

The body employs various compensatory mechanisms to assist a failing heart and overcome factors that otherwise can cause symptoms. The heart can enlarge or develop more mass (pathologic hypertrophy) or pump faster (chronotropic response), which initially can increase the heart's ability to pump blood. The body can respond by narrowing blood vessels (vasoconstriction), which maintains blood pressure and offsets the heart's loss of pumping power. This, however, also can put additional strain on the heart. The body also can divert blood away from less important tissues and organs to maintain flow to the heart and brain. Ultimately, if the underlying strain on the heart is not resolved, these compensatory mechanisms will exacerbate the underlying problem and begin to fail, also called decompensation.

Symptoms of heart failure include shortness of breath, persistent coughing or wheezing, edema (buildup of excess fluid if body tissues), fatigue, lack of appetite or nausea, impaired thinking and increased heart rate. Everyday activities such as walking, climbing stairs or carrying groceries can become difficult. When blood returning to the heart through veins backs-up due to the heart's decreased ability to pump blood, fluid can accumulate and cause congestion in the body's tissues, resulting in congestive heart failure. Fluid accumulation in the lungs results in pulmonary edema, which can interfere with breathing, including shortness of breath. Left untreated, pulmonary edema can cause respiratory distress. Patients with heart failure can die from end-organ failure resulting from inadequate systemic organ perfusion, progressive pump failure and congestion or sudden cardiac death.

2. Cytoprotective Activity of Poloxamer 188 Against Heart Failure

P-188, and particularly non-purified P-188, has been used to treat heart failure. P-188 has cytoprotective, rheologic and antithrombotic effects. In particular, P-188 is a cytoprotective agent based on its ability to bind to damaged membranes, and restore the cell's natural, hydrated non-adhesive surface. Cardiac stress in heart failure results in mechanical sheer stresses to the membrane of cardiac myocytes that can result in loss of membrane integrity. It is reported that P-188 can seal damaged membranes of cardiac muscle cells, and thereby protect the heart from ongoing cardiomyocyte loss. Pretreatment with P-188 has been shown to reverse the cardiac injury caused by lysophosphatidylcholine (LPC), which is an amphiphilic metabolite of phosphatidylcholine that incorporates into lipid bilayers to affect the physiochemical properties of the membrane and the enzymes and ion channels embedded in the membrane (Watanabe and Okada (2003) *Mol. Cell Biochem.*, 248:209-215).

When the heart is failing, there is a dysregulation in calcium cycling that can result in unregulated entry into the cell and calcium overload and/or an efflux or pouring out of calcium from the cells. High intracellular calcium in failing cardiomyocytes can activate calpains that cleave dystrophin, thereby resulting in membrane tears and a further rise in calcium. The ability of P-188 to seal up damaged areas limits the unregulated cycling of calcium. Thus, the heart can redirect its energy to keeping it beating instead of trying to compensate for or regulate the calcium concentration.

The effects of P-188, including effects for treating heart failure, however, are reported not to be long-lasting. Treatment regimens administer daily or more than daily doses for extended periods. P-188 is known to have a short plasma half-life of under 7.5 hours (Grindel et al. (2002) *Journal of Pharmaceutical Sciences*, 90:1936-1947 (Grindel et al. 2002a), and/or Grindel et al. (2002) *Biopharmaceutics & Drug Disposition*, 23:87-103 (Grindel et al. 2002b)). Following an administration of P-188, greater than 99% of the administered dose will have been cleared from the body after 7 half-lives or about 52-53 hours. Thus, it has been understood that the therapeutic benefit of P-188 results while the compound is circulating in the body and shortly thereafter, but that benefits decline after discontinuation of drug administration as the drug is cleared from the body and no new drug is administered. In one study assessing effects of P-188 on heart failure in a model of coronary microembolization-induced heart failure, up to a 5 hour benefit of P-188 was reported (Ilsar et al. (2010) *J. Am. Col. Cardiol.* 55(Suppl. 1): A16.E146). Indeed, a study in dogs, in which P-188 may have a longer half-life of 18 hours, no effect of acute administration of P-188 after one week was observed in left ventricular geometry or on troponin levels. This result was understood to be reasonable because one week is a sufficient time to wash out any P-188 remaining from an acute administration (Townsend et al. (2010) *J. Clin. Invest.*, 120:1140-1150).

This short plasma half-life is consistent with reports that chronic, repeat administration or continuous intravenous infusion is required and employed to maintain therapeutically relevant concentration of drug in the circulation. For example, a study in dystrophin deficient (mdx) mice, given an infusion of dobutamine to simulate acute heart failure, demonstrated that pretreatment with P-188 immediately conferred protection from dobutamine-induced heart failure (Yasuda et al. (2005) *Nature*, 436:1025-1029). While the long-term benefit was not assessed, the authors concluded that chronic intravascular administration of P-188 would be necessary due to the progressive nature of the disease. Consistent with these teachings, a study in a more severe model of heart disease in the golden retriever muscular dystrophy (GRMD) model found that chronic application of P-188 was highly effective in preventing cardiac injury (Townsend et al. (2010) *J. Clin. Invest.*, 120:1140-1150). In this model, animals were continually (24 hours/day) infused non-purified P-188 for 8 weeks, which resulted in no progression towards a dilated cardiac phenotype in contrast to non-treated animals. Thus, effective poloxamer therapy for the treatment of heart disease is reported to require chronic administrations, such as one or more times a day for days, weeks, months or more than a year (see e.g., published U.S. Application No. US 2008/0260681).

In contrast it is shown herein, that a single infusion can be sufficient to effect treatment or a single infusion followed by a further infusion at least a week later, and up to three weeks or four weeks later, or a series of infusions as described herein can effect treatment.

3. Single Infusion Therapy of Poloxamer 188

It is shown herein that a single short term infusion of P-188 confers durable benefits in heart failure that provide immediate benefits and last for at least one week and longer. Results provided herein demonstrate that a single, short infusion of a purified P-188 provides a benefit for at least 168 hours (i.e. at least one week) in key hemodynamic parameters (i.e. ejection fraction, stroke volume and cardiac output). Effects on biomarkers of cardiac function such as cardiac troponin-I (TnI) and N-terminal pro-brain natriuretic peptide (nt-pro BNP) show an even longer lasting effect suggesting that the treatment effects of P-188 persist for up to 3 weeks after a single short term infusion. These results are surprising in view of the short half-life of P-188 and the reported studies in the art, described above, that establish that continuous infusions or chronic administrations daily are required.

The results provided herein were observed following a single, short-term (about or 2 hours) infusion of purified P-188 in a well-established large-animal model of chronic heart failure produced by multiple sequential intracoronary microemobilizations. Left ventricular systolic and diastolic cardiac function were assessed. In particular, hemodynamic, ventriculographic, echocardiographic and electrocardiographic measurements were taken at baseline and at various time points. In addition, peripheral venous blood samples were obtained and biomarkers of cardiac and hemodynamic stress or inflammation were assessed. Purified P-188 demonstrated a statistically significant improvement in numerous parameters of heart function, including left ventricular ejection fraction and end-systolic volume, stroke volume, cardiac output and on tested biomarkers. The improvements in left ventricular function were achieved with minimal effect on left ventricular end-diastolic pressure, end-diastolic volume, systemic vascular resistance or heart rate. This indicates that mechanisms, other than vasodilation (i.e. alteration in cardiac loading conditions) are involved. Also, the reduction in cardiac troponin (TnI) indicates P-188 is limiting ongoing cardiomyocyte loss, possibly limiting unregulated calcium entry into the cell and calcium overload.

While the results show effects on systolic and diastolic function, the effect on systolic function is more pronounced. Thus, the results indicate that P-188 can treat heart failure in subjects with abnormal systolic function by improving left ventricular ejection fraction and end-systolic volume and stroke volume. Results, such as those described in Example 6 indicate that an additional infusion at three weeks results in continued benefits with additional improvement over the first administration.

The results provided herein indicate that P-188, such as purified P-188 (e.g., LCMF), can preserve heart tissue and directly improve heart function. This is an improvement over most existing treatments that target indirect methods that reduce workload on the heart and provide short-term symptomatic relief, but that do not directly improve heart function. The effect of P-188 can limit the accelerated cardiac damage that occurs during acute decompensation. In patients with heart failure, acute decompensation is a time of increased vulnerability, where disease progression accelerates and the risk of organ damage increases. An acute intervention that alters the trajectory of decompensation, whether by decreasing cardiac workload or preserving heart tissue, can minimize organ damage and improve long-term outcomes.

Based on the findings herein, the effects of a single infusion of P-188, and in particular purified P-188 (e.g., LCMF), lasts for at least a week and up to three weeks. Thus, methods for treating or ameliorating heart failure using a less frequent administration protocol than employed in the prior art is provided. For example, the results demonstrate that a therapeutic benefit is achieved for up to one week or more, including up to three weeks, after a single administration of P-188, so that any repeat administrations are not given until at least one week or more, such as 3 weeks, after the prior administration. The longer term benefits of P-188, and ability to provide a less frequent dosage regime, address problems in the art with existing chronic therapies related to fluid volume overload, renal insufficiency in subjects with heart failure, drug toxicity, and compliance of subjects when frequent repeat administrations or continuous infusion are necessary, especially if subjects must remain in or return to hospitals on a frequent (e.g., daily) basis for treatments.

4. Multiple Infusions of P-188

As described above, a single short-term infusion of P-188 has an unexpectedly long duration of action in improving heart function. The effect is sustained for up to three weeks. It also is shown herein that heart function can be sustained and even further improved with additional infusions of the P-188, if the same dosage (typically, 100 mg/kg to 600 mg/kg) is re-administered at certain intervals. The improvement in heart function with repeat administration builds upon the improvement observed following the first administration. The improvement is manifested as increased durability and also the magnitude of the effect. Because durability is increased, subsequent infusions can be administered at longer intervals. The dose administered per infusion can also be reduced over time depending upon the needs of a patient.

Regimens for treatment of heart failure, thus, are provided. For example, the P-188 can be administered at 1-2 week intervals, 2-3 week intervals, 3-4 week intervals, 4-5 week intervals or 5-6 week intervals at doses, such as between 100-500 mg/kg, which are infused, typically over 1-6 hours. In other regimens, the interval between doses can be increased over time, whereby the second dose is administered 2-3 weeks after the first dose, the third dose administered 3-4 weeks after the second dose and the fourth and any subsequent dose is administered 4-6 weeks following the previous dose. As performance of the heart improves, as assessed by standard parameters, such as those described herein, the dose can be titrated downward depending on the needs of the patient.

The following sections describe poloxamers, such as poloxamer 188, and compositions thereof for use in treating or ameliorating heart failure, including in the treatment of diseases or conditions associated with heart failure. Exemplary dosage regimes and methods are described.

C. Poloxamers And Purified Poloxamers

Provided herein are methods and uses of a poloxamer, and in particular a poloxamer 188 (P-188), such as a purified P-188, including LCMF poloxamer 188, for treating or ameliorating heart failure. Poloxamers are a family of synthetic, linear, triblock copolymers composed of a core of repeating units of poly(oxypropylene) (PO), flanked by chains of repeating units of (poly)oxyethylene (EO). All poloxamers are defined by this EO-PO-EO structural motif. Specific poloxamers (e.g., P-188) are further defined by the number of repeating EO and PO units, which provide specific poloxamers with different chemical and physical characteristics, as well as unique pharmacodynamic properties.

Certain polyoxyethylene/polyoxypropylene copolymers, including P-188, have been found to have beneficial biological effects on several disorders when administered to a human or animal. These activities have been described, for example, in numerous publications and patents (see, e.g., U.S. Pat. Nos. 4,801,452, 4,837,014, 4,873,083, 4,879,109, 4,897,263, 4,937,070, 4,997,644, 5,017,370, 5,028,599, 5,030,448, 5,032,394, 5,039,520, 5,041,288, 5,047,236, 5,064,643, 5,071,649, 5,078,995, 5,080,894, 5,089,260, RE 36,665 (Reissue of U.S. Pat. No. 5,523,492), U.S. Pat. Nos. 5,605,687, 5,696,298 6,359,014, 6,747,064, 8,372,387, 8,580,245, U.S. Patent Publication Nos. 2011/0044935, 2011/0212047, 2013/0177524, and International Applications WO2006/037031 (filed as PCT/US2005/034790), and WO2009/023177 (filed as PCT/US2005/037157) and WO2006/091941 (filed as PCT/US2006/006862). Among the activities of poloxamers, such as P188, that make them useful as therapeutic agents is their ability to incorporate into cellular membranes, and thereby repair damaged cell membranes.

Poloxamers include POP/POE block copolymers having the following formula:

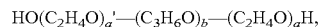

$$HO(C_2H_4O)_{a'}\text{—}(C_3H_6O)_b\text{—}(C_2H_4O)_aH,$$

where "a'" and "a" can be the same or different and each is an integer such that the hydrophile portion represented by $(C_2H_4O)$ constitutes approximately 50% to 95% by weight of the compound, such as 60% to 90%, for example 70% to 90%, by weight of the compound; and the "b" is an integer such that the hydrophobe represented by $(C_3H_6O)$ has a molecular weight of approximately 950 to 4,000 Da, such as 1,200 to 3,500 Da. For example, the hydrophobe has a molecular weight of 1,200 to 2,300 Da, such as generally 1,500 to 2,100 Da. The average molecular weight of the copolymer is 5,000 to 15,000 Da, such as 5,000 to 12,000 Da, for example 5,000 and 9,000 Da.

In certain instances, b is an integer of from about 15 to about 70, such as from about 15 to about 60, or from about 15 to about 30, or any of the numbers in between. In some instances, b is about 15, 16, 17, 18, 19, 20, 21, 22, 23, 24, 25, 26, 27, 28, 29, or 30. In certain aspects, the integers for the flanking units with the subscript "a" and "a'" can differ or are the same values. In some instances, a or a' is an integer of about 45 to about 910, such as 90, 100, 200, 300, 400, 500, 600, 700, 800, or 900. In some other instances, a or a' is an integer from about 10 to about 215, such as 10, 20, 30, 40, 50, 60, 70, 80, 100, 125, 150, 175, 200 or 215. In still other instances, a or a' is about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or 70. A skilled artisan will appreciate that these values are average values. The values for a', a and b represent an average; generally the polymeric molecules are a distribution or population of molecules. Therefore the actual values of a, a' and b within the population will constitute a range of values.

The nomenclature of the poloxamer relates to the composition of the various polymer members. The first two digits of a poloxamer number, multiplied by 100, gives the approximate molecular weight of the hydrophobe. The last digit, times 10, gives the approximate weight percent of the hydrophile (polyoxyethylene) content of the surfactant. For example, poloxamer 407 describes a polymer containing a polyoxypropylene hydrophobe of about 4,000 Da with the polyoxyethylene hydrophile comprising about 70% of the total molecular weight. Poloxamer 188 (P188) has a hydrophobe with a molecular weight of about 1,800 Da and has a hydrophile that is about 80% of the total molecular weight of the copolymer.

Poloxamers are sold and referred to under trade names and trademarks including, but not limited to, ADEKA NOL, Synperonic™, Pluronic® and Lutrol®. Exemplary poloxamers include, but are not limited to, poloxamer 188 (P-188; sold under the trademarks Pluronic® F-68, Kolliphor® P 188, RheothRx and Flocor™; 80% POE), poloxamer 407 (P407; sold under the trademark Lutrol F-127, Kolliphor® P-188, Pluronic® F-127; 70% POE), poloxamer 237 (P237; sold under the trademark Pluronic® F87, Kolliphor® P 237; 70% POE), and poloxamer 338 (P338; sold under the trademark Kolliphor® P 338, Pluronic® F-108; 80% POE).

Poloxamers, including P-188, for use in the methods herein include purified preparations of a poloxamer. Poloxamers are sold and referred to under trade names and trademarks, in including, but not limited to, ADEKA NOL, Synperonic™, Pluronic® and Lutrol®. Exemplary poloxamers include, but are not limited to, poloxamer 188 (P188; sold under the trademarks Pluronic® F-68, Kolliphor® P 188, 80% POE), poloxamer 407 (P407; sold under the trademark Lutrol F-127, Kolliphor® P 188, Pluronic® F-127; 70% POE), poloxamer 237 (P237; sold under the trademark Pluronic® F87, Kolliphor® P 237; 70% POE), poloxamer 338 (P338; sold under the trademark Kolliphor® P 338, Pluronic® F-108; 80% POE) and poloxamer 331 (Pluronic® L101; 10% POE).

Hence, non-purified P188 is commercially available or known under various names as described above. While the discussion below references using the methods herein to produce a more homogenous (LCMF) poloxamer 188, methods herein can be used to produce more homogenous preparations of any of the known poloxamers.

Poloxamers can be synthesized using standard polymer synthesis techniques. For example, poloxamers are formed by ethylene oxide-propylene oxide condensation using standard techniques know to those of ordinary skill in the art (see, e.g., U.S. Pat. Nos. RE 36,665, RE 37,285, RE 38,558, 6,747,064, 6,761,824 and 6,977,045; see also Reeve, L. E., The Poloxamers: Their Chemistry and Medical Applications, in Handbook of Biodegradable Polymers, Domb, A. J. et al. (eds.), Hardwood Academic Publishers, 1997). Poloxamers can be synthesized by sequential addition of POP and POE monomers in the presence of an alkaline catalyst, such as sodium or potassium hydroxide (See, e.g., Schmolka, J. Am. Oil Chem. Soc. 54 (1977) 110-116). The reaction is initiated by polymerization of the POP block followed by the growth of POE chains at both ends of the POP block. Methods of synthesizing polymers also are described in U.S. Pat. No. 5,696,298.

1. Poloxamer 188 (P-188)

Exemplary of poloxamers in the methods and uses provided herein is poloxamer 188 (P-188) and purified preparations thereof. A poloxamer 188 (P188) copolymer has the following chemical formula:

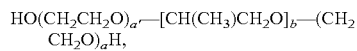
HO(CH$_2$CH$_2$O)$_a$—[CH(CH$_3$)CH$_2$O]$_b$—(CH$_2$CH$_2$O)$_a$H, where the hydrophobe represented by (C$_3$H$_6$O) has a molecular weight of approximately 1,750 Daltons and the poloxamer 188 has an average molecular weight of 7,680 to 9,510 Da, such as generally approximately 8,400-8,800 Daltons. The polyoxyethylene-polyoxypropylene-polyoxyethylene weight ratio of is approximately 4:2:4. According to specifications, P188 has a weight percent of oxyethylene of 81.8±1.9%, and an unsaturation level of 0.026±0.008 mEq/g.

Various poloxamers, and in particular P188, are used for treatment of diseases and conditions in which resistance to blood flow is pathologically increased by injury due to the presence of adhesive hydrophobic proteins or damaged membranes. This adhesion is produced by pathological hydrophobic interactions and does not require the interaction of specific ligands with their receptors. Such proteins and/or damaged membranes increase resistance in the microvasculature by increasing friction and reducing the effective radius of the blood vessel. For example, it is believed that poloxamer 188 acts as a lubricant to increase blood flow through damaged tissues. Advantageously, this blocks adhesion of hydrophobic surfaces to one another and thereby reduces friction and increases flow.

P188 binds to hydrophobic areas developed on injured cells and denatured proteins thereby restoring hydration lattices. Such binding facilitates sealing of damaged membranes and aborts the cascade of inflammatory mediators that could destroy the cell. This polymer also inhibits hydrophobic adhesive interactions that cause deleterious aggregation of formed elements in the blood. P188's anti-adhesive and anti-inflammatory effects are exhibited by enhancing blood flow in damaged tissue by reducing friction, preventing adhesion and aggregation of formed elements in the blood, maintaining the deformability of red blood cells, non-adhesiveness of platelets and granulocytes, the normal viscosity of blood, reducing apoptosis, and by multiple markers of inflammation including VEGF, various chemokines, interleukins, and chemokines 2. Molecular Diversity of Poloxamer 188

Commercially available poloxamer 188 preparations are stated to have a molecular weight of approximately 8,400 Daltons. Such poloxamer 188, however, is composed of molecules having a molecular weight from less than 3,000 Daltons to over 20,000 Daltons. The molecular diversity and distribution of molecules of commercial poloxamer 188 can be seen in the broad primary and secondary peaks detected using gel permeation chromatography (see, e.g., International Published PCT Application No. WO 94/08596).

The diversity in structure means that there is a diversity in biological activity. For example, the optimal rheologic, cytoprotective, anti-adhesive and antithrombotic effects are observed with molecules of P188 that are approximately 8,400 to 9,400 Daltons. Such components can be identified as the main or predominant component in a poloxamer preparation using methods that separate components based on size, such as gel permeation chromatography (GPC). The distribution of components, however, also typically show a smaller fraction of low molecular weight (LMW, i.e. generally below 4,500 Daltons) or high molecular weight (HMW, i.e. generally above 13,000 Daltons,) components. P188 components above 15,000 and below 4,500 Daltons are less effective rheologic or cytoprotective agents and exhibit unwanted side effects. The other substances or components in a poloxamer preparation, such as a P188 preparation, originate from two different sources, synthesis and degradation.

A primary mechanism contributing to the molecular diversity is the process by which poloxamers are synthesized. During the typical manufacturing process, the first step is the formation of the POP blocks. These are formed by reacting a propylene glycol initiator with propylene oxide monomer. Subsequently, ethylene oxide monomer is added to both ends forming the block copolymer. The synthesis of poloxamers can result in a variation in the rates of polymerization during the steps of building the PO core and EO terminal ends.

During the synthesis of the POP, two different reaction mechanisms limit POP chain growth and result in unintended diblock polymers. These substances are typically of lower molecular weight (relative to the polymeric distribution of P188). In one mechanism, unsaturation is formed directly from propylene oxide by reacting with an alkali catalyst. The base catalyzes the rearrangement of the propylene oxide to an allyl alcohol, which then initiates a mono functional chain with terminal unsaturation. These types of side reactions will produce low molecular weight (LMW) substances throughout the time of the reaction. On gel permeation chromatography (GPC), the distribution of these impurities are located in the main peak as well as in the LMW shoulder. In a second mechanism, the abstraction of a hydrogen atom, located six carbon atoms away, by the negative oxygen atom in a growing polymer chain can terminate and transfer the chain, producing an allyl end group. These back-biting reactions are predominant with high molecular weight (HMW) POP blocks. The distribution of these substances is mostly in the LMW shoulder.

In addition, high molecular weight substances (relative to the polymeric distribution of P188) can be formed due to inadequate cleaning of the polymerization reactor between batches of poloxamer 188 during a typical commercial manufacturing campaign. If the reactor is not completely cleaned to remove residual product after manufacturing a typical batch of poloxamer, such as P188, the residual product will act as an initiator in the subsequent batch and form a "dimer like" poloxamer molecule. This substance is of higher molecular weight and would be part of the polymeric distribution observed on GPC as the HMW shoulder.

The degradation pathways for poloxamers include peroxidation leading to low molecular aldehydes and acids and thermal degradation leading to LMW polyethylene glycols. Oxidative degradation is the primary degradation pathway affecting stability of poloxamers. This process generates structural changes to the polymer chain and generates peroxides and carbonyls. Peroxides are transient in nature and quickly combine with butylated hydroxytoluene (BHT), which is typically added to commercial preparations as an antioxidant. Thermal degradation is another pathway that produces other substances. Glycols of various chain lengths are major degradation products of thermal degradation. Forced thermal degradation studies have shown that ethylene glycol, propylene glycol, diethylene glycol and triethylene glycol are formed.

Thus, specific poloxamers are composed of multiple chemical entities that have the EO-PO-EO structural motif, but vary in the number of repeating EO and PO units. Various truncated polymers with an EO-PO motif and a variety of other substances can form as a result of side reactions occurring during synthesis of the intended poloxamer compound. These other substances can be present and found within the overall poloxamer distribution. The result is material that is non-uniform (i.e. material that is polydisperse).

For example, due to the synthesis of P188, there can be variation in the rates of polymerization during the steps of building the PO core and EO terminal ends. Thus, most non-purified forms of P188 contain a bell-shaped distribution of polymer species, which vary primarily in overall chain length. In addition, various low molecular weight (LMW) components (e.g., glycols and truncated polymers) formed by incomplete polymerization, and high molecular weight (HMW) components (e.g., dimerized polymers) can be present. Typically, characterization of P188 by gel permeation chromatography (GPC) identifies a main peak of P188 with "shoulder" peaks representing the unintended LMW and HMW components (Emanuele and Balasubramanian (2014) Drugs R D, 14:73-83). For example, the preparation of P188 that is available from BASF (Parsippany, N.J.) has a published structure that is characterized by a hydrophobic block with a molecular weight of approximately 1,750 Daltons (Da), POE blocks making up 80% of the polymer by weight, and a total molecular weight of approximately 8,400 Da. The actual compound is composed of the intended POE-POP-POE copolymer, but also contains other molecules which range from a molecular weight of less than 1,000 Da to over 30,000 Da. The molecular diversity and distribution of molecules of commercial poloxamer 188 is illustrated by broad primary and secondary peaks detected using gel permeation chromatography.

The diversity of molecules present in the non-purified poloxamer preparations, including commercially available poloxamers, can result in diverse biological activities. Many of the observed biological activities are undesired or/and can result in unwanted side effects that limit the therapeutic efficacy of poloxamers as drugs. Complement activation, phagocyte migration paralysis, and cytotoxicity observed upon administration of artificial blood preparations have been attributed in part to impurities in the poloxamer 188 component of those preparations. In addition, infusion of poloxamer 188 was shown to result in elevated creatinine, indicating kidney damage, and increased organ weights (kidney) in toxicological animal studies. Histologic evaluation of the kidney demonstrated a dose related cytoplasmic vacuolation of the proximal tubular epithelial cells.

Poloxamer 188 (see, e.g., Grindel et al. (2002) Journal of Pharmaceutical Sciences, 90:1936-1947 (Grindel et al. 2002a) or Grindel et al. (2002) Biopharmaceutics & Drug Disposition, 23:87-103 (Grindel et al. 2002b)), which is purified to remove lower molecular weight components, contains components that, when administered to a subject, exhibit different pharmacokinetic profiles. The main component exhibits a half-life ($t_{1/2}$) in plasma of about 7 hours and a higher molecular weight component (i.e. the longer retention time species) exhibits about a 10-fold or more increase in half-life with a $t_{1/2}$ of approximately 70 hours or more and, thus, a substantially longer plasma residence time with slower clearance from the circulation than the main component. This is demonstrated herein (see, FIG. 8A and FIG. 8B).

a. Low Molecular Weight Components

Substances in poloxamer 188 that are toxic to kidneys have been identified as being of lower molecular weights than the main components. Studies on the therapeutic potential of P 188 led to the discontinuance of the poloxamer available under the trademark RheothRx® for therapeutic applications in part due to an acute renal dysfunction observed during clinical trial evaluation as evidenced by elevated serum creatinine. It was found that these effects were due to the presence of various low molecular weight (LMW) substances that formed during the synthesis process (Emanuele and Balasubramanian (2014) Drugs R D, 14:73-83). The LMW substances were accumulated by the proximal tubule epithelial cells in the kidney.

The molecular weight of the LMW substances can range from a few hundred Da to a few thousand Da. The complex nature of these impurities with wide solubility characteristics make it difficult to selectively remove them from the parent molecules. Conventional purification processes such as distillation, crystallization, ultrafiltration, and the like, do not effectively separate the low molecular weight (LMW) substances from the main component. Use of chromatographic techniques for purification such as preparative GPC are expensive and practically difficult to scale-up. Fine-tuning mixed solvent systems to differentially solubilize and remove various substances is also challenging and requires the use of large amounts of solvents that are costly to recycle.

Supercritical fluid chromatography that reduces the level of these low molecular weight substances present in P188 has been reported (see, e.g., U.S. Pat. No. 5,567,859). Supercritical fluid extraction was performed using carbon dioxide to purify the copolymers to reduce the polydispersity to less than 1.17. The method, however, does not sufficiently remove or reduce LMW components and, as shown herein, other components.

As described in more detail below, the methods provided herein produces poloxamer preparations that are substantially free of these LMW components. For example, purified P188 reduced in LMW components have less than about 5%, 4%, 3%, 2% or 1% LMW components. Thus, the poloxamer preparations provided herein, and in particular P188 poloxamer preparations, generally exhibit reduced toxicity and do not result in elevated creatinine levels when administered. In addition, as described herein the resulting LCMF P188 poloxamer preparation has other advantageous properties, including a reduction of long circulating material upon administration.

b. Components Resulting in Long Circulating Half-Life

A component in P188 has been identified that is or gives rise to a material in the plasma or blood with a longer circulating half-life compared to the main or predominant poloxamer species. This material with the longer circulating half-life is observed in non-clinical and clinical studies. Analysis of plasma obtained following intravenous administration of purified P188 by high performance liquid chromatography—gel permeation chromatography (HPLC-GPC) shows two distinct peaks in the circulation (Grindel et al. (2002) *Journal of Pharmaceutical Sciences,* 90:1936-1947 (Grindel et al. 2002a) or Grindel et al. (2002) *Biopharmaceutics & Drug Disposition,* 23:87-103 (Grindel et al. 2002b))). There is a main peak with average peak molecular weight of about 8,600 Daltons and a smaller peak with an average molecular weight of about 16,000 Daltons. The two peaks exhibit distinctly different pharmacokinetic profiles with the higher molecular weight peak exhibiting a distinctly longer plasma residence time with slower clearance from the circulation (see FIG. 8A and FIG. 8B). Similar observations were reported in rats and dogs. A similar long circulating component is observed with native or unpurified poloxamer 188 (see, e.g., published International PCT Application No. WO 94/008596)

Figure 8A:
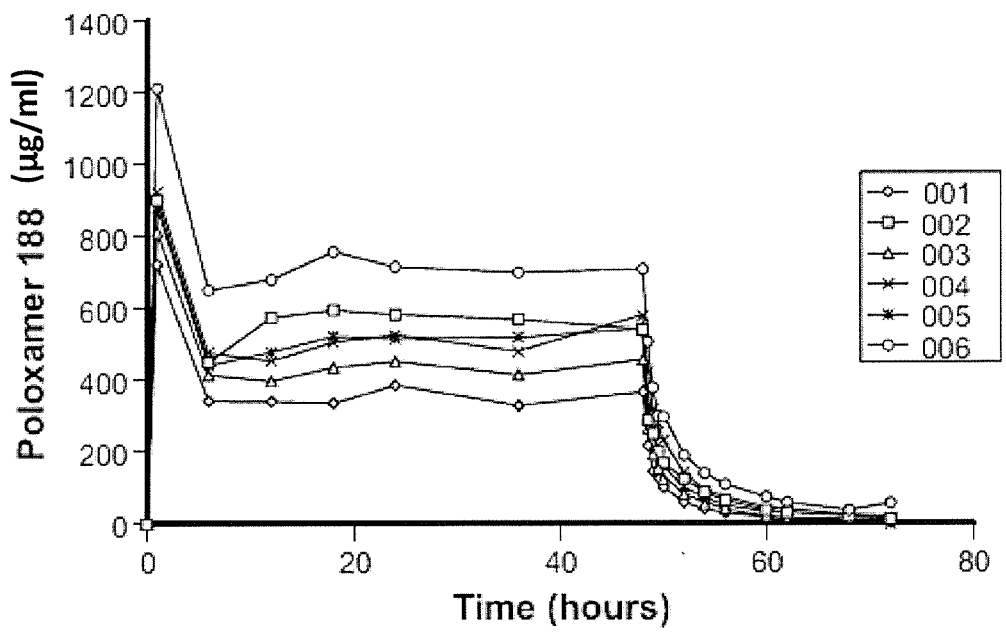
FIG. 8A-B shows individual plasma concentrations of Poloxamer 188 (Panel A) and high molecular weight component (Panel B) in healthy humans during and following a 48 hour continuous IV infusion of purified poloxamer 188 as described in Grindel et al. (2002) (Biopharmaceutics & Drug Disposition, 23:87-103).

For example, as shown in FIG. 8A, following administration of a purified P188 intravenously to healthy volunteers as a loading dose of 100 mg/kg/hr for one hour followed by a maintenance dose of 30 mg/kg/hr for 47 hours, the main or predominant peak reached a mean maximum concentration (Cmax) of 0.9 mg/mL by the end of the one hour loading infusion. A mean steady state concentration (Css) of 0.5 mg/mL was achieved essentially coincident with the start of the maintenance infusion. With the discontinuation of the maintenance infusion, plasma concentrations declined rapidly with an elimination half-life (t½) of about 7 hours.

Figure 8B:
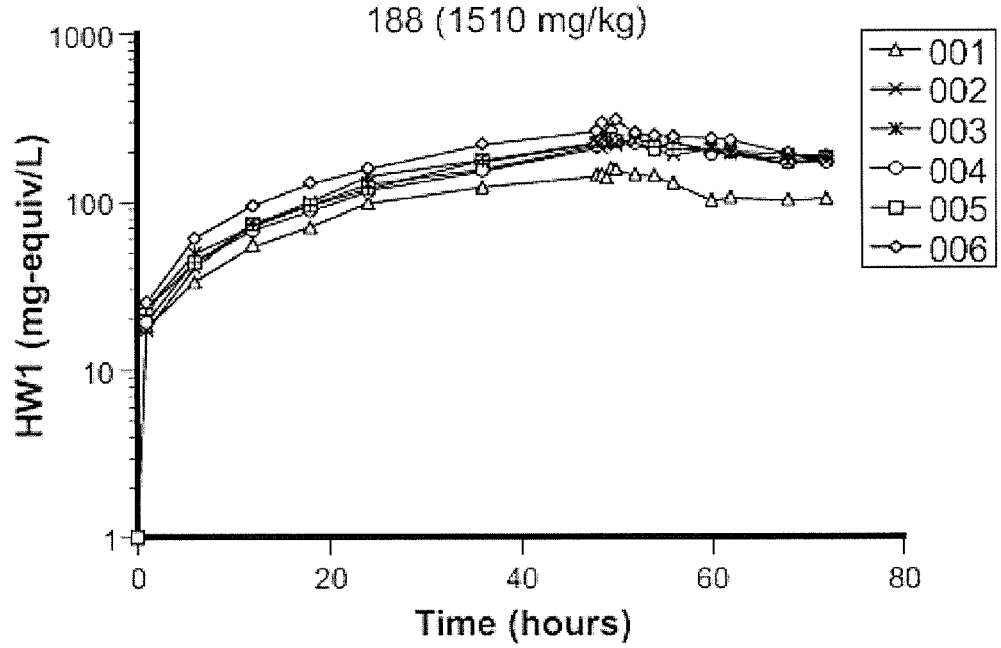

As shown in FIG. 8B, a HMW component was identified that exhibited a Cmax of 0.2 mg/mL, which was not attained until the end of the maintenance infusion. Steady state was not attained as the concentration continued to accumulate during infusion. Following discontinuation of the maintenance infusion, plasma levels of the high molecular weight peak declined slowly such that plasma levels had only declined by about 33% during the 24 hour post-infusion monitoring period. This elimination rate is approximately ¹⁄₁₀ that of the main peak and the t½ is approximately 70 hours. See, also Grindel et al. (2002) *Journal of Pharmaceutical Sciences,* 90:1936-1947 (Grindel et al. 2002a) and Grindel et al. (2002) *Biopharmaceutics & Drug Disposition,* 23:87-103 (Grindel et al. 2002b)) The long circulating material (or longer retention time material) is identified in the HMW fraction of the P188 distribution (Grindel et al. 2002a). This HMW component was determined to be approximately 16,000 Da as identified by MALDI-TOF mass spectrometry with a fragmentation pattern consistent with a block copolymer (Grindel et al. 2002a).

Since the rheologic, cytoprotective, anti-adhesive and antithrombotic effects of P188 are optimal within the predominant or main copolymers of the distribution, which are approximately 8,400 to 9400 Daltons and have a half-life of about 7 hours, the presence of other components that exhibit a long circulating half-life is not desirable. For example, among the desired activities of P188 is its rheologic effect to reduce blood viscosity and inhibit red blood cell (RBC) aggregation, which account for its ability to improve blood flow in damaged tissues. In contrast, higher molecular weight poloxamers such as P338 (also called Pluronic® F108) and P308(Pluronic® F98), increase blood viscosity and RBC aggregation (Armstrong et al. (2001) *Biorheology,* 38:239-247). This is the opposite effect of P188 and indicates that higher molecular weight poloxamer species may have undesirable biological effects.

As described in more detail below, provided are poloxamer preparations that are substantially reduced in the component that is or gives rise to a long circulating material, i.e. they are long circulating material free (LCMF). Also provided are exemplary methods (see, Example 1) for production of LCMF poloxamer. Thus, the LCMF poloxamer preparations provided herein, and in particular LCMF P188 poloxamer preparations, exhibit a more uniform pharmacokinetic profile, and thus a more consistent therapeutic effect. The LCMF poloxamer is described in more detail in the following section.

3. Long Circulating Material Free (LCMF) Poloxamer

For the methods provided herein, the poloxamer can be a long circulating material free (LCMF) P188 that is a purified P-188 that has a polydispersity value less than 1.07; has no more than 1.5% of low molecular weight (LMW) components less than 4,500 Daltons; no more than 1.5% high molecular weight components greater than 13,000 Daltons; a half-life of all components in the distribution of the co-polymer that, when administered to a subject, is no more than 5.0-fold longer half-life in the blood or plasma than the half-life of the main component in the distribution of the co-polymer. Methods for treating heart failure by administering the LCMF P-188 are provide.

The LCMF Poloxamer 188, when administered, does not give rise to a component that has a significantly longer half-life than the main component. The LCMF P-188 has the following chemical formula:

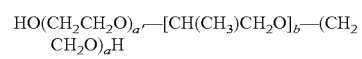

where a' and a can be the same or different and each is an integer such that the hydrophile portion represented by ($C_2H_4O$) (i.e., the polyoxyethylene portion of the copolymer) constitutes approximately 60% to 90%, such as approximately 80% or 81%; and b is an integer such that the hydrophobe represented by ($C_3H_6O$) has a molecular weight of approximately 1,300 to 2,300 Da, such as approximately 1,750 Da; and the average total molecular weight of the compound is approximately 7,680 to 9,510 Da, such as generally 8,400-8,800 Da, for example about or at 8,400 Da, where the copolymer has been purified to remove impurities, including low molecular weight impurities or other impurities, so that the polydispersity value is less than 1.07

Studies have demonstrated that the main peak component of a purified P-188 preparation, when administered to a human subject, has a half-life ($t_{1/2}$) in plasma of about 7 hours (Grindel et al. (2002) *Journal of Pharmaceutical Sciences*, 90:1936-1947 (Grindel et al. 2002a) or Grindel et al. (2002) *Biopharmaceutics & Drug Disposition*, 23:87-103 (Grindel et al. 2002b)). The purified poloxamer also resulted in a long circulating material containing higher molecular weight components that have an average molecular weight of about 16,000 Daltons, which exhibit about a 10-fold or more increase in half-life with a $t_{1/2}$ of approximately 70 hours.

In contrast to the purified P-188 characterized in the studies of Grindel et al., (2002a and 2002b), the purified poloxamer, designated LCMF P-188, is one in which all components of the polymeric distribution, when administered to a subject, clear from the circulation at approximately the same rate. Thus, the LCMF P-188 is different from prior LCM containing p188 poloxamers. Like LCM containing poloxamers, LCMF poloxamer contains a substantially polydisperse composition of less than 1.07, and generally less than 1.05 or 1.03, but where the half-life in the blood or plasma of any components in the distribution of the co-polymer, when administered to a human subject, is no more than 5.0-fold longer than the half-life of the main component in the distribution of the co-polymer, and generally no more than 4.0-fold, 3.0-fold, 2.0-fold, 1.5-fold more longer. Typically, the LCMF does not contain any component that exhibits a half-life in the blood or plasma, when administered to a subject, that is substantially more than or is more than the main component in the distribution of the co-polymer.

In some examples, the half-life in the blood or plasma of all components in the LCMF poloxamer, when administered to a human subject, is such that no component has a half-life that is more than 30 hours, and generally is no more than 25 hours, 20 hours, 15 hours, 10 hours, 9 hours, 8 hours or 7 hours.

Without being bound by theory, higher molecular weight components of the poloxamer polymeric distribution, such as those greater than 13,000 Daltons could account for the long circulating half-life material. The rate of glomerular filtration of uncharged molecules like poloxamer 188 and purified poloxamer 188 is highly dependent upon molecular size. This is observed for components of the poloxamer 188 polymeric distribution with molecular weights greater than 5,000 Daltons since, the rate of glomerular filtration becomes increasingly restricted above that size threshold. (Chang et al., (1975) *Biophysic. J.* 15:887-906) Accordingly, the higher molecular weight components of the poloxamer 188 polymeric distribution (such as those greater than 13,000 Daltons would be more likely to be cleared from the circulation. at a slower rate than those of smaller size.

For the LCMF preparations, however, the presence of HMW components in the distribution do not result in a longer circulating species. For example, HMW impurities greater than 13,000 Daltons in an LCMF preparation, generally constitute no more than 1.5% by weight of the total component. When the LCMF preparation is administered to a subject, these HMW impurities do not result in a circulating half-life that is more than 5.0-fold longer than the half-life of the main component in the distribution, and generally no more than 4.0-fold, 3.0-fold, 2.0-fold, 1.5-fold more longer. When the LCMF preparation is administered to a subject, they do not result in any component with a circulating half-life that is substantially more than or is more than the main component in the distribution (see, e.g., FIGS. 7A and 7B).

In the LCMF preparation, the HMW components can be either increased or decreased compared to other existing purified P-188 preparations. For example, an LCMF poloxamer provided herein includes P-188 poloxamers in which there are no more than 1.3% high molecular weight components greater than 13,000 Daltons, such as no more than 1.2%, 1.1%, 1.0% or less. In particular examples provided herein, an LCMF poloxamer provided herein includes P-188 poloxamers in which there are less than 1.0% by weight high molecular weight components greater than 13,000 Daltons, and generally less than 0.9%, 0.8%, 0.7%, 0.6%, 0.5% or less.

The LCMF poloxamer provided herein can be prepared by methods as described herein below (see section 4, below, and see, e.g., FIG. 3). In view of the description and exemplification of the properties of the LCMF poloxamer, those of skill in the art can envision other methods for producing an LCMF poloxamer. For example, an LCMF poloxamer provided herein is made by a method that includes:

a) introducing a poloxamer solution into an extractor vessel, where the poloxamer is dissolved in a first alkanol to form a solution;

b) contacting the poloxamer solution with an extraction solvent comprising a second alkanol and supercritical carbon dioxide under a temperature and pressure to maintain the supercritical carbon dioxide for a first defined period, wherein:

the temperature is above the critical temperature of carbon dioxide but can typically range between 35° C.-45° C.;

the pressure is 220 bars to 280 bars; and the alkanol is provided at an alkanol concentration that is 7% to 8% by weight of the total extraction solvent; and c) increasing the concentration of the second alkanol in step b) in the extraction solvent a plurality of times in gradient steps over time of the extraction method, wherein:

each plurality of times occurs for a further defined period; and in each successive step, the alkanol concentration is increased 1-2% compared to the previous concentration of the second alkanol; and d) removing the extraction solvent from the extractor vessel to thereby remove the extracted material from the raffinate poloxamer preparation.

4. Extraction Method for Purifying Poloxamers

Any method known to a skilled artisan can be used to purify a poloxamer. In particular, supercritical methods can be employed. A supercritical extraction permits control of the solvent power by manipulation of temperature, pressure and the presence of a co-solvent modifier. Provided and described are supercritical fluid extraction (SFE) and high-pressure procedures for purifying poloxamers such that the purified polymer is more homogenous with regard to structure (diblock, triblock, etc.), the percentage of molecules without unsaturation, the distribution of molecular weights, and distribution of hydrophobic/hydrophilic (HLB) ratios. The tunability of the processes can be leveraged to effectively remove extraneous components and can be adjusted over time, which can increase the yield of the purified product. The method provided herein uses a solvent system that is variable in its solvation characteristics in order to selectively remove various substances. The methods provide an exemplary way to produce the LCMF poloxamer 188 product, which has the above properties.

Methods herein provide poloxamer preparations that differ from those produced by prior methods. These include the LCMF poloxamer 188 preparation that, upon administration, does not give rise to longer circulating material observed with purified poloxamer 188, such as that described in U.S. Pat. No. 5,696,298. The LCMF poloxamer 188 has the molecule size distribution similar to the purified poloxamer 188, but the component molecules produce a preparation that is more hydrophilic than purified poloxamer.

The absence of the long circulating material (LCM) improves the properties of the poloxamer, including faster clearance and other such improved pharmacological properties by virtue of the elimination of the longer circulating material. The methods provided herein eliminate unwanted components in a poloxamer preparation, and thereby prepare a more homogenous or uniform poloxamer preparation that exhibits desired therapeutic activity while minimizing or reducing undesired activities. Because commercially available poloxamers have been reported to exhibit toxicity as well as variation in biological activity, a poloxamer preparation that is more uniform and homogenous has reduced toxicity but retains therapeutic efficacy of the main copolymer component.

Provided herein are methods for preparing such poloxamers, and provided are the resulting poloxamers, including the LCMF poloxamer 188. The methods provided herein, in addition to resulting in poloxamer preparations in which low molecular weight (LMW) components are reduced or removed, also result in long circulating material free (LCMF) preparations that are reduced or removed for any component that is or gives rise to a circulating material in the plasma or blood as described herein. Hence, also provided herein are LCMF preparations of poloxamers, and in particular LCMF poloxamer 188. The LCMF poloxamer 188 provided herein can be used for all of the uses known for poloxamer 188.

Provided herein are extraction methods for purifying poloxamers, such as P188, in order to remove or reduce components other than the main component, and thereby decrease the molecular diversity of the preparation. For example, the methods can remove or reduce LMW substances in a poloxamer. It is also found herein, that, in addition to removing or reducing LMW substances, particular methods provided herein also remove or reduce components in a poloxamer preparation that is or gives rise to a long circulating material that has a half-life that is substantially longer than the half-life of the main component in the distribution. The degree of extraction, and components that are extracted, are controlled by the particular temperature, pressure and alkanol concentration employed in the methods as described herein.

The methods provided herein employ a supercritical or subcritical extraction solvent in which the solvent power is controlled by manipulation of temperature, pressure in the presence of a co-solvent modifier. It is found that carbon dioxide is not a particularly efficient extraction solvent of poloxamers, such as P188, but that the presence of a polar co-solvent, such as an alkanol, as a modifier increases the solubilizing efficiency of $CO_2$ in the extraction solvent. In particular, the methods provided herein are performed in the presence of a polar co-solvent, such as an alkanol, whose concentration is increased in a gradient fashion (e.g., a step-wise gradient or a continuously escalating gradient) as the extraction process progresses. It is found that by employing an alkanol co-solvent whose concentration is increased in this manner, the removal of impurities can be increased, and to a much greater extent than when carbon dioxide is used alone. For example, an extraction method that uses carbon dioxide alone is not capable of removing the unwanted components, such as the LMW components and HMW components as described herein, to the same degree as that achieved by the provided method.

In the methods provides herein for purifying a poloxamer using supercritical fluid extraction, the LMW components or impurities of a poloxamer distribution can be selectively removed with a lower alkanol concentrations (e.g., methanol) and higher pressure than other HMW components in the distribution. As described further below, by increasing the solubilizing power of the extraction solvent, for example by carefully controlling the pressure and concentration of polar solvent, such as an alkanol (e.g., methanol), it also is possible to remove other impurities. In particular, a method is provided employing a gradient of higher concentrations of an alkanol (such as methanol), alone or in conjunction with a decrease in the pressure, that results in the removal of components (e.g., HMW components) in a poloxamer distribution such that, when the resulting product is administered to a subject, it does not result in a long circulating material in the plasma that is observed with the previous P188 products.

There, however, can be a tradeoff with respect to the yield of poloxamer. Generally, as the concentration of the alkanol (e.g., methanol) co-solvent increases, the solvating power of the extraction solvent is increased so that more compounds are solubilized and the degree of extraction increases. By increasing the concentration of extraction solvent in a gradient fashion, the reduction of poloxamer yield is minimized, while the purity of the final product is maximized. Typically, the methods provided herein achieve a yield such that the amount of the extracted or purified polymer obtained by the method is at least 55%, 60%, 70%, 75%, 80%, 85%, 90% or more of the starting amount of the poloxamer prior to performance of the method. The resulting poloxamers, however, exhibit a substantially greater purity with a higher percentage of main component in the distribution than the starting material, and without impurities that exhibit toxic side effects or that can result in a long circulating material in the plasma when administered.

The methods can be performed on any poloxamer in which it is desired to increase the purity, for example by decreasing or reducing components that are undesired in the distribution of a polymer. It is within the level of a skilled artisan to choose a particular poloxamer for purification in this manner. Undesired components include any that are or give rise to a material that is toxic or that has a biological activity that is counter or opposing to the desired activity. For example, the poloxamer can be one in which it is desired to reduce or remove LMW components in the poloxamer, for example, any LMW components that result in acute renal side effects, such as elevated creatinine, when administered. The poloxamer also can be one that contains any component, such as a HMW component, that, when administered, is or gives rise to a material that has a half-life in the blood that is different (e.g., longer) than the half-life of the main component in the distribution of the polymer. Such components can increase blood viscosity and red blood cell aggregation, and hence are undesired.

Exemplary of poloxamers for use in the methods include, but are not limited to, poloxamer 188, poloxamer 331, and poloxamer 407. Typically, the poloxamer is one in which the average molecular weight of the main component is within or about 4,700 Da to 12,800 Da, such as generally 7,680 Da to 9,510 Da, for example generally 8,400-8,800 Da. In particular, the poloxamer is P188.

For example, the extraction methods provided herein can be employed to purify a P188 preparation, where the P188 preparation has the following chemical formula:

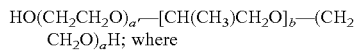
$HO(CH_2CH_2O)_a-[CH(CH_3)CH_2O]_b-(CH_2CH_2O)_aH$; where the hydrophobe represented by ($C_3H_6O$) has a molecular weight of approximately 1,750 Daltons and an average molecular weight of 7,680 to 9,510 Da, such as generally approximately 8,400-8,800 Daltons. The polyoxyethylene-polyoxypropylene-polyoxyethylene weight ratio of P188 is approximately 4:2:4. P188 has a weight percent of oxyethylene of 81.8±1.9%, and an unsaturation level of 0.026±0.008 mEq/g. P188 preparations for use in the methods herein include commercially available preparations. These include, but are not limited to, Pluronic® F68 (BASF, Florham Park, N.J.) and RheothRx® (developed by Glaxo Wellcome Inc.).

In practicing the extraction methods, provided herein, the methods include: a) providing a poloxamer (e.g., P188) solution into an extractor vessel, where the poloxamer solution is prepared by dissolving the poloxamer in a first solvent to form the solution; b) admixing an extraction solvent containing a supercritical liquid (e.g., supercritical carbon dioxide) or sub-critical fluid (e.g., high pressure carbon dioxide) and a co-modifier solvent with the solution to form an extraction mixture, wherein the concentration of the co-modifier solvent in the extraction solvent is increased over the time of extraction method; and c) removing the extraction solvent from the extractor vessel to thereby remove the impurities (e.g., LMW and/or other components), from the poloxamer. In the method, the step of dissolving the poloxamer solution in the first solvent can occur prior to charging the solution into an extraction vessel or at the time of charging the solution into an extraction vessel. For example, the poloxamer is dissolved in a separate vessel and then the solution is added to the extraction vessel.

The method can be a high pressure or supercritical fluid extraction method. Typically, the method is performed using supercritical fluid extraction (SFE) using a supercritical liquid in the extraction solvent. A supercritical liquid is any liquid that is heated above the critical temperature and compressed to above the critical pressure. For example, carbon dioxide has a critical temperature of 31.1° C. and a critical pressure of 73.8 bars. Thus, extraction conditions for a supercritical carbon dioxide are above the critical temperature of about 31° C. and critical pressure of about 74 bars. In contrast, high pressure extraction can be achieved under sub-critical conditions in which the pressure exceeds the critical pressure, but the temperature does not exceed the critical temperature.

a. Processes for Extraction
i. Supercritical Methods

In certain instances, the supercritical fluid extraction process employed in the methods provided herein is essentially a solvent extraction process using a supercritical fluid as the solvent. With supercritical fluid, multi-component mixtures can be separated by exploiting the differences in component volatilities and the differences in the specific interactions between the component mixture and supercritical fluid solvent (solvent extraction). In the supercritical region of the phase diagram, a compressible fluid such as carbon dioxide exhibits liquid-like density and much increased solvent capacity that is pressure dependent.

The supercritical fluid exhibits a number of highly advantageous characteristics making it a superior solvent. For example, the tunable solvent power of a supercritical fluid changes rapidly around critical conditions within a certain range. The solvent power of the supercritical fluid, and thus the nature of the component that can be selectively removed during extraction, can be fine-tuned by varying the temperature and pressure of the supercritical fluid solvent.

Another beneficial property of various supercritical fluids is the difference in their critical temperatures and pressures. Each supercritical fluid has a range of solvent power. The tunable solvent power range can be selected by choosing an appropriate supercritical fluid.

In addition to its unique solubility characteristics, supercritical fluids exhibit certain physicochemical properties making them more useful. For example, supercritical fluids exhibit liquid-like density, and possess gas-like transport properties such as diffusivity and viscosity. These characteristics also change rapidly around the critical region. Supercritical fluids also have zero surface tension. Since most of the useful supercritical fluids have boiling points around or below ambient temperature, the solvent removal step after purification is simple, energy efficient and does not leave any residual solvents.

The use of solid matrices during extraction provides an additional dimension for a fractionation parameter. A suitable solid matrix provides solvent-matrix and solute-matrix interactions in addition to solute-solvent interactions to enhance the fractionation resolution. The desirable transport properties of supercritical fluids make the process easily scalable for manufacturing. Heat transfer and mass transfer characteristics do not significantly change upon process scale up with supercritical fluid extraction processes. Since the extraction process conditions, such as pressure, temperature, and flow rate, can be precisely controlled, the purification process is reproducible in addition to highly tunable.

In such a method, the extraction solvent can contain a supercritical liquid (e.g., supercritical carbon dioxide), as well as another co-modifier solvent, generally an alkanol, that is increased over time in the extraction. As described above, the presence of the co-modifier solvent can improve the solubility of solutes, such as higher molecular weight or more non-polar solutes, and thereby increase their extraction in the method.

For example, the method provided herein can include: a) providing or introducing a poloxamer (e.g., a poloxamer 188) solution into an extractor vessel, wherein the poloxamer solution is prepared by dissolving the poloxamer in a first alkanol to form the solution; b) admixing an extraction solvent containing a second alkanol and a supercritical liquid, under high pressure and high temperature sufficient to create supercritical liquid conditions, with the solution to form an extraction mixture, wherein the concentration of the second alkanol in the extraction solvent is increased over the time of extraction method; and c) removing the extraction solvent from the extractor vessel to thereby remove the impurities (e.g., LMW component or other components) from the poloxamer preparation. The first and second alkanol can be the same or different. In the method, the step of dissolving the poloxamer solution in the first solvent can occur prior to charging the solution into an extraction vessel or at the time of charging the solution into an extraction vessel. For example, the poloxamer is dissolved in a separate vessel and then the solution is added to the extraction vessel.

An exemplary process is detailed in FIG. 1. FIG. 1 depicts a process (100) that removes impurities (e.g., LMW component or other components) from a poloxamer preparation. The extraction system is pressurized, as shown in step 105, typically prior to dispensing a first alkanol into the feed mix tank, as shown in step 110. The system is heated to a temperature suitable for the extraction process. The temperature is typically a temperature that is above the critical temperature of the supercritical liquid (e.g., carbon dioxide). Generally, the temperature is approximately 40° C.

Any suitable alkanol or combination of alkanols can be used in the methods provided herein. Examples of suitable alkanols include, but are not limited to, methanol, ethanol, propanol, and butanol. For example, the method provided herein includes an extraction method as described above, wherein the first and the second alkanol are each independently selected from methanol, ethanol, propanol, butanol, pentanol and a combination thereof. In some embodiments, the first alkanol is methanol. In certain instances, methanol is selected as the purification solvent and is the second alkanol in practice of the method. A skilled artisan will appreciate that methanol has relatively low toxicity characteristics. Moreover, methanol has good solubility for poloxamer 188.

The first alkanol (e.g., methanol) is used to form a poloxamer solution according to step 115 in process 100. A poloxamer, such as a P188 preparation, is dispensed into the feed tank and is stirred until mixed with the first alkanol. The amount of poloxamer that is added to the feed tank is a function of the scalability of the extraction method, the size of the extraction vessel, the degree of purity to achieve and other factors within the level of a skilled artisan. For example, non-limiting amounts of poloxamer (e.g., P188) per mL of an extraction vessel can be 0.1 kg to 0.5 kg or 0.2 kg to 0.4 kg. In some examples, in methods of extraction using a 3 L extraction vessel, non-limiting amounts of poloxamer (e.g., P188) can be 0.6 kg to 1.2 kg, such as 0.8 kg to 1.0 kg. In another example, in methods of extraction using a 12 L extraction vessel, non-limiting amounts of poloxamer (e.g., P188) can be 1.5 kg to 5 kg, such as 2 kg to 4 kg. In a further example, in methods of extraction using a 50 L extraction vessel, non-limiting amounts of poloxamer (e.g., P188) can be 8 kg to 20 kg, such as 10 kg to 16 kg or 12 kg to 15 kg. Variations in the amounts are contemplated depending on the particular applications, extraction vessel, purity of the starting material and other considerations within the level of a skilled artisan.

Any suitable ratio of poloxamer and alkanol is contemplated for use in the methods provided herein. The ratio of poloxamer to alkanol, by weight, can be, for example, from about 4:1 to about 1:4, such as from about 3:1 to about 1:3, 2:1 to about 1:2, 1:1 to 4:1 or 1:2 to 1:4. For example, the ratio of poloxamer to alkanol, by weight, can be about 4 to 1, or about 3 to 1, or about 2 to 1, or about 1 to 1, or about 1 to 2, or about 1 to 3 or about 1 to 4. For example, a quantity of poloxamer, such as P188, can be mixed with an equal quantity, by weight, of alkanol (e.g., methanol). A quantity of poloxamer, such as P188, can be mixed with a lesser amount, by weight, of alkanol, such as half the amount, by weight, of alkanol (e.g., methanol). One of skill in the art will appreciate that the appropriate poloxamer to alkanol ratio will depend on poloxamer properties such as solubility in a given alkanol.

After forming a poloxamer/alkanol mixture, all or part of the mixture is pumped into the extractor as shown in step 120. In such examples, the process of preparing the poloxamer solution is performed in a separate vessel from the extractor. A skilled artisan will appreciate that the poloxamer can also be introduced as a solid into the extractor prior to mixing with the first alkanol. Thus, the process of preparing the poloxamer solution can be made directly in the extractor vessel.

The extractor is then pressurized and the extraction solvent is introduced into the extractor as shown in step 125 of process 100. The extraction solvent contains the supercritical liquid. Examples of supercritical liquids include, but are not limited to, carbon dioxide, methane, ethane, propane, ammonia, Freon®, water, ethylene, propylene, methanol, ethanol, acetone, and combinations thereof. In some embodiments, the supercritical liquid under pressure is a member selected from carbon dioxide, methane, ethane, propane, ammonia refrigerants sold as Freon®. In some embodiments, the supercritical liquid under pressure is carbon dioxide ($CO_2$).

The extraction occurs under high pressure and high temperature to maintain a supercritical liquid condition (e.g., supercritical carbon dioxide). Typically, these are kept constant. At this pressure and temperature, the supercritical liquid (e.g., supercritical carbon dioxide) is provided at a substantially constant flow rate. The flow rate can be varied between 0.5 kg/h to 600 kg/h, such as 1 kg/h to 400 kg/h, 1 kg/h to 250 kg/h, 1 kg/h to 100 kg/h, 1 kg/h to 50 kg/h, 1 kg/h to 20 kg/h, 1 kg/h to 10 kg/h, 10 kg/h to 400 kg/h, 10 kg/h to 250 kg/h, 10 kg/h to 100 kg/h, 10 kg/h to 50 kg/h, 10 kg/h to 20 kg/h, 20 kg/h to 400 kg/h, 20 kg/h to 250 kg/h, 20 kg/h to 100 kg/h, 20 kg/h to 50 kg/h, 50 kg/h to 400 kg/h, 50 kg/h to 250 kg/h, 50 kg/h to 100 kg/h, 100 kg/h to 400 kg/h, 100 kg/h to 200 kg/h or 200 kg/h to 400 kg/h, each inclusive. For example, the flow rate is 20 kg/h to 100 kg/h, inclusive, such as generally about or 100 kg/h.

Any suitable temperature that maintains the supercritical liquid in the supercritical state can be used to conduct the extraction processes. For example, the critical temperature of carbon dioxide is about 31° C. Thus, the extractor vessel is kept at a temperature greater than 31° C. In some embodiments, the extractor vessel has a temperature of 32° C. to 80° C., and generally about 32° C. to 60° C. or 32° C. to 60° C., each inclusive. For example, the temperature can be a temperature that is no more than 35° C., 36° C., 37° C., 38° C., 39° C., 40° C., 41° C., 42° C., 43° C., 44° C., 45° C., 50° C. or 60° C. Generally the temperature is greater than 31° C. but no more than 40° C. One of skill in the art will appreciate that the temperature can be varied, depending in part on the composition of the extraction solvent as well as the solubility of a given poloxamer in the solvents employed in the process.

Any suitable pressure can be used in the methods. When supercritical fluid extraction is employed, the system is pressurized at a level to ensure that the supercritical liquid remains at a pressure above the critical pressure. For example, the critical pressure of carbon dioxide is about 74 bars. Thus, the extractor vessel is pressurized to greater than 74 bars. The particular degree of pressure can alter the solubility characteristics of the supercritical liquid. Therefore, the particular pressure chosen can affect the yield and degree of extraction of impurities. Typically, the extractor vessel is pressurized in a range of 125 to 500 bars. In some embodiments, the extractor vessel is pressurized in a range of 200 bars to 400 bars, 200 bars to 340 bars, 200 bars to 300 bars, 200 bars to 280 bars, 200 bars to 260 bars, 200 bars to 240 bars, 200 bars to 220 bars, 220 bars to 400 bars, 220 bars to 340 bars, 220 bars to 300 bars, 220 bars to 280 bars, 220 bars to 260 bars, 220 bars to 240 bars, 240 bars to 400 bars, 240 bars to 340 bars, 240 bars to 300 bars, 240 bars to 280 bars, 240 bars to 260 bars, 260 bars to 400 bars, 260 bars to 340 bars, 260 bars to 300 bars, 260 bars to 280 bars, 280 bars to 400 bars, 280 bars to 340 bars, 280 bars to 300 bars or 300 bars to 340 bars. For example, the extraction vessel can be pressurized at about or at least 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, or 400 bars, but generally no more than 500 bars. The extraction vessel can be pressurized, for example, at 310±15 bars.

Typically, in the methods provided herein, the extraction solvent introduced into the extraction vessel also contains an alkanol. Thus, the extraction solvent includes a second alkanol and a supercritical liquid under high pressure and high temperature. The second alkanol acts as a co-solvent modifier of the supercritical liquid to change the solvent characteristics of the supercritical liquid and improve extractability of the solute in the method. Any suitable alkanol or combination of alkanols, as described above, can be used as the second alkanol in the methods provided herein. As described above, in particular examples, the second alkanol is methanol.

Any suitable combination of the second alkanol and the supercritical liquid, such as any described above, can be used in the extraction solvent in the methods. In some embodiments, the extraction solvent includes methanol and carbon dioxide. The second alkanol typically is provided as a percentage (w/w) of the total extraction solvent that is 3% to 20%, and generally 3% to 15%, for example 5% to 12%, 5% to 10%, 5% to 9%, 5% to 8%, 5% to 7%, 7% to 15%, 7% to 12%, 7% to 10%, 7% to 9%, 7% to 8%, 8% to 15%, 8% to 12%, 8% to 10%, 8% to 9%, 9% to 15%, 9% to 12%, 9% to 10%, 10% to 15% or 10% to 12%, each inclusive. The flow rate (kg/h) of the alkanol is a function of the amount of alkanol introduced into the extractor.

For example, a suitable ratio of the alkanol (e.g., methanol) to supercritical liquid (e.g., carbon dioxide) can be selected based on the identity and purity of the poloxamer starting material, or based on other extraction parameters such as temperature or pressure. For example, the ratio of alkanol (e.g., methanol) to supercritical liquid (e.g., carbon dioxide) can be from about 1:100 to about 20:100. In some embodiments, the ratio of alkanol (e.g., methanol) to supercritical liquid (e.g., carbon dioxide) is from about 1:100 to about 15:100. In some embodiments, the ratio of alkanol (e.g., methanol) to supercritical liquid (e.g., carbon dioxide) is from about 2:100 to about 14:100. The ratio of alkanol (e.g.) methanol to supercritical liquid (e.g., carbon dioxide) can be about 3:100, or about 4:100, or about 5:100, or about 6:100, or about 7:100, or about 8:100, or about 9:100, or about 10:100, or about 11:100, or about 12:100, or about 13:100, or about 14:100.

In certain aspects, the extraction can be conducted in an isocratic fashion, wherein the composition of the extraction solvent remains constant throughout the extraction procedure. For example, the amount of supercritical liquid (e.g., carbon dioxide) and alkanol (e.g., methanol) are constant over the time of extraction, for example, by maintaining a constant flow rate of each. Alternatively, the composition of the extraction solvent can be varied over time, typically, by altering (e.g., increasing or decreasing) the amount of the supercritical liquid and/or alkanol components that make up the extraction solvent. Generally, the supercritical liquid (e.g., carbon dioxide) is kept constant while the concentration of the alkanol (e.g., methanol) in the extraction solvent is altered (e.g., increased or decreased) over time of the extraction. The concentrations of the components can be altered by adjusting the flow rate.

In aspects in which the composition of the extraction solvent can be varied over time, a method in which the second alkanol is increased as the extraction process progresses, either as a step-wise gradient or continuously escalating gradient, is beneficial to the method. In certain instances, commercial grade poloxamers have both high molecular weight components and low molecular weight components along with the main product or component. Low alkanol (e.g., methanol) concentrations in high pressure carbon dioxide extraction fluid can selectively remove low molecular weight components. The solubility of impurity enriched extractables, however, is low and it takes time to significantly reduce the low molecular weight components making it less efficient. By increasing the alkanol concentration of the extraction solvent in a gradient fashion (either as a step-wise gradient or as a continuously escalating gradient), the amount of low molecular weight impurities that are extracted increases.

Also, higher alkanol (e.g., methanol) concentrations increase the solubility, and hence extraction, of higher molecular weight components. Thus, a gradient with successively higher alkanol (e.g., methanol) concentrations in the extraction solvent can progressively extract low molecular weight components, as well as eventually higher molecular weight components, or components that are less soluble. As a non-limiting example to illustrate this, it is believed that a lower alkanol (e.g., methanol) concentration of about 6.6% w/w can remove low molecular weight components. Increasing the concentration of alkanol by 1% to 3% will continue to effect extraction of low molecular weight components, but also result in removal of higher molecular weight components. A further increase in the concentration of alkanol by 1% to 3% will further remove these components as well as other components that have a higher molecular weight and/or were less soluble in the previous extraction solvents.

An extraction solvent with higher alkanol (e.g., methanol) concentrations, however, is not as selective because it provides more solubility for low molecular weight components, but also increases the solubility of other components including the main components. Therefore, the yield of purified product is reduced with high methanol concentrations. By increasing the concentration of the extraction solvent in a gradient fashion, as provided in methods herein, the reduction of poloxamer yield is minimized and the purity of the final product is maximized.

It was found that increasing the methanol concentration step-wise increases the loading capacity of the extractor, thereby increasing the throughput in a given extraction system. A two-phase system forms inside the extractor. A lower phase consists primarily of a mixture of poloxamer and methanol with some dissolved carbon dioxide. The extraction solvent (carbon dioxide with a lower methanol co-solvent fraction) permeates through the lower phase. An upper phase consists primarily of the extraction solvent and the components extracted from the poloxamer. The relative amount of the two phases depends upon methanol concentration in the solvent flow. In a typical extraction system there is adequate head space for proper phase separation of the upper phase. Increasing the methanol co-solvent concentration step-wise during the extraction process leads to higher feed charge into the extractor.

For example, returning to process 100, the composition of the extraction solvent can be varied as shown in steps 130-140. In some embodiments, the percentage of alkanol (e.g., methanol) by weight of the extraction solvent is increased over the course of the method. The methanol content in a methanol/carbon dioxide mixture can be increased in a stepwise fashion or a continuous fashion as the extraction process progresses. In some embodiments, for example, the extraction process for a poloxamer (e.g., P188) starts using about 3% to about 10% by weight (w/w) of an alkanol (e.g., methanol) in an extraction solvent with a supercritical liquid (e.g., carbon dioxide), such as about 5% to about 10%, such as 6% to 8% (e.g., about 6.6% or 7.4%). After a defined period, the alkanol (e.g., methanol) content of the extraction solvent is raised about 1-3%, such as 1-2% (e.g., to 7.6% or 9.1%, respectively). The alkanol (e.g., methanol) content is again subsequently raised about 1-3% such as 1-2% (e.g., to 8.6% or 10.7%, respectively) during a final period.

Any suitable solvent gradient can be used in the methods. For example, the alkanol (e.g., methanol) concentration in the supercritical liquid (e.g., carbon dioxide) can be increased from about 5% to about 20% over the course of extraction procedure. The alkanol (e.g., methanol) concentration in the supercritical liquid (e.g., carbon dioxide) can be increased from about 5% to about 20%, or from about 5% to about 15%, or from about 5% to about 10%. The alkanol (e.g., methanol) concentration in supercritical liquid (e.g., carbon dioxide) can be increased from about 6% to about 18%, or from about 6% to about 12%, or from about 6% to about 10%. The alkanol (e.g., methanol) concentration in supercritical liquid (e.g., carbon dioxide) can be increased from about 7% to about 18%, or from about 7% to about 12%, or from about 7% to about 10%. The alkanol (e.g., methanol) concentration can be increased in any suitable number of steps. For example, the alkanol (e.g., methanol) concentration can be increased over two steps, or three steps, or four steps, or five steps over the course of the extraction procedure. A skilled artisan will appreciate that other solvent ratios and solvent gradients can be used in the extraction processes.

Time of extraction of the process provided herein can be for any defined period that results in a suitable extraction of material in the preparation while minimizing reductions in poloxamer yield and maximizing purity. The time is a function of the choice of pressure, temperature, second alkanol concentration, and process of providing the extraction solvent (e.g., isocratic or as a gradient of increasing alkanol concentration as described herein). Generally, the extraction proceeds for 5 hours to 50 hours, and generally 10 hours to 30 hours, or 15 hours to 25 hours, each inclusive such as or about 15 hours or 24 hours. The higher the alkanol (e.g., methanol) concentration employed in the method, typically the shorter the time of the extraction. It also is understood that in examples in which a gradient of alkanol is employed in the method, the total time of extraction is divided as a function of the number of gradient steps in the procedure. The extraction in each gradient step can be for the same amount of time or for different times. It is within the level of a skilled artisan to empirically determine the times of extraction to be employed. Samples can be collected during the extraction process to monitor the removal of substances or to determine if adjustment of extraction parameters, such as temperature or the composition of the extraction solvent, is necessary.

In particular, the methods can be used to purify P188. The process can be applied to other polymers as well. For example, in some embodiments, the methods provided herein provide a method for preparing a purified polyoxypropylene/polyoxyethylene composition. The method includes:

a) providing or introducing a polyoxypropylene/polyoxyethylene block copolymer solution into an extractor vessel that is dissolved in a first solvent to form the copolymer solution, wherein the first solvent is methanol, ethanol, propanol, butanol, pentanol or a combination thereof, and the composition comprises:

i) a polyoxypropylene/polyoxyethylene block copolymer having the formula $HO(CH_2CH_2O)_a$—$[CH(CH_3)CH_2O]_b$—$(CH_2CH_2O)_aH$, the mean or average molecular weight of the copolymer is from about 4,000 to about 10,000 Da; and ii) a plurality of low molecular weight substances having a molecular weight of less than 4,500 Da, wherein the plurality of low molecular weight substances constitutes more that 4% of the total weight of the composition;

b) adding a second solvent to form an extraction mixture, wherein the second solvent contains a supercritical liquid under high pressure and high temperature and an alkanol that is methanol, ethanol, propanol, butanol, pentanol or a combination thereof, and the concentration of the second solvent in the extraction solvent is increased over the time of extraction method; and c) allowing the extraction mixture to separate to form a plurality of phases comprising a raffinate phase and an extract phase, wherein the raffinate phase and extract phase are separately removed or isolated.

In some cases of the above method, the mean or average molecular weight of the copolymer is from about 7,680 to 9,510 Da, such as generally 8,400-8,800 Da, for example about or at 8,400 Da. In the method, the copolymer solution can be formed in the extractor vessel by the addition of the copolymer and by adding a first solvent to form a solution or a suspension of the copolymer, wherein the first solvent comprises an alkanol selected from the group consisting of methanol, ethanol, propanol, butanol, pentanol and a combination thereof. Alternatively, the addition of the first solvent to the copolymer to form a copolymer solution can be in a separate vessel and the copolymer solution, which is dissolved in the first solvent, is provided or introduced (i.e. charged) into the extractor vessel. In some cases, prior to step c) the method includes stirring the extraction mixture under high pressure and high temperature to extract impurities (e.g., low molecular weight extractable components and other components) from the copolymer composition.

2. High Pressure Methods

The method provided herein to purify a poloxamer (e.g., P188) can be a high pressure fluid extraction method with mixed solvent systems. One of the solvents in the mixed system is a gaseous solvent that can be compressed to liquid at moderate pressures, such as carbon dioxide. For example, the solvent power of methanol or ethanol can be modified with high pressure carbon dioxide (although not necessarily supercritical carbon dioxide i.e., sub-critical) to give the precise solvating power required to selectively remove different fractions of poloxamers.

In such a method, the extraction solvent contains carbon dioxide that is provided under sub-critical conditions, as well as another solvent that is increased over time in the extraction. Accordingly, some embodiments of methods provided herein provide an extraction method for removing impurities in a poloxamer preparation (e.g., low molecular weight components), wherein the method includes:

a) providing or introducing a poloxamer into an extractor vessel that is dissolved in a first solvent to form a solution, wherein the first solvent is selected from among alcohols, aliphatic ketones, aromatic ketones, amines, and mixtures thereof;

b) admixing an extraction solvent with the solution to form an extraction mixture, wherein the extraction solvent comprises high-pressure carbon dioxide and the solvent, and the concentration of the solvent in the extraction solvent is increased over the time of extraction method; and c) removing the extraction solvent from the extractor vessel to thereby remove the low molecular weight impurities from the poloxamer.

The first and second solvent can be the same or different. In the method, the step of dissolving the poloxamer solution in the first solvent can occur prior to providing or introducing the solution into an extraction vessel or at the time of providing or introducing the solution into an extraction vessel. For example, the poloxamer is dissolved in a separate vessel and then the solution is added to the extraction vessel.

In aspects of the method, the extraction solvent is under sub-critical conditions. In this process, one of the solvents is preferably a gas at room temperature (or close to room temperature) that can be compressed to a liquid at high pressures. Suitable gases that can be compressed to liquids are carbon dioxide, methane, ethane, propane, ammonia, and freon. A typical solvent pair is chosen in such a way that one is a solvent for the component to be removed by extraction, while the other liquid is a non-solvent, or vice-versa. The solvating capacity of the solvent pair is primarily controlled by the ratio of the solvents in the mixture. By passing the solvent pair through the product containing the substances, the relatively more soluble component can be extracted. Gaseous solvents can be pressurized at any suitable sub-critical pressure. For example, carbon dioxide can be employed at a pressure of from about 25 bars to about 100 bars. The pressure can be about 25, 30, 35, 40, 45, 50, 55, 60, 65, 70, 75, 80, 85, 90, 95, or 100 bars. In some embodiments, the pressure is from about 60 to about 85 bars. In some embodiments, the pressure is about 75 bars.

Any suitable temperature can be used to conduct the extraction processes. In some embodiments, the extractor vessel has a temperature of 10° C. to 80° C. The temperature can be, for example, about 10° C., or about 15° C., or about 20° C., or about 25° C., or about 30° C., or about 35° C., or about 40° C., or about 45° C., or about 50° C., or about 55° C., or about 60° C., or about 65° C., or about 70° C., or about 75° C., or about 80° C. In some embodiments, the extractor vessel has a temperature of from about 20° C. to about 50° C. When purifying poloxamer 188, for example, the extractor vessel can have a temperature of from about 20° C. to about 60° C. (e.g., about 40° C.). Other temperatures can be suitable for purification of poloxamer 188 depending on the extraction apparatus and the chosen extraction parameters. One of skill in the art will appreciate that the temperature can be varied, depending in part on the composition of the extraction solvent as well as the solubility of a given poloxamer in the solvents employed in the process.

Similar to supercritical fluid extraction methods discussed above, the extraction can be conducted in an isocratic fashion, wherein the composition of the extraction solvent remains constant throughout the extraction procedure. For example, the amount of carbon dioxide and solvent (e.g., methanol) in the extraction solvent are constant over the time of extraction, for example, by maintaining a constant flow rate of each. Alternatively, the composition of the extraction solvent can be varied over time, typically by altering (e.g., increasing or decreasing) the amount of the carbon dioxide and/or other solvent (e.g., methanol) that make up the extraction solvent. Generally, the carbon dioxide is kept constant while the concentration of the other solvent (e.g., methanol) in the extraction solvent is altered (e.g., increased or decreased) over time of the extraction. The concentrations of the components can be altered by adjusting the flow rate. The particular concentration of solvent, and the gradient of concentrations employed, can be similar to those discussed above with respect to the supercritical extraction methods. It is within the level of a skilled artisan to adjust concentrations and extraction time appropriately to achieve a desired purity or yield.

Samples can be collected during the extraction process to monitor the removal of substances or to determine if adjustment of extraction parameters, such as temperature or the composition of the extraction solvent, is necessary.

In particular, the methods can be used to purify P188. The process can be applied to other polymers as well. The benefits of the mixed solvent system include effective removal of high molecular weight (HMW) substances and/or low molecular weight (LMW) substances using the mixed system.

In certain embodiments, the provided methods provide a method for preparing a purified polyoxypropylene/composition. The method includes:

a) providing or introducing a polyoxypropylene/polyoxyethylene block copolymer composition into an extractor vessel that is dissolved in a first solvent to form the copolymer solution, wherein the first solvent is an alcohol, aliphatic ketone, aromatic ketone, amines and mixtures thereof, and the composition contains:

i) a polyoxypropylene/polyoxyethylene block copolymer wherein the mean or average molecular weight of the copolymer is from about 4,000 to about 10,000 Da; and ii) a plurality of low molecular weight substances having a molecular weight of less than 4,000 Da, wherein the plurality of low molecular weight substances constitutes more that 4% of the total weight of the composition;

b) adding a second solvent to form an extraction mixture, wherein the second solvent comprises high-pressure carbon dioxide and the first solvent, and the concentration of the first solvent in the extraction solvent is increased over the time of extraction method; and c) allowing the extraction mixture to separate to form a plurality of phases including a raffinate phase and an extract phase, and the raffinate phase and extract phase are separately removed or isolated.

When the poloxamer is a poloxamer 188 that is purified, the mean or average molecular weight of the copolymer is from about 7,680 to 9,510 Da, such as generally 8,400-8,800 Da, for example about or at 8,400 Da. In the method, the copolymer solution can be formed in the extractor vessel by the addition of the copolymer and by adding a first solvent to form a solution or a suspension of the copolymer, wherein the first solvent comprises an alkanol selected from the group consisting of methanol, ethanol, propanol, butanol, pentanol and a combination thereof. Alternatively, the addition of the first solvent to the copolymer to form a copolymer solution can be in a separate vessel and the copolymer solution, which is dissolved in the first solvent, is provided or introduced (i.e. charged) into the extractor vessel. In some cases, prior to step c) the method includes stirring the extraction mixture under high pressure and high temperature to extract impurities (e.g., low molecular weight extractable components and other components) from the copolymer composition.

In certain aspects, this approach does not have the density variation and permeability characteristics of the supercritical fluid extraction process. However, the solvent recycling is easy and energy efficient. In a typical high pressure extraction, the exit stream containing the extracted component is subjected to lower pressure that causes phase separation and separation of the more volatile solvent as a gas. This leaves the other solvent enriched with the extracted component. The extraction process continues until the extractable component is substantially depleted from the mixture. The gaseous solvent is compressed back into liquid and is available for continued extraction. This solvent recycling process is efficient because the compressible solvent is selected to have complete separation from the solvent mixture with minimum change in the pressure.

c. Extraction Vessel and System

Figure 4:
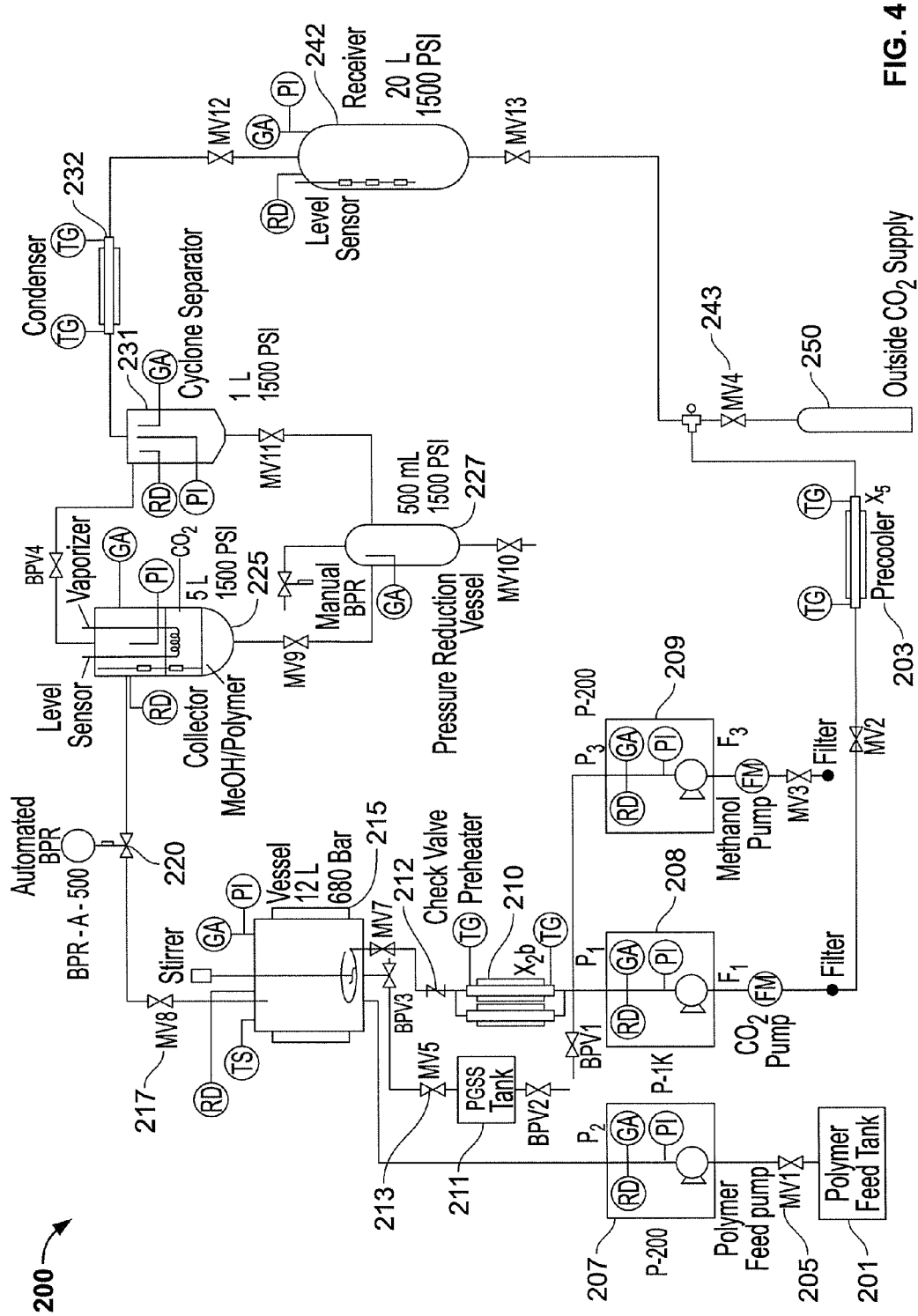
FIG. 4 shows an extraction apparatus useful in the methods provided herein.
Figure 6A:
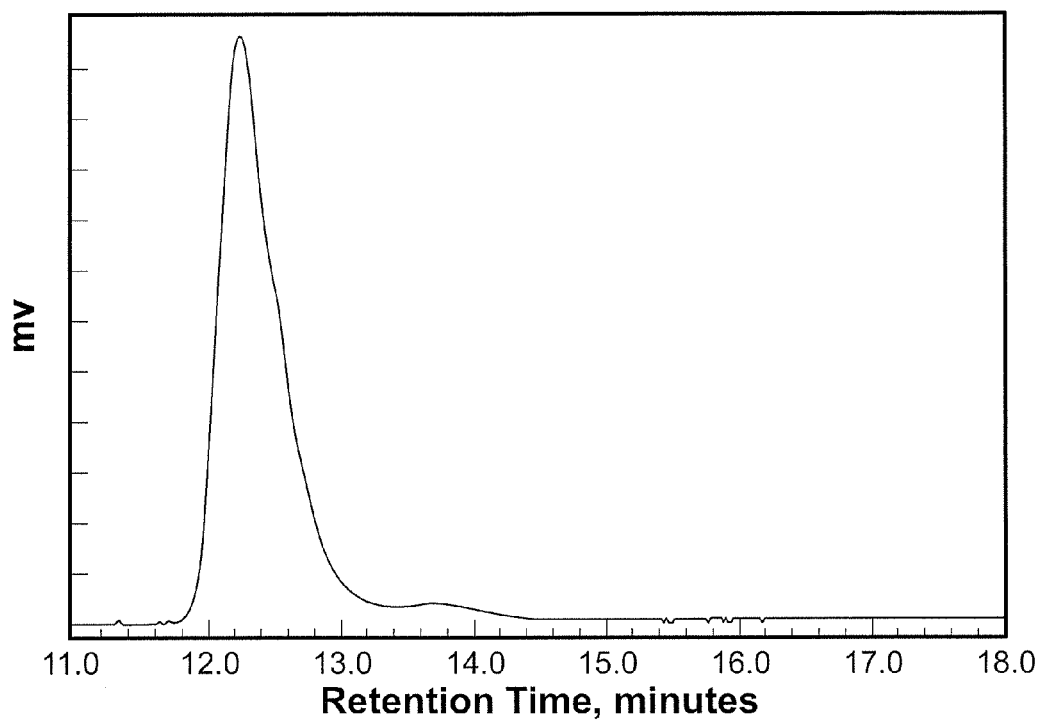
FIG. 6A-B shows a gel permeation chromatography (GPC) comparison of low molecular weight substance content in a commercially available poloxamer 188 (Panel A) versus a material purified according to an embodiment provided herein (Panel B).
Figure 6B:
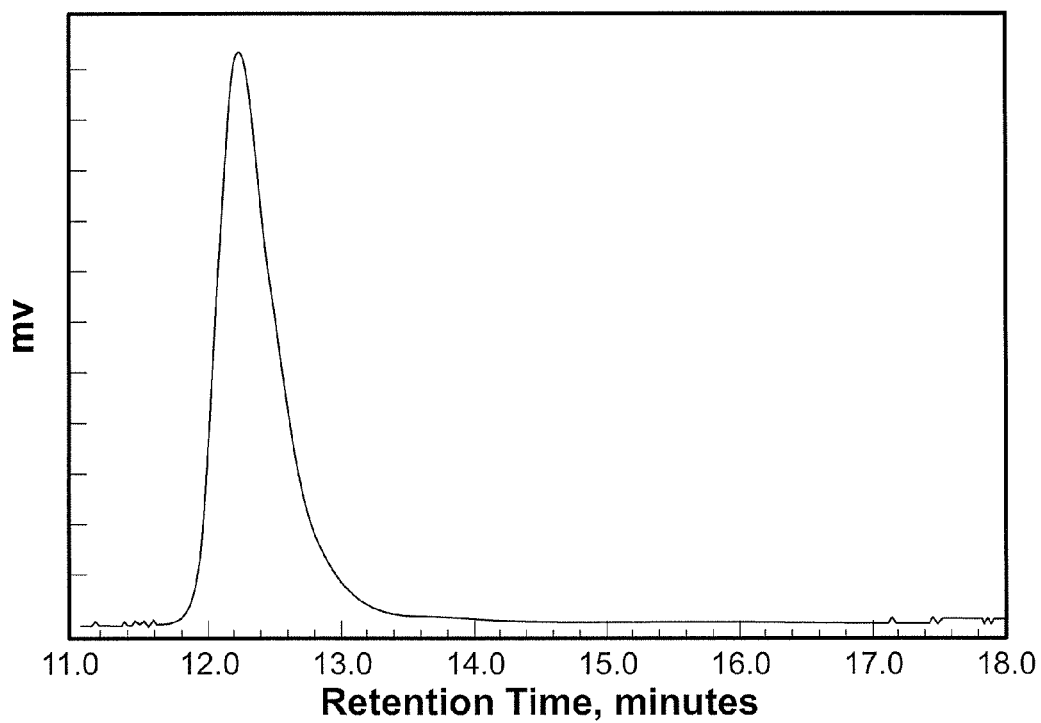

For any of the methods provided herein, system 200 in FIG. 4 represents one embodiment for practice of the provided methods. System 200 is one system that can be used to extract impurities (e.g., LMW substances and/or other components) from the poloxamers using supercritical fluids or sub-supercritical methods. Polymer feed pump 201 is charged with a poloxamer (e.g., P188) to be purified. Poloxamer is transported into polymer feed tank 207 through valve 205. The extractor vessel 215 is used to remove the extracted impurities from the sample, such as LMW substances or other components from the poloxamer. Carbon dioxide (or other supercritical liquid or sub-supercritical liquid) pump 208 is charged with carbon dioxide from outside carbon dioxide supply 250 through valve 243 and pre-cooler 203. Carbon dioxide is pumped from pump 208 into heat exchanger 210 and then into extractor 215. Methanol (or other suitable solvents) is pumped into extractor 215 through pump 209. In such embodiments, methanol and carbon dioxide extract impurities, such as LMW substances or other components, from the poloxamer in extractor 215. After extraction, the purified poloxamer mixture is discharged and collected via rapid depressurization processing. The extracted components are isolated from the solvent stream using collector 225, pressure reduction vessel 227, and cyclone separator 231. Carbon dioxide vapor released during collection in collector 225 can be liquefied and recycled using condenser 232.

In some embodiments, the extraction apparatus can include a solvent distribution system that contains particles of certain shapes forming a "fluidized" bed at the bottom of the extraction vessel. The bed can be supported by a screen or strainer or sintered metal disk. The particles used for the bed can be either perfectly shaped spheres or particles of irregular shape, such as pebbles. Having a smooth surface with less porosity or less surface roughness is preferred for easy cleaning. These advantages can be validated in a pharmaceutical manufacturing process.

The density of the particles forming the bed is selected to be higher than the solvent density so the bed remains undisturbed by the incoming solvent flow during the extraction process. The size of the particles can be uniform or can have a distribution of different sizes to control the packing density and porosity of the bed. The packing distribution arrangement is designed to provide for balanced, optimum extraction and subsequent coalescence of the solvent particles before exiting the extraction vessel. This facilitates maximum loading of the extractor with poloxamer charge. This can also maximize extraction efficiency, minimize the extraction time, and minimize undesirable carry-over of the purified product out of the extraction vessel.

The size of the spheres in the bed is selected based on one or more system properties including the dimensions of the extraction vessel, the residence time of the solvent droplets in the extraction vessel, and the ability of the solvent droplets to coalesce. The diameter of the spheres can range from about 5 mm to about 25 mm. The diameter can be an average diameter, wherein the bed contains spheres of different sizes. Alternatively, all of the spheres in the bed can have the same diameter. An example of the cross section of stainless steel spheres of different sizes in a solvent distribution bed is shown in FIG. 5.

Accordingly, an efficient solvent extraction apparatus is provided. The apparatus includes:

a) a distribution system at the bottom of the extractor, wherein the distribution system comprises a plurality of spheres; and b) a particle coalescence system at the top of the extractor.

In some embodiments, the plurality of spheres includes metallic spheres, ceramic spheres, or mixtures thereof. In some embodiments, the plurality of spheres are the same size. In some embodiments, the plurality of spheres include spheres of different sizes. In some embodiments, the particle coalescence system includes one or more members selected from a demister pad, a static mister, and a temperature zone.

d. Extraction and Removal of Extractants

Any of the methods provided herein can be performed as a batch method or as a continuous method. In some embodiments, the method is a batch method. A batch method can be performed with extraction vessels of various dimensions and sizes as described above. For example, the equipment train can contain a 120-L high pressure extractor. A poloxamer (e.g., P188) solution, which is a poloxamer dissolved in an appropriate solvent (e.g., an alkanol solvent, such as methanol), is provided or introduced into the extraction vessel. The extraction solvents, such as any described in the methods above (e.g., supercritical or high-pressure carbon dioxide and methanol) are independently and continuously pumped into the extraction vessel maintained at a controlled temperature, flow, and pressure. Substances are removed by varying the extraction solvent composition as described herein. Alternatively, the extraction process conditions such as temperature and pressure can also be varied independently or in combination. As described below, after substances are removed, the purified product is discharged into a suitably designed cyclone separator to separate the purified product from carbon dioxide gas. The product is dried to remove the residual alkanol solvent.

In some embodiments, the extraction method is a continuous method. In a typical continuous extraction, a poloxamer (e.g., P188) solution, which is a poloxamer dissolved in an appropriate solvent (e.g., an alkanol solvent, such as methanol), is loaded at the midpoint of a high pressure extraction column packed with a suitable packing material. The extraction solvent is pumped through the extraction column from the bottom in counter current fashion. The extracted material, such as LMW substances or other components, are removed at the top of the column while purified product is removed from the bottom of the column. The purified product is continuously collected at the bottom of the extractor column and periodically removed and discharged into a specially designed cyclone separator. The purified polymer particles containing residual methanol are subsequently dried under vacuum.

Depending on the level of purity desired in the purified poloxamer product, the extraction step can be repeated for a given batch. That is, additional portions of the extraction solvent can be introduced into the extractor vessel and removed until a sufficient level of poloxamer purity is obtained. Accordingly, some embodiments of methods provided herein provide extraction methods as described above, wherein after step c, the method further includes repeating steps b and c. Steps b and c can be repeated until the poloxamer is sufficiently pure. For example, steps b and c can be repeated one time, or two times, or three times, or four times, or five times, or in an iterative fashion.

When the poloxamer material is sufficiently pure, the product is prepared for further processing. In some embodiments, the product is handled according to process 100 as summarized in FIG. 1. The product can be discharged from the extractor vessel and collected in an appropriate receiver, as shown in step 145. The wet product can be sampled for testing with respect to purity, chemical stability, or other properties, as shown in step 150. The product can be dried by removing residual solvents under vacuum. Vacuum level can be adjusted to control drying rates. Drying can be conducted at ambient temperature, or at elevated temperatures if necessary. In general, the drying temperature is held below the melting point of the poloxamer. The wet product can be dried in a single lot or in smaller portions as sub-lots. As shown in steps 160-170, drying of the product can be initiated, for example on a sub-lot, under vacuum at ambient temperature. Drying can be then continued at higher temperatures and lower pressures as the process progresses. If necessary, for example if collection was made in sub-lots, any remaining portions of the wet product can be processed in a similar manner, as shown in step 175 of process 100. The resulting product, such as the various sub-lots that have been combined, are mixed in a suitable container, as shown in step 180, and the resulting product can be characterized, stored, transported, or formulated.

Advantageously, the methods disclosed herein effectively recycle carbon dioxide. In particular, supercritical carbon dioxide or high-pressure carbon dioxide can be recovered by subjecting the extract phase to changes in temperature and pressure. In certain embodiments, the methods employed herein have recycling efficiencies of greater than 80%, preferably greater than 90%, and preferably greater than 95%.

In any of such methods, the methods provided herein (see, e.g., steps a)-c) above), the extract phase can be further processed. The methods further can include: passing the extract phase to a system consisting of several separation vessels; isolating the impurities (e.g., low molecular-weight impurities); processing the purified material or raffinate; and recovering the compressed carbon dioxide for reuse.

In any of the methods provided herein, various parameters can be assessed in evaluating the methods and resulting products. For example, parameters such as methanol concentration, gradient profile, temperature, and pressure can be assessed for process optimization. Processes and suitable conditions for drying wet raffinate, such as vacuum level, mixing mode, time, and temperature, also can be assessed.

e. Exemplary Methods for Preparation of Purified Poloxamers

The methods provided herein above result in the generation of particular purified poloxamer preparations, and in particular LCMF P188 preparations. In particular, the methods provided herein can be used to purify a P188 copolymer as described herein that has the formula: $HO(CH_2CH_2O)_{a'}-(CH_2CH(CH_3)O)_{b}-(CH_2CH_2O)_{a}H$, and a mean or average molecular weight of the copolymer that is from 7,680 to 9,510 Da, such as generally 8,400-8,800 Da, for example about or at 8,400 Da, and that contains a plurality of low molecular weight substances having a molecular weight of less than 4,000 Da, wherein the plurality of low molecular weight substances constitutes more that 4% of the total weight of the composition.

In some embodiments, the present methods generate purified poloxamers with less than about 4% low molecular weight components such as less than about 3%, 2% or 1%. Typically, the low molecular weight components include glycols, and volatile degradation impurities such as formaldehyde, acetaldehyde, propionaldehyde, acetone, methanol, and peroxides. In certain instances, the processes herein produce poloxamer substantially free of low molecular weight components, i.e., less than 4%, 3%, 2% or 1% of the foregoing components. The methods also can produce poloxamer substantially free of long circulating material, such that when the purified poloxamer is administered to a subject, there are no components in the poloxamer that are or give rise to a material that has a longer half-life in the blood or plasma more than 5.0-fold the half-life of the main component in the poloxamer distribution, such as generally no more than 4.0-fold, 3.0-fold, 2.0-fold, or 1.5-fold. The following discussion details an exemplary of method that produces such purified poloxamer.

i. Removal of Low Molecular Weight (LMW) Components

Figure 2:
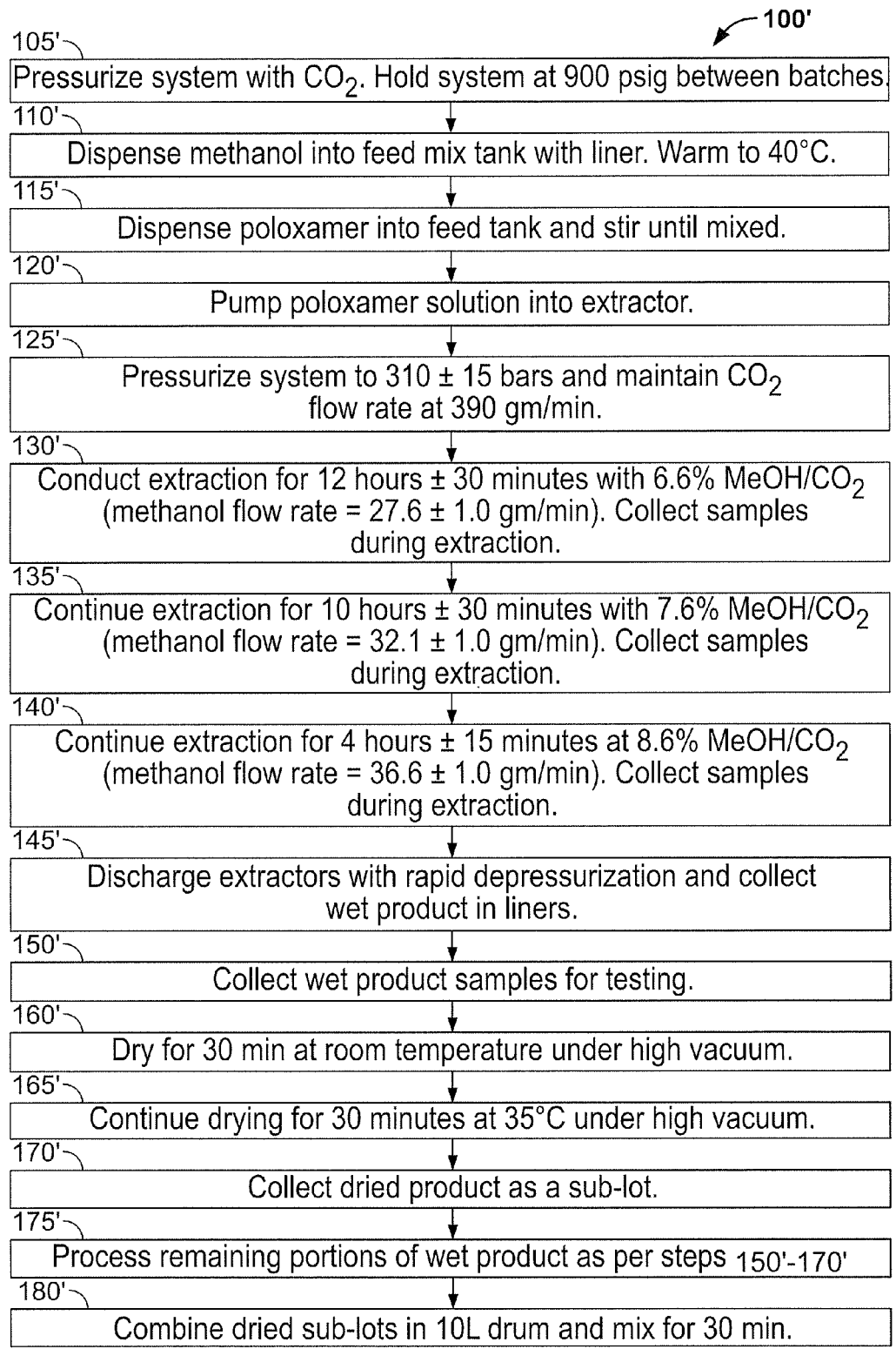
FIG. 2 is a specific exemplary process 100' for preparing a poloxamer, such as poloxamer 188, using the methods described herein.

FIG. 2 depicts certain embodiments of the methods herein that provide a process 100' that is useful for removing LMW substances in a poloxamer. The extraction system is pressurized, as shown in step 105', prior to dispensing a first alkanol (e.g., methanol) into the feed mix tank, as shown in step 110'. The system is heated to a temperature suitable for the extraction process, which is a temperature above the critical temperature of carbon dioxide used in the process that is about 31° C. Typically, the temperature is no more than 40° C. The temperature is generally kept constant through the process.

The first alkanol (e.g., methanol) is used to form a poloxamer solution according to step 115' in process 100'. In this process, dispensing of a P188 poloxamer into the feed tank with the alkanol (e.g., methanol,) results in a P188 poloxamer solution that is dissolved in the alkanol (e.g., methanol). The amount of poloxamer for use in the method can be any amount, such as any amount described herein above. After forming a poloxamer/alkanol mixture, all or part of the mixture is pumped into the extractor as shown in step 120'. In some cases, the poloxamer solution can be formed in the extraction vessel by introducing the poloxamer as a solid into the extractor prior to mixing with the alkanol.

The extractor is then pressurized and the extraction solvent is introduced into the extractor as shown in step 125' of process 100'. The extraction solvent typically contains carbon dioxide and extraction is performed at a temperature greater than the critical temperature of 31° C. as described above and under high pressure greater than the critical pressure of 74 bars. For example, in an exemplary method, the extraction vessel is pressurized to about 310±15 bars, and the carbon dioxide is provided at a flow rate that is 20 kg/h to 50 kg/h, such as generally about or approximately 24 kg/h (i.e. 390 g/min).

The extraction then is conducted in the presence of a second alkanol acting as a co-solvent modifier of the carbon dioxide. The second alkanol, such as methanol, is added in a gradient step-wise fashion such that the concentration of the second alkanol in the extraction solvent is increased over the time of extraction method. For example, the composition of the extraction solvent can be varied as shown in steps 130'-140'. For example, as shown in step 130', the extraction process for a poloxamer (e.g., P188) starts using about 5% to 7%, by weight (w/w) of an alkanol (e.g., methanol) in an extraction solvent with a supercritical liquid (e.g., carbon dioxide), (e.g., about 6.6%). After a defined period, the alkanol (e.g., methanol) content of the extraction solvent is raised about 1-3%, such as 1% (e.g., to 7.6%). The alkanol (e.g., methanol) content is again subsequently raised about 1-3% such as 1 (e.g., to 8.6%) during a final period. The total time of the extraction method can be 15 hours to 25 hours. Each gradient is run for a portion of the total time.

For a commercially efficient purification process, it desirable to have successively increasing methanol concentrations where the profile is suitably modified to selectively remove most of the low molecular weight components. Residual low molecular weight components can be subsequently removed with high methanol concentrations in a short time. Therefore a stepwise methanol concentration profile where about a 5-10% (e.g., 6.6%) methanol is used for 12 hours, a higher methanol is used for 10 hours and finally an even higher methanol is used for 4 hours to produce purified product in high yields without significantly reducing the overall yield and not enriching the high molecular weight components.

When the poloxamer material is sufficiently pure, the product is prepared for further processing as shown in process 100'. The product can be discharged from the extractor vessel and collected in an appropriate receiver, as shown in step 145'. The wet product can be sampled for testing with respect to purity, chemical stability, or other properties, as shown in step 150'. The product can be dried by removing residual solvents under vacuum as described herein. In an exemplary method as shown in steps 160'-170', drying can be initiated with a sub-lot under vacuum at ambient temperature and drying can be then continued at higher temperatures and lower pressures as the process progresses. Remaining sub-lots can be processed in a similar manner, as shown in step 175' of process 100. Sub-lots can be combined and mixed in a suitable container, as shown in step 180; and the resulting product can be characterized, stored, transported, or formulated.

ii. Preparation of Long Circulating Material Free (LCMF) Poloxamer

Figure 3:
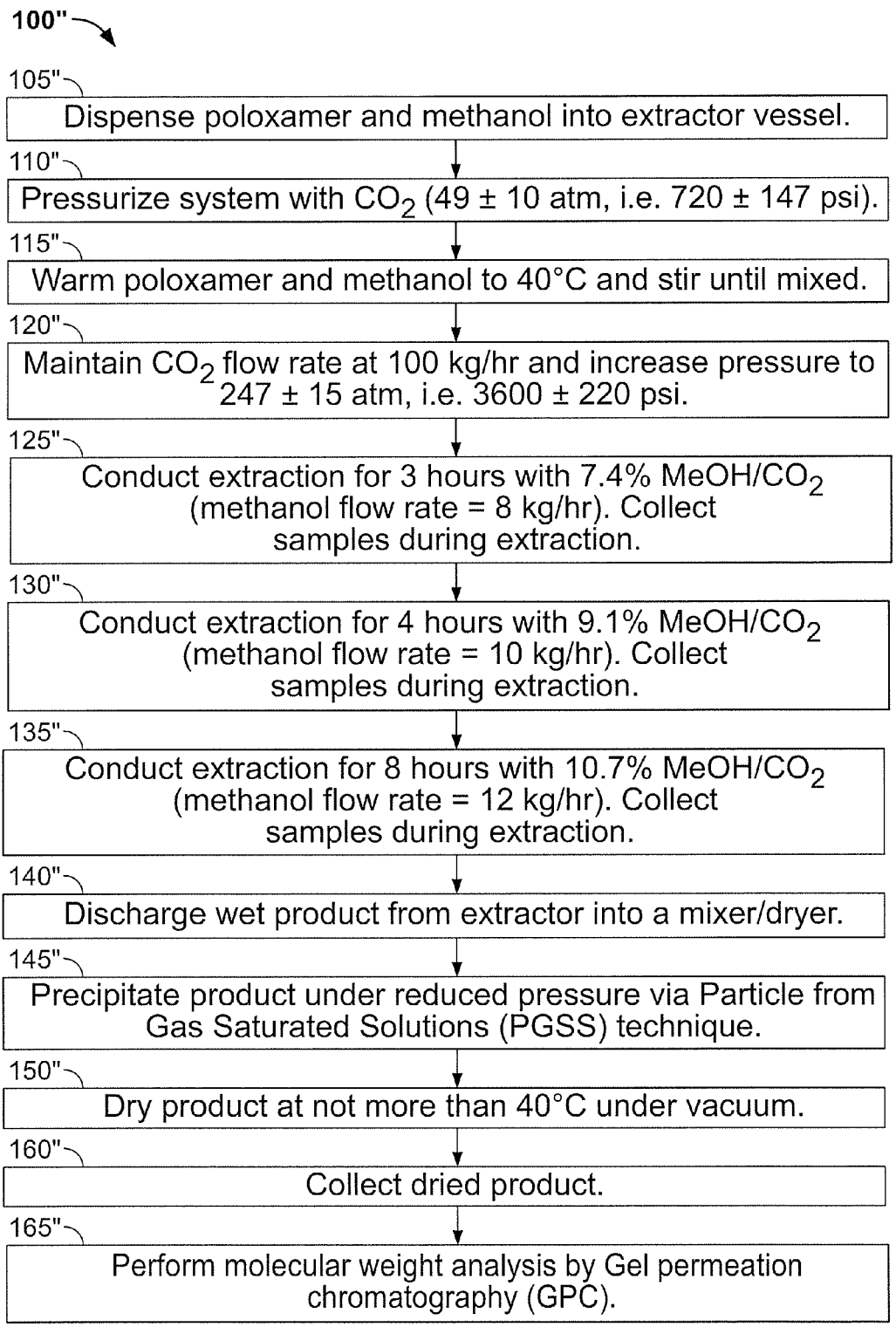
FIG. 3 is a specific exemplary process 100" for preparing a poloxamer, such as poloxamer 188, using methods described herein.

FIG. 3 depicts embodiments for preparation of LCMF poloxamer. Certain embodiments of the methods herein provide a process 100" that generates a poloxamer that does not contain any components that, after administration to a subject, results in a long circulating material in the plasma or blood as described herein. As shown in step 105", the poloxamer and first alkanol (e.g., methanol) are dispensed into the extractor vessel and to form the poloxamer solution. In this process, dispensing of a P188 poloxamer into the extraction vessel with the alkanol (e.g., methanol,) results in a P188 poloxamer solution that is dissolved in the alkanol (e.g., methanol). The amount of poloxamer for use in the method can be any amount as described herein. In some cases, the poloxamer solution can be formed a separate vessel, and the poloxamer solution transferred to the extractor vessel.

The extraction system is pressurized, as shown in step 110", after dispensing a first alkanol (e.g., methanol) and poloxamer. As shown in step 115", the system is heated to a temperature suitable for the extraction process, which is a temperature above the critical temperature of carbon dioxide used in the process, that is about 31° C. Typically, the temperature is between 35° C. and 45° C. The temperature is generally kept constant through the process. The poloxamer solution is formed under pressurized carbon dioxide of about 49 bars and a temperature of between 35° C. to about or at 45° C. for a defined period, generally less than several hours.

The extractor then is pressurized and the extraction solvent is introduced into the extractor as shown in step 120" of process 100'". The extraction solvent typically contains carbon dioxide and a second alkanol and extraction is perform at a temperature greater than the critical temperature of 31° C., as described above, and under high pressure, greater than the critical pressure of 74 bars. For example, in an exemplary method, the extraction vessel is pressurized to about 247±15 atm bars (range between 240 bars and 260 bars), and the carbon dioxide is provided at a flow rate that is 50 kg/h to 120 kg/h, inclusive, such as generally about or approximately 100 kg/h.

The extraction is conducted in the presence of the second alkanol, which acts as a co-solvent modifier of the carbon dioxide. As shown in steps 125"-135", the second alkanol, such as methanol, is added in a gradient step-wise fashion such that the concentration of the second alkanol in the extraction solvent is increased over the time of extraction method. For example, the composition of the extraction solvent can be varied as shown in steps 125"-135". For example, as shown in step 125", the extraction process for a poloxamer (e.g., P188) starts using about 7% to 8% (e.g., about or 7.4%), by weight (w/w) of an alkanol (e.g., methanol) in an extraction solvent with a supercritical liquid (e.g., carbon dioxide). After a defined period, the alkanol (e.g., methanol) content of the extraction solvent is raised about 1-3%, such as up to 2% (e.g., to 9.1%). The alkanol (e.g., methanol) content is again subsequently raised about 1-3% such as up to 2% (e.g., to 10.7%) during a final period. The total time of the extraction method can be 15 hours to 25 hours, inclusive. Each gradient is run for a portion of the total time.

For an extraction process that removes components other than low molecular weight components, including components that, when administered, give rise to long circulating forms, it desirable to have a process that maximizes the purity and removal of these components while minimizing reductions in yield. It is found that successively increasing alkanol (e.g., methanol) concentrations when starting from a higher concentration of alkanol (e.g., methanol) than in other methods, generally starting at 7% to 8% by weight, the profile is suitably modified to selectively remove these components and low molecular weight components, while minimizing reductions in yield. For example, such an exemplary method can produce yields greater than 55%, and generally greater than 60% or 65%. Residual low molecular weight components can be subsequently removed with high methanol concentrations in a short time. Therefore a stepwise methanol concentration profile where about a 7-8% (e.g., 7.4%) methanol is used for about 3 hours, a higher methanol (e.g., 9.1%) is used for about 4 hours and finally an even higher methanol (e.g., 10.7%) is used for about 8 hours produces a purified product in high yields without significantly reducing the overall yield.

When the poloxamer material is sufficiently pure, the product is prepared for further processing as shown in process 100'". The product can be discharged from the extractor vessel and collected in an appropriate receiver, as shown in step 140". The product can be precipitated under reduced pressure via particles from gas saturated solutions (PGSS) techniques as shown in step 145". The product can be dried by removing residual solvents under vacuum as described herein. In an exemplary method, as shown in steps 150"-165", drying can be initiated under vacuum at high temperatures of between 35° C. to 45° C. The dried product can be collected as shown in step 160". The resulting product can be characterized, stored, transported, or formulated as shown in step 165".

iii. Methods for Confirming the Identity of LCMF Poloxamers

To confirm that a poloxamer 188 preparation made by the methods herein or other methods, is an LCMF poloxamer 188, the properties of the poloxamer can be assessed. The properties include, but are not limited to, the absence of a long circulating material upon administration to a human or an animal model, the behavior of the poloxamer in reverse phase (RP)-HPLC compared to a preparation of poloxamer that contains the LCM material such as the poloxamer described in U.S. Pat. No. 5,696,298 and commercially available poloxamer 188 (e.g., those sold under the trademarks Pluronic® F-68, Flocor®, Kolliphor® and Lutrol®, and the behavior in RP-HPLC under the conditions exemplified herein (see i.e., Example 1). Any method that confirms that the preparation lacks LCM material can be used.

D. Pharmaceutical compositions, dosages and Administration

Compositions containing a poloxamer P188, such as any prepared by methods provided herein, are provided. In particular, provided herein are compositions containing an LCMF poloxamer, particularly an LCMF poloxamer P188. The compositions are used for and used in methods for treating heart failure as described in Section F and throughout the disclosure.

1. Formulations

Pharmaceutical compositions containing P'88, such as LCMF P188 or other suitable poloxamer, can be formulated in any conventional manner by mixing a selected amount of the poloxamer with one or more physiologically acceptable carriers or excipients to produce a formulation. Selection of the formulation, carrier and/or excipient is within the skill of the administering professional and can depend upon a number of parameters. These include, for example, the mode of administration (i.e., intravenous, oral, nasal, pulmonary, local, topical, or any other mode) and the symptom, disorder, or disease to be treated.

Effective concentrations of P-188 or LCMF P-188 or other poloxamer, are mixed with a suitable pharmaceutical carrier or vehicle for intravenous, topical or local administration. Pharmaceutical carriers or vehicles suitable for administration of the copolymers include any such carriers known to those skilled in the art to be suitable for the particular mode of administration. Pharmaceutical compositions that include a therapeutically effective amount of P-188 or LCMF P-188, also can be provided as a lyophilized powder that is reconstituted, such as with sterile water, immediately prior to administration.

The compound can be suspended in micronized or other suitable form or can be derivatized to produce a more soluble active product. The form of the resulting mixture depends upon a number of factors, including the intended mode of administration and the solubility and bioavailability of P-188 or LCMF or other suitable poloxamer, in the selected carrier or vehicle. The resulting mixtures are solutions, suspensions, emulsions and other such mixtures, and can be formulated as an non-aqueous or aqueous mixtures, creams, gels, ointments, emulsions, solutions, elixirs, lotions, suspensions, tinctures, pastes, foams, aerosols, irrigations, sprays, suppositories, bandages, or any other formulation suitable for intravenous, topical or local administration. For intravenous administration, the poloxamer, such as the P-188 of LCMF P-188 can be formulated as a solution in an aqueous-based medium, such as isotonic, citrate buffered saline for internal administration.

Generally, pharmaceutically acceptable compositions are prepared in view of approvals for a regulatory agency or are prepared in accordance with generally recognized pharmacopeia for use in animals and in humans. Pharmaceutical compositions can include carriers such as a diluent, adjuvant, excipient, or vehicle with which an isoform is administered. Such pharmaceutical carriers can be sterile liquids, such as water and oils, including those of petroleum, animal, vegetable or synthetic origin, such as peanut oil, soybean oil, mineral oil, and sesame oil. Water is a typical carrier when the pharmaceutical composition is administered intravenously. Saline solutions and other physiologically compatible solutions also can be employed as liquid carriers, particularly for injectable solutions. Compositions can contain along with an active ingredient: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidone, celluloses and derivatives thereof, povidone, crospovidones and other such binders known to those of skill in the art. Suitable pharmaceutical excipients include but are not limited to starch, glucose, mannitol, lactose, sucrose, gelatin, malt, rice, flour, chalk, silica gel, sodium stearate, glycerol monostearate, talc, sodium chloride, dried skim milk, glycerol, propylene, glycol, citrates and sulfates, water, and ethanol. A composition, if desired, also can contain minor amounts of wetting or emulsifying agents, or pH buffering agents, for example, acetate, sodium citrate, ammonium hydroxide, cyclodextrin derivatives, sorbitan monolaurate, triethanolamine sodium acetate, triethanolamine oleate, and other such agents. These compositions can take the form of solutions, suspensions, emulsion, tablets, pills, capsules, powders, and sustained release formulations Examples of suitable pharmaceutical carriers are described in "Remington's Pharmaceutical Sciences" by E. W. Martin. Such compositions will contain a therapeutically effective amount of P-188, in a form described herein, including the LCMF form, together with a suitable amount of carrier so as to provide the form for proper administration to a subject or patient.

The formulation is selected to suit the mode of administration. For example, compositions containing P-188, or LCMF P-188, can be formulated for parenteral administration by injection (e.g., by bolus injection, short term infusion or continuous infusion). The injectable compositions can take such forms as suspensions, solutions or emulsions in oily or aqueous vehicles. The sterile injectable preparation also can be a sterile injectable solution or suspension in a non-toxic parenterally-acceptable diluent. Buffers, preservatives, antioxidants, isotonicity agents and other suitable ingredients, can be incorporated as required, or, alternatively, can comprise the formulation.

Formulations suitable for parenteral administration include aqueous and non-aqueous sterile injection solutions, which can contain anti-oxidants, buffers, bacteriostats and solutes that render the formulation compatible with the intended route of administration. The formulations can be presented in unit-dose or multi-dose containers, for example, sealed ampules and vials, prefilled syringes or other delivery devices and can be stored in an aqueous solution, dried or freeze-dried (lyophilized) condition, requiring only the addition of the sterile liquid carrier, for example, water for injection, immediately prior to use.

The poloxamer, particularly the purified LCM-containing P-188, or the LCMF P-188, can be formulated as the sole pharmaceutically active ingredient in the composition or can be combined with other active ingredients. Liposomal suspensions, including tissue-targeted liposomes, also can be suitable as pharmaceutically acceptable carriers. These can be prepared according to methods known to those skilled in the art. The P-188, or LCMF P-188, is formulated in an amount sufficient to exert a therapeutically useful effect in the absence of undesirable side effects on the subject treated. The therapeutically effective concentration can be determined empirically by testing the compounds in known in vitro and in vivo systems, such as the assays provided herein.

2. Dosage Formulation

The pharmaceutical compositions containing P-188 or LCMF P-188 provided herein, can be formulated for single dosage (direct) administration, multiple dosage administration or for dilution or other modification. Typically, for practice of the methods provided herein, P-188 or LCMF P-188, is provided as a single infusion that is administered only once, or is administered and not repeated for at least a week. The concentrations of the compounds in the formulations are effective for delivery of an amount, upon administration, that is effective for the intended treatment, and in particular as a single short term infusion or where the short term infusion is re-administered at intervals of not less than one week according to the dosage regime provided herein. Those of skill in the art readily can formulate a composition for administration in accord with the methods herein. For example, to formulate a composition, the weight fraction of a compound or mixture thereof is dissolved, suspended, dispersed, or otherwise mixed in a selected vehicle at an effective concentration such that heart failure is improved.

The precise amount or dose of the therapeutic agent administered depends on the route of administration, and other considerations, the weight and general state of the subject and the subject and the status of the heart failure. Local administration of the therapeutic agent will typically require a smaller dosage than any mode of systemic administration, although the local concentration of the therapeutic agent can, in some cases, be higher following local administration than can be achieved with safety upon systemic administration. For the methods herein, the polyoxyethylene/polyoxypropylene copolymer generally is administered by intravenous infusion.

If necessary, a particular dosage and duration and treatment protocol can be empirically determined or extrapolated. For example, exemplary doses of P-188 or LCMF P-188 provided herein, if necessary, can be used as a starting point to determine appropriate dosages for a particular subject and condition. The duration of treatment and the interval between injections will vary with the severity of the disease or condition and the response of the subject to the treatment, and can be adjusted accordingly. Factors such as the level of activity and half-life of the P-188, or LCMF P-188, can be taken into account when making dosage determinations. Particular dosages and regimens can be empirically determined by one of skill in the art.

As described herein, the first dose of the polyoxyethylene/polyoxypropylene copolymer, such as P-188 is typically is administered at a dosage of 100-600 mg/kg, such as 400-500 mg/kg. A second dosage can be administered after at least one week, generally 2-3 weeks after the first dose. Subsequent infusions can be administered at about 3-4 week intervals or even longer intervals as heart performance improves.

The poloxamer can be formulated for infusion at a concentration ranging from about 10.0 mg/mL to about 300.0 mg/mL or 10.0 to 200.0 mg/ml, such as at or at least 10.0, 15.0, 20.0, 25.0, 30.0, 35.0, 40.0, 45.0, 50.0, 55.0, 60.0, 65.0, 70.0, 75.0, 80.0, 85.0, 90.0, 95.0, 100.0, 105.0, 110.0, 115.0, 120.0, 125.0, 130.0, 135.0, 140.0, 145.0, 150.0, 155.0, 160.0, 165.0, 170.0, 175.0, 180.0, 185.0, 190.0, 195.0 or 200.0 mg/mL, for direct administration. Typically, the concentration is not more than 25%, i.e. 250 mg/mL. The concentration can be selected based upon the total dose and rate of infusion and the volume limitations of the patient. Generally a dose of 100-600 mg/kg is administered over 1-12 hours such as 1-6 hours.

For example, the poloxamer is administered at a concentration of between about 0.5% to 25% although more dilute or higher concentrations can be used. For heart failure, higher concentrations are generally used in order to provide a short infusion of the relatively high dose (100 mg/kg to 675 mg/kg). For example, the poloxamer can be administered in an amount between about 0.5% to about 25% by weight/volume, such as at least or at 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10.0%, 10.5%, 11%, 11.5%, 12%, 12.5%, 13%, 13.5%, 14%, 14.5%, 15%, 15.5%, 16%, 16.5%, 17%, 17.5%, 18%, 18.5%, 19%, 19.5%, 20%, 20.5%, 21%, 21.5%, 22%, 22.5%, 23%, 23.5%, 24%, 24.5% or 25% by weight/volume. For example, the concentration is 10% to 25%, such as at or about 22.5%, or 10% to 20% or 15% to 20% or 15%-30% or 15% to 28%, or 20-23%, or 15% to 25%, or 20-25%. In one example, the poloxamer can be formulated as a sterile, non-pyrogenic solution intended for administration with or without dilution. The final dosage form can be a prepared in a 100 mL vial where the 100 mL contains 15 g (150 mg/mL) of purified poloxamer 188, such as LCMF P-188, 308 mg sodium chloride USP, 238 mg sodium citrate USP, 36.6 mg citric acid USP and water for injection USP Qs to 100 mL. The pH of the solution is approximately 6.0 and has an osmolarity of about 312 mOsm/L.

3. Administration and Dosage Regime

In the methods herein, poloxamer 188, such as a purified poloxamer 188 or LCMF P-188 described herein, can be administered to a subject for treating heart failure, and in particular any disease or condition associated with heart failure as described in Section F. In particular, poloxamer 188, such as a purified poloxamer 188 described herein, is intended for use either as a stand alone agent or in combination with other therapeutic methods including mechanical devices or pharmacological medications, which can lower blood pressure or otherwise treat heart failure and/or heart dysfunction.

Treatment of diseases and conditions, such as any described in Section F, with poloxamer 188, or a purified poloxamer 188 described herein, can be effected by any suitable route of administration using suitable formulations as described herein including, but not limited to, injection, pulmonary, oral and transdermal administration. Treatment typically is effected by intravenous administration.

Active agents, for example a poloxamer 188, such as LCMF P-188, are included in an amount sufficient that exert a therapeutically useful effect in the absence of undesirable side effects on the patient treated. The amount of a P-188, such as LCMF P-188, to be administered for the treatment heart failure, for example for treating a patient with acute decompensation, can be determined by standard clinical techniques. In addition, in vitro assays and animal models can be employed to help identify optimal dosage ranges. The precise dosage, which can be determined empirically, can depend on the particular composition, the route of administration, the type of disease to be treated and the seriousness of the disease. The dosage is as described above, typically 100-500 mg/kg and adjusted as needed, and administered at intervals longer than a week as described above.

For example, practical limitations have restricted the clinical use of poloxamer 188 that was manufactured only according to National Formulary specification (P-188-NF) and not purified (Emanuele and Balasubramanian, Drugs in R&D 14(2):73-83 (2014)). Such un-purified poloxamer 188 resulted in renal dysfunction in a subset of patients enrolled in early clinical trials. In addition, animal studies reveal that P-188-NF increases the levels of serum creatinine and creatinine is not efficiently cleared from the kidneys at the end of the drug infusion. The purified poloxamer 188 described herein has been modified to address the limitations of P-188-NF. To prevent elevation of creatinine levels and renal toxicity, poloxamer 188 was purified to remove low and high molecular weight species contaminants. In clinical studies, for example the C97-1248 study, where creatinine levels were evaluated in human patients treated with a purified form of poloxamer 188 (P-188-P), which lacks a lower molecular weight species of poloxamer 188, researchers found that intravenous administration of P-188-P failed to induce a significant increase in serum creatinine above the levels of a placebo. The loss of low and high molecular weight species, based on assessment by high performance liquid chromatography, reduces or eliminates renal risk associated with unpurified (P-188-NF) treatments. Therefore, a purified poloxamer 188, such as a poloxamer 188 described herein, does not exhibit the practical limitations present in the previously assessed, unpurified form.

The dosing regimen of poloxamer 188, such as a purified poloxamer 188 described herein, has been modified to address the limitations of clinical use of previous poloxamer 188. Any poloxamer 188 described herein is administered in a single dose or multiple doses at intervals as described herein to produce a long lasting effect on cardiac function without the toxicity associated with a previously analyzed poloxamer 188.

In some examples, methods of treatment with poloxamer 188 requires a longer duration of action in order to effect a sustained therapeutic effect. This is particularly true in treatment of chronic heart failure. As discussed elsewhere herein, the half-life of poloxamer 188 is between 6-8 hours in humans. Despite a relatively short half-life, it is shown herein that the effects of poloxamer 188, such as a purified poloxamer 188, for treatment of heart failure are long lasting. Thus, the poloxamer 188 described herein can be used to deliver longer lasting therapies for cardiac disorders.

If necessary, a particular dosage and duration and treatment protocol can be empirically determined or extrapolated. Dosages for poloxamer 188 previously administered to human subjects and used in clinical trials can be used as guidance for determining dosages for poloxamer 188, such as a purified poloxamer 188 described herein. Dosages for poloxamer 188 can also be determined or extrapolated from relevant animal studies. Factors such as the level of activity and half-life of poloxamer 188 can be used in making such determinations. Particular dosages and regimens can be empirically determined based on a variety of factors. Such factors include body weight of the individual, general health, age, the activity of the specific compound employed, sex, diet, time of administration, rate of excretion, drug combination, the severity and course of the disease, and the patient's disposition to the disease and the judgment of the treating physician. The active ingredient, poloxamer 188, typically is combined with a pharmaceutically effective carrier. The amount of active ingredient that can be combined with the carrier materials to produce a single dosage form or multi-dosage form can vary depending upon the host treated and the particular mode of administration.

In particular examples, the poloxamer, such as P-188 (e.g., LCMFP-188) is formulated for administration to a patient at a dosage of about 100 to 600 mg/kg patient body weight, such as 100 to 500 mg/kg patient body weight, for example 100 mg/kg to 450 mg/kg, 100 to 400 mg/kg, 100 mg/kg to 300 mg/kg, 100 mg/kg to 200 mg/kg, 200 mg/kg to 500 mg/kg, 200 mg/kg to 450 mg/kg, 200 mg/kg to 400 mg/kg, 200 mg/kg to 300 mg/kg, 300 mg/kg to 500 mg/kg, 300 mg/kg to 450 mg/kg 300 mg/kg to 400 mg/kg, 400 mg/kg to 500 mg/kg, 400 mg/kg to 450 mg/kg or 450 mg/kg to 500 mg/kg patient body weight, such as about 100, 125, 150, 200, 250, 300, 350, 400, 450, 500, or 600 mg/kg patient body weight. In particular examples the poloxamer is formulated for administration at a dosage of about 200-450 mg/kg, such as 400 mg/kg patient body weight.

In a patient with heart failure the goal is to administer the dose in the smallest volume possible. Typically, the volume to be administered is not greater than 4.0 mL/kg of a subject. For example, the volume in which the dose is administered to a subject can be 0.4 mL/kg to 4.0 mg/kg, 0.4 mL/kg to 3.5 mL/kg, 0.4-3.0 ml/kg, 0.4-2.5 ml/kg, 0.4 mL/kg to 2.0 mL/kg, 0.4 mL/kg to 1.8 mL/kg. 0.4 mL/kg to 1.4 mL/kg, 0.4 mL/kg to 1.0 mL/kg, 0.4 mL/kg to 0.6 mL/kg, 0.6 mL/kg to 4.0 mL/kg, 0.6 mL/kg to 3.0 mL/kg, 0.6 mL/kg to 2.0 mL/kg, 0.6 mL/kg to 1.8 mL/kg, 0.6 mL/kg to 1.4 mL/kg, 0.6 mL/kg to 1.0 mL/kg, 1 mL/kg to 4 mL/kg, 1.0 ml/kg-3.0 ml/kg, 1 mL/kg to 2.5 mL/kg, 1 mL/kg to 2.0 mL/kg, 1 mL/kg to 1.8 mL/kg, 1 mL/kg to 1.4 mL/kg, 1.4 mL/kg to 4.0 mL/kg, 1.4 ml/kg-3.0 ml/kg, 1.4 mL/kg to 2.5 mL/kg, 1.4 mL/kg to 2.0 mL/kg, 1.4 mL/kg to 1.8 mL/kg, 1.8 ml/kg-4.0 ml/kg, 1.8 mL/kg to 3.0 mL/kg, 1.8 mL/kg to 2.5 mL/kg, 1.8 mL/kg to 2.0 mL/kg, 2.0 ml/kg-4.0 ml/kg, 2.0 mL/kg to 3.0 mL/kg, 2.0 mL/kg to 2.5 mL/kg or 2.5 mL/kg to 3.0 mL/kg. For example, a composition with a concentration of 22.5% (i.e. 225 mg/mL) that is administered to a 100 kg subject at a dose of 100 mg/kg would require a volume of about 44 ml or about 0.4 mL/kg to achieve that dose.

The administered dose is typically administered as an infusion. Generally the infusion is an intravenous infusion. The infusion, to provide the appropriate dosage, can be provided to the subject over a time period that is 1 hour to 24 hours, 1 hour to 12 hours, 1 hour to 6 hours, 1 hour to 3 hours, 1 hour to 2 hours, 2 hours to 24 hours, 2 hours to 12 hours, 2 hours to 6 hours, 2 hours to 3 hours, 3 hours to 24 hours, 3 hours to 12 hours, 3 hours to 6 hours, 6 hours to 24 hours, 6 hours to 12 hours, or 12 hours to 24 hours, such as generally over at time period that is up to or is about 1 hour, 2 hours, 3 hours, 4 hours, 5 hours, 6 hours, 7 hours, 8 hours, 9 hours, 10 hours, 12 hours, 15 hours, 18 hours, 20 hours, 22 hours or more. It is within the level of a treating physician to determine the appropriate time and rate of infusion to deliver an effective dose that can be tolerated by a subject.

The infusion of poloxamer, such as P-188 (e.g., LCMF P-188), is provided as a single infusion that is not repeated for at least a week, and then can be subsequently repeated at intervals of at least a week, generally up to 2-4 weeks, and, as improvement is observed, increasingly longer intervals, and/or lower dosages. As discussed elsewhere herein, it is found that the effects of P-188 following a single short term administration on parameters of heart function lasts for more than a week, two weeks and up to 3 weeks. Thus, it is possible to provide P-188 treatment with dosage administrations no more than once weekly, and subsequently less frequently. In examples herein, the dosage can be repeated once every week, once every 2 weeks, once every three weeks, once every 4 weeks, once every 5 weeks or once every 6 weeks. For example, the dose can be repeated between 1 week to 4 weeks after the previous dose, such that the dose is repeated at 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days 26 days, 27 days, 28 days, 29 days, 30, 31 days, 32 days, 33 days, 34 days, 35 days, 36 days, 37 days, 38 days, 39 days, 40 days, 41 days, or 42 days following completion of the prior dose. The dose that is administered in the repeated dosing can be the same or different than the prior dose. For example, it can be increased or decreased from the prior dose. It is within the level of the treating physician to determine the appropriate frequency of administration and level or amount of dosages in repeated dosings.

The length of time of the cycle of administration can be empirically determined, and is dependent on the disease to be treated, the severity of the disease, the particular patient, and other considerations within the level of skill of the treating physician. The length of time of treatment with P-188, or LCMF P-188, can be one day, one week, two weeks, one months, several months, one year, several years or more. Over that time P-188 or LCMF P-188 can be administered no more than once weekly, such every 7 days, 8 days, 9 days, 10 days, 11 days, 12 days, 13 days, 14 days, 15 days, 16 days, 17 days, 18 days, 19 days 20 days, 21 days, 22 days, 23 days, 24 days, 25 days, 26 days, 27 days or 28 days or more as described above. If disease symptoms persist in the absence of discontinued treatment, treatment can be continued for an additional length of time. Over the course of treatment, evidence of disease and/or treatment-related toxicity or side effects can be monitored.

In addition, the cycle of administration can be tailored to add periods of discontinued treatment in order to provide a rest period from exposure to the treatment. The length of time for the discontinuation of treatment can be for a predetermined time or can be empirically determined depending on how the patient is responding or depending on observed side effects. For example, the treatment can be discontinued for one week, two weeks, one month or several months.

For treatments involving acute heart failure, dosings will typically start when the patient is admitted to the hospital, but it can be started any time during hospitalization to meet the subjects needs. More generally, the dosing will start during the first 72 hours of hospitalization. For chronic heart failure, dosing generally is provided based on the needs of the subject, since such subjects generally do not undergo hospitalization.

The formulations used in the methods provided herein can be administered by any appropriate route, for example, orally, nasally, pulmonary, parenterally, intravenously, intradermally, subcutaneously, intraarticularly, intracisternally, intraocularly, intraventricularly, intrathecally, intramuscularly, intraperitoneally, intratracheally or topically, as well as by any combination of any two or more thereof, in liquid, semi-liquid or solid form and are formulated in a manner suitable for each route of administration. Multiple administrations, such as repeat administrations described herein, can be effected via any route or combination of routes. The most suitable route for administration will vary depending upon the disease state to be treated. Typically, the compositions are formulated for intravenous infusions.

The effective amounts of a poloxamer, such as P-188 and in particular an LCMF P-188 as provided herein, can be delivered alone or in combination with other agents for treating a disease or condition. It is within the level of a skilled artisan to choose a further additional treatment to administer in conjunction with a therapeutic regime employing LCMF P-188. Such a decision will depend on the particular disease or condition being treated, the particular subject being treated, the age of the subject, the severity of the disease or condition and other factors.

E. Methods of assessing heart function and activity of Poloxamer treatment or monitoring therapies 1. Assays of Heart Function It is within the level of a skilled physician to assess heart failure. Assays for heart failure using clinical assessment including assays for breathlessness, orthopnoea (shortness of breath experienced when lying flat), paroxysmal nocturnal dyspnoea (severe shortness of breath that occurs most often at night), exercise tolerance including time to fatigue, edema, including ankle and abdomen swelling, and cyanosis. Assays to evaluate heart failure can also be used to diagnose cough, wheezing, weight, to assess for weight loss or gain and/or change in appetite, personality changes, palpitations and fainting. A number of such assays known to those of skill in the art are subject to quantitative analysis (e.g., palpitations, cyanosis, etc.).

Systolic heart failure or diastolic heart failure share the same clinical phenotype, but differ with respect to the morphological and functional changes that occur in the heart. Assays to differentiate between systolic and diastolic dysfunction can be used to assess ejection volume by one of skill in the art, such as a skilled physician. Systolic heart failure presents with a decrease in ejection volume, while diastolic heart failure retains an intact ejection volume; moreover, systolic and diastolic heart failure are most effectively distinguished from each other using internal measurements of heart volume, such as, for example, M-Mode, two-dimensional or three-dimensional echocardiography, cardiac magnetic resonance imaging (CMRI), doppler, or pulsed reflected ultrasound. In the methods used herein, assays for hemodynamic and ventriculographic measurements, including those used to assess aortic and left-ventricular (LV) pressures, peak rate of change of LV pressure during isovolumic contraction and relaxation, LV end-diastolic pressure, cardiac output (CO), LV stroke volume (SV), systemic vascular resistance (SVR), LV end-systolic (ESV) and end-diastolic (EDV) volumes, and LV ejection fraction (EF) (Sabbah et al. (1991) Am. J. Physiol. 260 (Heart Circ. Physiol. 20): H1379-H1384; Zaca et al. (2007) J. Am. Coll. Cardiol., 50:551-557; Dodge, H. T., et al. The American Journal of Cardiology 18:10-24 (1966)) can be used and are known to those of skill in the art.

Other assays for heart failure include those that assess hemodynamic performance, left ventricular-end diastolic volume, left ventricular-end systolic volume, and ejection fraction. For example, assays such as pulsed-wave Doppler echocardiography can be used to measure mitral inflow velocity.

In another method, in vivo measurement of cardiac function can be measured using cardiac ventriculography. In the assay, ventriculograms are performed using power injection of liquid contrast material, and movement of the contrast liquid into the heart is recorded on digital media. Image correction can be performed using radiopaque markers placed on the distal end of the LV ventriculographic catheter and LV end-systolic and LV end-diastolic volumes can be calculated.

The ability of a poloxamer 188, such as a purified poloxamer 188, to exhibit therapeutic activity for reducing or preventing systolic heart dysfunction can be assessed using any one or more of the assays described above. For example, the ability of a poloxamer 188, such as a purified poloxamer 188, to reduce end systolic volume can be assessed using any one or more of the assays above in vivo. In one example, a purified poloxamer 188 can be administered to a subject with heart failure, or an appropriate animal model, and the effect on end-systolic volume can be assessed using cardiac ultrasound and compared to subjects or animal models not administered a purified poloxamer 188.

In another example, the ability of a poloxamer 188, such as a purified poloxamer 188, to exhibit therapeutic activity for reducing or preventing diastolic heart dysfunction can be assessed using any one or more of the assays described above. For example, the ability of a poloxamer 188, such as a purified poloxamer 188, to increase Ei/Ai and DCT can be assessed using any one or more of the assays above in vivo. In one example, a purified poloxamer 188 can be administered to a subject with diastolic heart failure, or an appropriate animal model, and the effect Ei/Ai and DCT can be assessed and compared to subjects or animal models not administered a purified poloxamer 188.

In an additional example, the ability of a poloxamer 188, such as a purified poloxamer 188, to exhibit therapeutic activity for reducing or preventing heart dysfunction can be assessed using any one or more of the assays described above. For example, the ability of a poloxamer 188, such as a purified poloxamer 188, to modify LV fractional area of shortening (FAS), a measure of LV systolic function, can be assessed using any one or more of the assays above in vivo. In one example, a purified poloxamer 188 can be administered to a subject with heart failure, or an appropriate animal model, and the effect on FAS can be assessed using echocardiographic and/or Doppler studies and compared to subjects or animal models not administered a purified poloxamer 188.

The ability of a poloxamer 188, such as a purified poloxamer 188, to affect any one or more of the structural or physiological properties associated with heart failure described above, or any other associated phenotypes, can be assessed using any one or more of the assays described above. The methods can be used to assess heart function in any subject with heart failure, including heart failure induced by diastolic or systolic dysfunction.

2. Biomarkers

Biomarkers in blood serum and the effects of administration of a poloxamer 188, such as a purified poloxamer 188, can be measured using various ex vivo techniques that are well known in the art.

In one example, biomarkers can be utilized for diagnostic purposes to assess cardiac risk and acute cardiac damage or failure, and vary depending on the disease with which they are associated. By determining the presence, absence, increase or decrease of such a biomarker in, for example, the blood or serum of an individual or animal model, it is also possible to determine whether cardiac failure is progressing or is being suppressed. Exemplary biomarkers for heart failure include, but are not limited to: N-terminal pro-brain natriuretic peptide (nt-pro BNP), troponin-I (Tn-I), matrix metalloproteinase-2 (MMP-2), Interleukin 6 (IL6), C-reactive protein (CRP) and Tumor necrosis factor-alpha (TNFα).

In one method, one of skill in the art can identify and determine the level of expression of one or more of these biomarkers, or functional variants thereof, in the patient, where an alteration, including an increase or a decrease, in expression indicates that the patient can have a more severe form of heart failure. For example, a patient with increased Tn-I expression indicates that the patient has experienced cardiomyocyte injury and death, and thus, can have a more severe form of heart failure.

Additional biomarkers that can be used to assay for heart failure include: measures of oxidative stress, including isoprostane and derivatives of reactive oxygen metabolites (D-ROMs), urinary excretion of 8-iso-prostaglandin F2 alpha (IPGF2), which is a chemically stable and quantitative measure of oxidative stress, and is known to correlate with the severity of systolic heart failure, Bilirubin, a scavenger of ROS. 8-OHdG, a marker of systemic DNA damage whose level correlates with the severity of ischemic systolic heart failure, as assayed by the number of diseased vessels visualized using coronary angiography.

The ability of a poloxamer 188, such as a purified poloxamer 188, to affect any one or more of the markers associated with heart failure described above, or any other associated markers or phenotypes, can be assessed using any one or more of the assays described above. The methods can be used to assess heart function in any subject with heart failure, including heart failure induced by diastolic or systolic dysfunction.

a. Matrix Metalloproteinase-2 (MMP-2)

Inflammatory signals, such as inflammation of the heart, regulate matrix metalloproteinase activity. Activated metalloproteinases facilitate changes in the extracellular matrix and, ultimately, tissue remodeling in conditions of inflammation and injury and are highly expressed in unstable plaques. Exemplary matrix metalloproteinases are MMP-9, MMP-1, MMP-3, and MMP-2. MMP-2 (Shirakabe, A. et al. Int. Heart J. 51(6): 404-10 (2010)). Exemplary assays for heart failure include determining the expression level of the MMP-2 gene, where increased MMP-2 expression indicates that the patient can have heart disease or actively progressing heart failure.

The ability of a poloxamer 188, such as a purified poloxamer 188, to exhibit therapeutic activity for reducing or preventing heart dysfunction can be assessed using any one or more of the biomarkers described above. For example, the ability of a poloxamer 188, such as a purified poloxamer 188, to ameliorate heart failure can be assessed using any one or more of the assays above in vivo. In one example, a purified poloxamer 188 can be administered to a subject with heart failure, or an appropriate animal model, and the effect on MMP-2 expression can be assessed using a biochemical assay, such as an assay known to those of skill in the art, and MMP-2 levels in, for example, the blood or serum can be compared to subjects or animal models not administered a purified poloxamer 188. For example, administration of a poloxamer 188, such as a purified poloxamer 188, can result in a decrease in MMP-2 levels in blood of a model animal subjected to heart failure.

b. Interleukin 6 (IL-6)

Interleukin-6 (IL-6) is a pro-inflammatory member of the family of cytokine proteins which increase their expression in response to tissue injury or inflammation, for example cardiac injury or inflammation. Blood serum measurement of IL-6 expression, using, for example, the enzyme-linked immunosorbent assay (ELISA) can be used to measure IL-6 levels. IL-6 levels increase in heart failure patients and IL-6 expression promotes production of C-reactive protein.

The ability of a poloxamer 188, such as a purified poloxamer 188, to exhibit therapeutic activity for reducing or preventing heart dysfunction can be assessed using any one or more of the biomarkers described above. For example, the ability of a poloxamer 188, such as a purified poloxamer 188, to ameliorate heart failure can be assessed using any one or more of the assays above in vivo. In one example, a purified poloxamer 188 can be administered to a subject with heart failure, or an appropriate animal model, and the effect on IL-6 expression can be assessed using a biochemical assay, such as an assay known to those of skill in the art, and IL-6 levels in, for example, the blood or serum can be compared to subjects or animal models not administered a purified poloxamer 188. For example, administration of a poloxamer 188, such as a purified poloxamer 188, can result in a decrease in IL-6 levels in blood of a model animal subjected to heart failure.

c. C-reactive protein (CRP)

C-reactive protein (CRP) is a marker for inflammation, whose expression is triggered by an increase in IL-6 production. Increase in serum CRP is a risk factor for heart failure and myocardial infarction (Kiechl, et al. Circulation, 103, 1064-1070. (2001)) and a positive prognosis in heart failure patients inversely correlates with CRP levels (Lourneço et al. (2010) Clin Cardiol. 33(11):708-14). Blood serum measurement of CRP levels, can be assayed, for example, using biochemical methods such as ELISA or western blotting.

The ability of a poloxamer 188, such as a purified poloxamer 188, to exhibit therapeutic activity for reducing or preventing heart dysfunction can be assessed using any one or more of the assays above in vivo. In one example, a purified poloxamer 188 can be administered to a subject with heart failure, or an appropriate animal model, and the effect on CRP expression can be assessed using a biochemical assay, such as an assay known to those of skill in the art, and CRP levels in, for example, the blood or serum can be compared to subjects or animal models not administered a purified poloxamer 188. For example, administration of a poloxamer 188, such as a purified poloxamer 188, can result in a decrease in CRP levels in blood of a model animal subjected to heart failure.

d. Tumor Necrosis Factor-Alpha (TNFα)

TNFα is a proinflammatory cytokine involved in the regulation of immune function. TNFα expression is used as a marker for inflammation, including cardiac inflammation; moreover, TNFα is not expressed at detectable levels in normal heart tissue, but increases dramatically in heart failure patients and its expression correlates with the severity of the disease (Feldman et al. J Am Coll Cardiol. 35(3):537-544 (2000)). Therefore, TNFα serves as an effective biomarker for heart failure and a decrease in TNFα expression can indicate an improvement in heart failure progression and symptoms.

In one example, the ability of a poloxamer 188, such as a purified poloxamer 188, to exhibit therapeutic activity for reducing or preventing heart dysfunction can be assessed using TNFα expression as a biomarker for heart failure. In one example, a purified poloxamer 188 can be administered to a subject with heart failure, or an appropriate animal model, and the effect on TNFα expression can be assessed using a biochemical assay, such as an assay known to those of skill in the art, and TNFα levels in, for example, the blood or serum can be compared to subjects or animal models not administered a purified poloxamer 188. A decrease in TNFα levels after administration of poloxamer 188, such as a purified poloxamer 188, can indicate an improvement in heart failure symptoms and a decrease in heart failure progression.

e. N-Terminal Pro-Brain Natriuretic (Nt-Pro BNP)

N-terminal pro-brain natriuretic (nt-pro BNP) is a hormone whose expression increases in response to increased stress on the ventricular wall of the heart. nt-pro BNP is secreted into the bloodstream, which serves an effective collection route for samples used for biochemical assessment of protein expression, including assays described above. Because nt-pro BNP levels and the severity of heart failure are positively correlated, nt-pro BNP levels are potentially useful as a biomarker for heart failure and in the evaluation of treatment efficacy.

For example, the ability of a poloxamer 188, such as a purified poloxamer 188, to exhibit therapeutic activity for reducing or preventing heart dysfunction can be assessed using nt-pro BNP expression as a biomarker for heart failure or heart failure severity. In one example, a purified poloxamer 188 can be administered to a subject with heart failure, or an appropriate animal model, and the effect on nt-pro BNP expression can be assessed using a biochemical assay, such as an assay known to those of skill in the art, and nt-pro BNP levels in, for example, the blood or serum can be compared to subjects or animal models not administered a purified poloxamer 188. A decrease in nt-pro BNP levels after administration of poloxamer 188, such as a purified poloxamer 188, can indicate an improvement in heart failure symptoms and a decrease in heart failure symptoms or disease progression.

3. In Vivo Animal Models

The activities and properties of poloxamer 188 can be assessed in vivo. Assays for such assessment are known to those of skill in the art and are known to correlate tested activities and results to therapeutic activities. Non-human animal models can be used to assess activity, efficacy and safety of poloxamer 188. For example, non-human animals can be used as models for a disease or condition. Animal models can include, but are not limited to, mice, rats, rabbits, dogs, guinea pigs and non-human primate models, such as cynomolgus monkeys or rhesus macaques. Animal models include genetic models as well as induced heart failure models, including acute, chronic, ischemic, stress-induced and other types of heart disease or heart failure that can be induced in non-human animals, such as by multiple sequential intracoronary embolizations with microspheres, prior to administration of a poloxamer 188, such as a purified poloxamer 188, to monitor the effects on acute or chronic heart failure.

Animal models also can be used to monitor stability, half-life, and clearance of poloxamer 188. Such assays are useful for comparing different forms of poloxamer 188 and for calculating doses and dose regimens for further non-human animal and human trials. For example, poloxamer 188, such as any poloxamer 188 described herein, can be infused into an animal's bloodstream through intravenous administration. Blood samples are then taken at time-points after injection (such as minutes, hours and days afterwards) and then the level of the poloxamer 188 in bodily samples including, but not limited to, serum or plasma can be monitored at specific time-points for example by ELISA or radioimmunoassay. These types of studies can provide information regarding half-life, clearance and stability of the poloxamer 188, which can assist in determining suitable dosages for administration in acute, chronic or other types of heart failure.

Genetic models also are useful. Animals, such as mice, can be generated which mimic a disease or condition by the overexpression, underexpression or knock-out of one or more genes, such as, for example, dystrophin deficient MDX mice (also known as Dmd$^{mdx}$ mice) that display muscular dystrophy phenotypes, and dobutamine challenged MDX mice. Such animals can be generated by transgenic animal production techniques well-known in the art or using naturally-occurring or induced mutant strains. MDX mice exhibit reduced left ventricular end diastolic volume (LVEDV). LVEDV can be measured upon intravenous infusion of poloxamer 188. Poloxamer 188 activity can also be assessed in MDX mice subject to the severe insult of dobutamine treatment, which serves as a model for acute stress, and which typically causes acute heart failure in the mice. Moreover, pre-treatment with poloxamer 188 can be provided to MDX mice challenged with dobutamine to induce heart failure, and heart function can be assessed using a variety of readouts.

Additional small animal models of cardiac dysfunction can be used to assess the effect of poloxamer 188, such as any poloxamer 188 described herein, on acute, chronic, ischemic or other types of heart failure. In one non-limiting example, an animal model such as a rat can be used. Permanent and temporary ligation of the left coronary artery can be performed in rats to produce an infarction of greater than 40%. The rats become stable after 1 to 3 weeks, in 3 weeks exhibit significant left ventricular dysfunction, and after 8 weeks exhibit significant loss of dystrophin, which results in heart myopathy. Poloxamer 188, such as any Poloxamer 188 described herein can be administered prior to or following artery ligation and the animals can be assessed for heart function using a variety of assays described above. Poloxamer activity can be assessed in rats with myocardial damage induced by chemical means, ie. administering the beta-one adrenergic receptor agonist isoproterenol, by electrical means, ie. generating overlapping burns to the ventricle epicardium, or surgically, ie. ligation of the left coronary artery.

Non-rodent models of heart failure also exist. Poloxamer 188, such as a purified poloxamer 188, activity can be assessed in dogs with progressive degeneration of cardiac muscle, for example dystrophin-deficient golden retrievers who exhibit muscular dystrophy (GRMD) (Kornegay et al. Mamm Genome 23(1-2):85-108 (2012)). GRMD mimics the progression of Duchenne muscular dystrophy (DMD), a progressive disorder of striated muscle in humans, also characterized by emerging heart disease. In one example, afflicted golden retrievers can be infused with a treatment composition through a vascular access port connected to an indwelling jugular catheter (Townsend et al. J. Clin Invest 120(4):1140-50 (2010)). After recovery from surgery, and an equilibrium period, for example of one week, animals are infused with a treatment composition or a placebo such as saline. Drug or placebo administration is in accord with test conditions, such a single dose or a plurality of doses at various intervals. The effect of drug administration can be assessed using known assays, such as assays described here previously, for heart function.

Dog models also can be employed. These include dogs with inherited heart disorders, and also injury and trauma models of heart failure in dogs. The dog models are used to evaluate the activity of Poloxamer 188, and its safety and efficacy as a treatment for heart failure. One example of such models is one in which dogs are subjected to the microembolization procedure to induce heart failure (Rastogi S., et al. American journal of physiology Heart and circulatory physi. 300:H1501-H1509 (2011); Sabbah H. N., et al. Am J Physiol. 260:H1379-H1384 (1991)). This model mimics several phenotypes of human heart failure, including marked and progressive depression of LV systolic and diastolic function, reduced cardiac output and increased LV filling pressure. Additional examples included heart failure induced in dogs by damage to the heart from repeated DC shocks (McDonald et al, Journal of the American College of Cardiology 19: 460-467, 1992) or by a technique that induces rapid ventricular pacing-induced heart failure (Riegger and Liebau, Clinical Science 62: 465-469, 1982). Other non-limiting examples of heart dysfunction include pressure overloading to induce ventricular hypertrophy and failure, produced by a variety of techniques including corticosteroid administration, renal artery occlusion, unilateral nephrectomy with contralateral occlusion of the renal artery, and most extensively banding of major outflow tracts such as the aorta, which have been used in a variety of species including rat, cat and dog (Smith and Nutall, Cardiovascular Research 19: 181-186, 1985).

A poloxamer 188, such as a purified poloxamer 188 and LCMF poloxamer, can be administered to the dogs prior to, during, or following cardiac injury or dysfunction to assess effects on cardiac function. For example, prior to, and following administration of a poloxamer 188, assays for cardiac function, such as, for example, systolic or diastolic heart function, can be assessed or measured using any of the assays described above. In another example, the effects of administering a poloxamer 188 on biomarkers for heart failure can be assessed.

For example, a single dose of a poloxamer 188, such as a purified poloxamer 188 described herein, can be administered to dogs exhibiting advanced heart failure (HF), as defined as a stable (for at least 2 weeks) left ventricular ejection fraction (EF) of ≤30%, produced by multiple sequential intracoronary microembolizations. Following administration of a purified poloxamer 188, dogs can be assessed for long-lasting, significant or moderate improvements to several assays of systolic and diastolic heart functions, including: systolic and diastolic AoP, mean AoP, Peak LV, LV ESV, LV EF, CO, SV, LV FAS Ei/Ai and DCT, when assessed by ultrasound, echocardiographic and/or Doppler studies. Degree of heart failure and improvements to heart function can also be assessed using assays for biomarkers of inflammation, including cardiac inflammation. An improvement in cardiac function can be indicated by a decrease in the serum levels of biomarkers for heart failure, including: N-terminal pro-brain natriuretic peptide (nt-pro BNP), troponin-I (Tn-I), matrix metalloproteinase-2 (MMP-2), Interleukin 6 (IL6), C-reactive protein (CRP) and Tumor necrosis factor-alpha (TNFα).

4. Pharmacokinetics and Tolerability

Pharmacokinetic or pharmacodynamic studies can be performed using animal models or can be performed during studies with patients to assess the pharmacokinetic properties of a poloxamer 188, such as a purified poloxamer 188. Animal models include, but are not limited to, mice, rats, rabbits, dogs, guinea pigs and non-human primate models, such as cynomolgus monkeys or rhesus macaques. In some instances, pharmacokinetic or pharmacodynamic studies are performed using healthy animals. In other examples, the studies are performed using animal models of a disease or disorder for which therapy with a poloxamer 188 is considered, such as animal models of heart failure, for example animal models of diastolic or systolic heart failure.

The pharmacokinetic properties of a poloxamer 188, such as a purified poloxamer 188, can be assessed by measuring such parameters as the maximum (peak) concentration ($C_{max}$), the peak time (i.e. when maximum concentration occurs; $T_{max}$), the minimum concentration (i.e. the minimum concentration between doses; $C_{max}$), the elimination half-life ($T_{1/2}$), and area under the curve (i.e. the area under the curve generated by plotting time versus concentration; AUC), following administration. The absolute bioavailability of the poloxamer 188 can be determined by comparing the area under the curve of poloxamer 188 following subcutaneous delivery ($AUC_{sc}$) with the AUC of poloxamer 188 following intravenous delivery ($AUC_{iv}$). Absolute bioavailability (F), can be calculated using the formula: $F=([AUC]_{sc} \times dose_{sc})/([AUC]_{iv} \times dose_{iv})$. A range of doses and different dosing frequency of dosing can be administered in the pharmacokinetic studies to assess the effect of increasing or decreasing concentrations poloxamer 188, such as a purified poloxamer 188.

Studies to assess safety and tolerability also are known in the art and can be used herein. Following administration of a poloxamer 188 provided herein, the development of any adverse reactions can be monitored. Adverse reactions can include, but are not limited to, injection site reactions, such as edema or swelling, headache, fever, fatigue, chills, flushing, dizziness, urticaria, wheezing or chest tightness, nausea, vomiting, rigors, back pain, chest pain, muscle cramps, seizures or convulsions, changes in blood pressure and anaphylactic or severe hypersensitivity responses. Typically, a range of doses and different dosing frequencies can be administered in the safety and tolerability studies to assess the effect of increasing or decreasing concentrations of poloxamer 188 in the dose.

F. Methods Of Treatment And Therapeutic Uses

Provided herein are methods of treatment and therapeutic uses for treating or ameliorating heart failure. Heart failure is a chronic, progressive condition in which heart muscle is unable to pump sufficient blood to meet the body's needs. A healthy heart pumps blood continuously through the circulatory system to deliver oxygen- and nutrient-rich blood to the body's cells and enable normal functioning. A variety of diseases and conditions, however, can weaken the heart and reduce its ability to deliver an adequate blood supply.

The methods and uses provided herein are for treating subjects that typically exhibit symptom(s) associated with heart failure. Generally, prior to treatment, patients are selected that exhibit one or more signs or symptoms associated with heart failure. It is within the level of a skilled physician to diagnose heart failure. Subjects that have heart failure, most typically exhibit breathlessness, orthopnoea (shortness of breath experienced when lying flat), paroxysmal nocturnal dyspnoea (severe shortness of breath that occurs most often at night), reduced exercise tolerance, fatigue and tiredness, chest pain, palpitations, edema, including ankle and abdomen swelling, and cyanosis. Heart failure can also be associated with one or more other symptoms such as nocturnal cough, wheezing, weight gain, weight loss, bloated feelings, loss of appetite, confusion, depression, palpitations and fainting. A number of such symptoms are subject to quantitative analysis (e.g., palpitations, cyanosis, etc.). Other symptoms include diastolic dysfunction, decreased hemodynamic performance and decreased left ventricular-end diastolic volume.

Heart failure is typically classified as either systolic heart failure or diastolic heart failure. Both presentations are common in hypertensive patients, and both are associated with high mortality and morbidity rates. Although diastolic and systolic heart failure share the same clinical phenotype, they differ with respect to the morphological and functional changes that occur in the heart, and represent distinct diseases (Borlaug et al. Circulation 123:2006-2013 (2011)). Systolic heart failure presents with a decrease in ejection volume, while diastolic heart failure retains an intact ejection volume; moreover, systolic and diastolic heart failure are most effectively distinguished from each other using internal measurements of heart volume. In the methods and uses provided herein, poloxamer 188, such as a purified poloxamer 188, can be used to increase ejection fraction, LV end-systolic volume, and/or stroke volume in subjects with decreased ejection fraction, LV end-systolic volume, and/or stroke volume associated with systolic heart failure.

In the methods and uses provided herein, a poloxamer 188, such as a purified poloxamer 188, can be used to treat systolic heart failure of diastolic heart failure. In particular, as discussed elsewhere herein, poloxamer 188 is found to have a particular effect on treatment of systolic heart failure. Thus, in methods provided herein, poloxamer 188, such as purified Poloxamer 188, is used to treat diseases and conditions associated with systolic heart failure.

Heart failure can be caused by any conditions that reduces the efficiency of the heart to pump blood. In particular, exemplary diseases and conditions associated with heart failure, include, but are not limited to, ischemic heart disease (IHD; also called coronary heart disease), myocardial infarction, cardiomyopathy, high blood pressure, hypertensive heart disease, diseases of the heart valves, diseases of the pericardium, arrhythmias (irregular heartbeats), endocarditis, myocarditis, cerebrovascular disease, peripheral arterial disease, congenital heart disease, and rheumatic heart disease. The diseases or conditions for treatment can include acute or chronic conditions.

1. Exemplary Diseases or Conditions Associated with Heart Failure a. IschemicH Heart Disease (Coronary Artery Disease)

Provided herein is a method of reducing, lessening, ameliorating or treating heart failure caused by Ischemic heart disease by administering a poloxamer 188, such as a purified poloxamer 188, to a subject. Ischemic heart disease, also termed coronary heart disease, is the most common form of heart disease and accounts for 80% of cases, often precluding systolic dysfunction and other clinical symptoms. Generally, ischemic heart disease is attributable to the buildup of plaque, a heterogeneous material made up of macrophages, lipids, such as cholesterol and fatty acids, calcium and other products, which accumulate on the inner walls of arteries, which results in reduced blood flow and increased blood pressure. Approximately two-thirds of cases of systolic heart failure can be attributed to Ischemic heart disease. In particular, provided herein are methods of using poloxamer 188, such as a purified poloxamer 188, for treating, ameliorating or reducing ischemic heart disease. Subjects or patients with ischemic heart disease can be administered a poloxamer 188, such as a purified poloxamer 188.

The methods and uses provided herein are for treating subjects that typically exhibit symptom(s) associated with ischemic heart disease. In particular, the methods herein can be used to treat patients with chronic or acute ischemic heart disease. Generally, prior to treatment, patients are selected that exhibit one or more signs or symptoms associated with ischemic heart disease. It is within the level of a skilled physician to diagnose ischemic heart disease. Subjects that have ischemic heart disease, including chronic or acute ischemic heart disease, generally exhibit decreased blood supply characteristics which slows ventricular relaxation and can impair ventricular dilation, resulting in diastolic dysfunction. Ischemic heart disease also can be associated with one or more other symptoms such as chest pain (angina), shortness of breath, increased pro-inflammatory cytokines, and in cases of an acute 'heart attack' severe chest pressure and pain in the shoulder or arm. Selection of a subject having ischemic heart failure for treatment with a poloxamer 188, such as a purified poloxamer 188, in the methods provided herein can be based on clinical symptoms, hemodynamic and ventriculographic measurements, or levels of proinflammatory biomarkers for ischemic heart failure, for example in the blood.

In particular, provided herein are methods of using a poloxamer 188, such as a purified poloxamer 188, for treating, ameliorating or reducing ischemic heart failure induced by the reduced blood supply to the heart. Subjects or patients with ischemic heart disease can be administered a poloxamer 188, such as a purified poloxamer 188, including an LCMF poloxamer 188. The poloxamer can be administered in accord with regimens provided herein.

b. Myocardial infarction

Provided herein is a method of treating or ameliorating heart failure caused by myocardial infarction by administering a poloxamer 188, such as a purified poloxamer 188, to a subject. Myocardial infarction, also termed heart attack, is the acute, secondary effect of prolonged ischemia, or lack of blood flow, to the heart, and presents as an irreversible necrosis, or cell death, of heart tissue. Provided herein are methods of using a poloxamer 188, such as a purified poloxamer 188, for treating, ameliorating or reducing myocardial infarction induced by continued or acute ischemia of the heart. Subjects with myocardial infarction can be administered a poloxamer 188, such as a purified poloxamer 188, including an LCMF poloxamer 188. The poloxamer can be administered in accord with the regimens provided herein.

The methods and uses provided herein are for treating subjects that typically exhibit symptom(s) associated with myocardial infarction. Generally, prior to treatment, patients are selected that exhibit one or more signs or symptoms associated with myocardial infarction. It is within the level of a skilled physician to myocardial infarction. Subjects that have myocardial infarction generally exhibit an episode of angina, or chest pain, and can experience jaw pain, toothache, shortness of breath, nausea, vomiting, sweating, heartburn and/or indigestion, arm pain, upper back pain, and general malaise. Myocardial infarction commonly precipitates acute decompensated heart failure and also can be present in patients experiencing chronic heart failure. Selection of a subject having myocardial infarction for treatment with a poloxamer 188, such as a purified poloxamer 188, in the methods provided herein, can be based on the clinical symptoms listed above, the results of an electro-cardiogram or coronary angiography, based on levels of proinflammatory proteins or biomarkers for myocardial infarction, for example, in the blood. In particular, provided herein are methods of using a poloxamer 188, such as a purified poloxamer 188, for treating myocardial infarction induced by the prolonged reduction of blood supply to the heart. Subjects or patients with myocardial infarction can be administered a poloxamer 188, such as a purified poloxamer 188, including an LCMF poloxamer 188. The poloxamer can be administered in accord with the regimens provided herein c. Hypertension (High Blood Pressure)

Provided herein is a method of treating or ameliorating heart failure caused by hypertension, or high blood pressure, by administering a poloxamer 188, such as a purified poloxamer 188, to a subject. Hypertension, or high blood pressure, is characterized by an increase of blood pressure on the artery walls. Due to this increased pressure, hypertension results in remodeling of the cardiac and vascular tissue in an attempt to normalize the stress on the heart and arterial walls, which can impact proper heart functioning. Hypertension is a risk factor for hypertensive heart disease and coronary artery disease due to the strain on the heart muscle from the increased blood pressure, and is a probable contributing factor to the majority of cases of systolic heart failure and in at least 25% of the incidence of diastolic heart failure. Provided herein are methods of using a poloxamer 188, such as a purified poloxamer 188, for treating, ameliorating or reducing hypertension induced by continued or acute increased blood pressure. Subjects or patients with Hypertension can be administered a Poloxamer 188, such as a purified Poloxamer 188.

The methods and uses provided herein are for treating subjects that typically exhibit symptom(s) associated with hypertension. In particular, the methods herein can be used to treat patients with chronic or acute hypertension. Generally, prior to treatment, patients are selected that exhibit one or more signs or symptoms associated with hypertension. It is within the level of a skilled physician to diagnose hypertension. The most significant indicator of hypertension is the blood pressure measurement when assessed using a sphygmomanometer, typically used in conjunction with a stethoscope. The majority of subjects that have hypertension, including chronic or hypertension, do not exhibit any clinical symptoms; moreover, severe hypertension, where blood pressure reaches a critically elevated level, can be associated with one or more other symptoms such as severe headache, fatigue, vision problems, chest pain, difficulty breathing, irregular heartbeat, and blood in the urine. Selection of a subject having hypertension failure for treatment with a poloxamer 188, such as a purified poloxamer 188, in the methods provided herein can be based on arterial pressure as assessed using a sphygmomanometer, clinical symptoms, hemodynamic and ventriculographic measurements, or levels of proinflammatory biomarkers for hypertension, for example in the blood.

In particular, provided herein are methods of using a poloxamer 188, such as a purified poloxamer 188, for treating, ameliorating or reducing hypertension induced by increased blood volume or narrowing of the blood vessels, which increase pressure on blood vessel walls. Subjects or patients with hypertension can be administered a poloxamer 188, such as a purified poloxamer 188, including an LCMF poloxamer 188. The poloxamer can be administered in accord with the regimens provided herein.

2. Selection of Subjects for Treatment a. Selecting Subjects with Heart Failure

Selection of a subject having heart failure for treatment with poloxamer 188, such as a purified poloxamer 188, in the methods provided herein can be based on clinical symptoms, such as breathlessness, orthopnoea (shortness of breath experienced when lying flat), paroxysmal nocturnal dyspnoea (severe shortness of breath that occurs most often at night), reduced exercise tolerance, fatigue and tiredness, and ankle and abdomen swelling, and less commonly with nocturnal cough, wheezing, weight gain, weight loss, bloated feelings, loss of appetite, confusion, depression, palpitations and fainting, echocardiographic and doppler measurements (Borlaug and Paulus. Eur Heart J. 32:670-679 (2011)), cardiac magnetic resonance, single-photon emission computed tomography and radionuclide ventriculography (SPECT) (Beller and Heede. J Cardiovasc Transl Res 4: 416-424 (2011)), positron emission tomography (PET), coronary angiography, cardiac computed tomography (Miller et al. N Engl J Med 359:2324-2336 (2008)), cardiac catheterization and endomyocardial biopsy (Cooper et al Eur Heart J 28:3076-3093 (2007)), the expression of natriuretic peptides, including B-type Natriuretic peptide (BNP) and N-terminal pro B-type natriuretic peptide (nt-proBNP) (Krishnaswamy et al. Am J Med111:274-279 (2001)), blood or urine tests for biomarkers, including but not limited to troponin-I (TnI), TNFα, IL-6, CRP, MMP-2, and PINP, chest radiography/X-ray, blood make-up, including, but not limited to, sodium, potassium, and creatinine levels, and exercise and genetic testing. Such techniques are well known to one of skill in the art.

Selection of a subject having heart failure for treatment with poloxamer 188, such as a purified poloxamer 188, in the methods provided herein can be based on hemodynamic and ventriculographic measurements, including aortic and LV pressures, peak rate of change of LV pressure during isovolumic contraction and relaxation, LV end-diastolic pressure, cardiac output (CO), LV stroke volume (SV), systemic vascular resistance (SVR), LV end-systolic (ESV) and end-diastolic (EDV) volumes, and LV ejection fraction (EF). Hemodynamic and ventriculographic measurements can be assessed or calculated using standard methods (Sabbah et al. (1991) Am. J. Physiol. 260 (Heart Circ. Physiol. 20): H1379-H1384; Zaca et al. (2007) J. Am. Coll. Cardiol., 50:551-557) and are known to those of skill in the art.

Selection of a subject having heart failure for treatment with poloxamer 188, such as a purified poloxamer 188, in the methods provided herein can be assessments using on echocardiograms and Doppler echocardiography, and include LV fractional area of shortening (FAS), which is a measure of LV systolic function, LV thickness, which can be used to calculate cardiac wall stress, mitral inflow velocity, which can be used to calculate peak mitral flow velocity in early diastole (PE), peak mitral inflow velocity during left atrial (LA) contraction (PA), the ratio of PE to PA, the time-velocity integral of the mitral inflow velocity waveform representing early filling (Ai), the time-velocity integral representing LA contraction (Ai), the ratio of Ei/Ai, and deceleration time (DCT) of early mitral inflow velocity. Echocardiographic and doppler measurements can be assessed or calculated using standard methods (Sabbah et al. (2007) Am. J. Cardiol., 99:41A-46A) and are known to those of skill in the art.

Selection of a subject having heart failure for treatment with poloxamer 188, such as a purified poloxamer 188, in the methods provided herein can be based on assessments of subjects at risk for heart disease, including subjects with comorbidities that increase the incidence of heart disease such as metabolic syndrome (ie. hypertension, dyslipidemia, obesity and diabetes), increased age, those with a genetic predisposition for the disease, such as those with heritable disorders, and those susceptible to environmental factors. In the case of diabetes, left ventricular diastolic dysfunction can represent the first stage of diabetic cardiomyopathy (Raev, Diabetes Care 17:633-639 (1994)).

In exemplary methods to select a subject with a heart dysfunction or heart failure for treatment harvesting of peripheral venous blood samples are generally performed prior to, during, or following treatment of the subject with a poloxamer 188, such as a purified poloxamer 188. In exemplary methods of monitoring therapy for heart dysfunction or heart failure, harvesting of the peripheral venous blood samples from the subject can be performed before, during or after the subject has received one or more treatments with a poloxamer 188, such as a purified poloxamer 188.

Selection of a subject having heart failure for treatment with poloxamer 188, such as a purified poloxamer 188, in the methods provided herein can be based on the presence of biomarkers in venous blood samples, such as, for example, blood serum. Exemplary biomarkers for heart failure include, but are not limited to, N-terminal pro-brain natriuretic (nt-pro BNP), troponin-I (Tn-I), matrix metalloproteinase-2 (MMP-2), MMP-9, Interleukin 6 (IL6), C-reactive protein (CRP), TNF-alpha (TNFα), measures of oxidative stress, including isoprostane, derivatives of reactive oxygen metabolites, IPGF2, bilirubin, and 8-OHdG. Selection of subjects can be based on presentation with a change in biomarker protein expression from normal levels, including an increase or a decrease. For example, a patient with increased Tn-I expression indicates that the patient has experienced cardiomyocyte injury and death, and thus, may have a more severe form of heart failure.

Assays for use in the methods provided herein are those in which a biomarker of heart dysfunction, or heart failure, present in the sample is detected using an antibody sandwich enzyme-linked immunosorbent assay (ELISA). ELISA is a biochemical experimental method based on enzymatic reactions using a binding partner, such as an antibody (e.g., monoclonal or polyclonal antibodies) or other binding partner, to detect the plasma levels of specific proteins such as inflammatory proteins, or biomarkers, for example, troponin-I (Tn-1). ELISA based methods can be used for quantitative or semi-quantitative detection of the amount of troponin-I that binds to a troponin-I antibody in a sample, such as a fluid sample from a subject having heart failure or suspected of having heart failure. The use of solid phase binding assays can be used when troponin-I is detected in a bodily fluid. For example, ELISA assays for use in the methods herein include those where an anti-troponin-I antibody is used as a binding partner to detect troponin-I in blood plasma. Typically, ELISA protocols include detection systems that make the presence of the markers visible, to either the human eye or an automated scanning system, for qualitative or quantitative analyses.

Selection of a subject having heart failure for treatment with poloxamer 188, such as a purified poloxamer 188, in the methods provided herein can be based on the presence of biomarkers in excretions, for example urinary excretions. Exemplary biomarkers for heart failure include, but are not limited to, 8-iso-prostaglandin F2 alpha (IPGF2), which is a chemically stable and quantitative measure of oxidative stress, N-terminal pro-BNP (N-BNP), collagen alpha1 (I and III) (Zimmerli et al. 7:290-298 (2008)) and are well known to those of skill in the art. Selection of subjects can be based on presentation with a change in biomarker protein expression from normal levels, including an increase or a decrease.

b. Selecting Subjects with Systolic Dysfunction

Systolic dysfunction, also known as heart failure with reduced (left ventricular) ejection fraction (HFREF), develops from the interactions between genetic factors and accumulated cardiac insults. The selection of a subject having systolic heart failure for treatment with poloxamer 188, such as a purified poloxamer 188, in the methods provided herein can be based on echocardiographic evidence of depressed left ventricular systolic function. For example, systolic dysfunction can be assessed in subjects who present with eccentric hypertrophy, which is a disproportionate increase in ventricle volume coupled with little increase in wall thickness that can result in volume and pressure overload. Such subjects can be selected based on alterations to LV end systolic volume and/or LV end-systolic pressure.

The selection of a subject having subtypes of non-ischemic systolic heart failure for treatment with poloxamer 188, such as a purified poloxamer 188, in the methods provided herein can be based on a collection of clinical features that reflect their underlying pathophysiology, including, but not limited to, their clinical course and rate of response to treatments.

The selection of a subject having systolic heart failure for treatment with poloxamer 188, such as a purified poloxamer 188, in the methods provided herein can be based on presence of biomarkers in venous blood samples, such as, for example, blood serum or urinary excretions. Exemplary biomarkers for systolic heart failure include, but are not limited to, 8-iso-prostaglandin F2 alpha (IPGF2), which is known to correlate with the severity of systolic heart failure and is inversely correlated with ejection fraction. In another example, an exemplary biomarker to ischemic systolic heart failure is 8-hydroxy-2'-deoxyguanosine (8-OHdG), a marker of systemic oxidatively generated DNA damage, whose level in urine correlates with the severity of ischemic systolic heart failure as assayed by the number of diseased vessels visualized on coronary angiography (Nagayoshi et al., Free Radic Res 2009; 43(12):1159-1166). Selection of subjects can be based on presentation with a change in biomarker protein expression from normal levels, including an increase or a decrease.

The selection of a subject having systolic heart failure for treatment with poloxamer 188, such as a purified poloxamer 188, in the methods provided herein can be based on changes to hemodynamic, ventriculographic and doppler-echocardiographic readings including, but not limited to systolic aortic pressure, mean aortic pressure, peak rate of change of LV pressure during isovolumic contraction, left ventricular ejection fraction, left ventricular end-systolic volume, cardiac output, stroke volume, fractional area of shortening, and the ratio the ratio of integral of mitral inflow velocity in early diastole (Ei) to integral of mitral inflow velocity during left atrial contraction (Ai) (Ei/Ai).

c. Selecting Subjects with Diastolic Dysfunction

Diastolic dysfunction refers generally to a condition in which abnormalities in mechanical function are present during diastole, and which can occur in the presence or absence of heart failure. Diastolic dysfunction presents as concentric hypertrophy where, although there is no change or a slight decrease in the radius of the ventricular chamber, the walls of the heart thicken and are, thus, capable of generating increased pressure with greater force. The heart muscle subsequently becomes 'stiff', which can impair ventricle filling. Diastolic dysfunction is most commonly a chronic condition and may be well tolerated by the affected individual.

Because ejection fraction is preserved in diastolic heart failure, diagnosis is more challenging than the diagnosis of systolic heart failure, largely because it is a diagnosis that relies on exclusion of other potential non-cardiac causes of the patient's clinical symptoms. Additionally, clinical examination is not sufficient to distinguish diastolic heart failure from systolic heart failure. Diastolic dysfunction is most often diagnosed in asymptomatic patients using Doppler echocardiography.

The selection of a subject having diastolic heart failure for treatment with a poloxamer 188, such as a purified poloxamer 188, in the methods provided herein can be based on a normal or preserved left ventricular (LV) end diastolic volume, normal ejection fraction, delayed active relaxation, and increased passive stiffness of the left ventricle. (Owan et al., N Eng J Med 2006; 355:251-9; Zile et al., Circulation 2002; 105:1387-93). The selection of a subject having diastolic heart failure can be characterized by dilated cardiomyopathy in which the ventricles are dilated, resulting in thinner muscle, reduced contractility and failure of the ventricle to fill properly. Furthermore, this diastolic dysfunction can co-exist with or without abnormalities in systolic function (Zile et al. (2003) JACC 41:1519-1522).

The selection of a subject having diastolic heart failure for treatment with poloxamer 188, such as a purified poloxamer 188, in the methods provided herein can be based on a the expression of biomarkers for heart failure or heart dysfunction. For example, interleukin-16 (IL-16) levels can be used to determine the type of heart failure. IL-16 levels were specifically elevated in diastolic heart dysfunction, compared to systolic dysfunction and controls, in a rat model of heart failure and in human patients (Tamaki et al. PloS ONE 8(7):e68893 (2013)) and IL-16 levels positively correlated with LVEDP. The selection of a subject having diastolic heart failure can be based on the elevated IL-16 in the presence of elevated LVEDP. In another example, the selection of a subject having diastolic heart failure can be based on the elevated BNP in the blood plasma in the presence of normal ejection fraction.

Like all heart failure patients, patients with systolic dysfunction are heterogenous with respect to etiology, prognosis, and response to therapy, and the ability to identify patients likely to respond to medical therapy remains limited. Several characteristics distinguish systolic dysfunction and diastolic dysfunction patients from each other. The selection of a subject having diastolic heart failure for treatment with Poloxamer 188, such as a purified Poloxamer 188, in the methods provided herein can be based on demographic characteristics, for example, patients with diastolic dysfunction are more likely to be women, older, less likely to have ischemia and more likely to have comorbid systolic hypertension (Little and Zile. Circulation 5:669-671 (2012)). In another example, selection of patients with diastolic dysfunction can be based on hemodynamic, ventriculographic and doppler-echocardiographic readings. The selection of a subject having diastolic heart failure for treatment with poloxamer 188, such as a purified poloxamer 188, can be based on changes to hemodynamic, ventriculographic and doppler-echocardiographic readings including, but not limited to mean aortic pressure, peak rate of change of LV pressure during isovolumic relaxation, left ventricular ejection fraction, left ventricular end-diastolic volume, cardiac output, stroke volume, fractional area of shortening, and the ratio the ratio of integral of mitral inflow velocity in early diastole (Ei) to integral of mitral inflow velocity during left atrial contraction (Ai) (Ei/Ai).

3. Monitoring Subjects for Treatment

A poloxamer 188, such as a purified poloxamer 188, provided herein can reduce, lessen or ameliorate heart dysfunction, and thereby also can prevent or ameliorate diseases and conditions associated with heart disease, including, but not limited to, diastolic and/or systolic dysfunction, ischemic heart failure, myocardial infarction, and hypertension. Heart function of the subject can be monitored over time to assess whether a decrease in cardiac failure has been achieved over the course of therapy with a poloxamer 188, such as a purified poloxamer 188, provided herein.

G. Combination Treatments

Poloxamer 188, such as any Poloxamer 188 described herein, can be administered in combination with therapeutics previously utilized to treat heart failure, in order to improve the efficacy of the Poloxamer 188 compound on its own. Typically, such treatments include, but are not limited to, methods of treatment of physiological and medical conditions described and listed herewith. The compositions provided herein can be further co-formulated or co-administered with, prior to, intermittently with, or subsequent to, other therapeutic or pharmacologic agents or treatments, such as treatments where normalized or improved left ventricular end-diastolic or end-systolic pressure and volume are desired. Poloxamer 188, such as any Poloxamer 188 described herein, can be used in the treatments of heart failure, for example chronic, acute or ischemic heart failure. Poloxamer 188 is particularly well suited for treating patients with heart failure, including but not limited to systolic heart failure because of its ability to impart long-lasting, significant improvements to a variety of measures of systolic heart failure including. Poloxamer 188, such as any Poloxamer 188 described herein, also can be used to treat heart failure related to a primary disease state such as, for example duchenne muscular dystrophy.

A preparation of a second agent or agents or treatment or treatments can be administered at once, or can be divided into a number of smaller doses to be administered at intervals of time. Selected agent/treatment preparations can be administered in one or more doses over the course of a treatment time for example over several hours, days, weeks, or months. In some cases, continuous administration is useful. It is understood that the precise dosage and course of administration depends on the indication and patient's tolerability. Generally, dosing regimens for second agents/treatments herein are known to one of skill in the art.

Poloxamer 188, such as a purified poloxamer 188 described herein, can also be used in conjunction with currently available therapeutics, including, but not limited to: a diuretic, loop diuretic, a potassium sparing agent, a vasodilator, an ACE inhibitor, ARBs (angiotensin receptor blockers), an angiotensin II antagonist, Aldosterone antagonist, a positive inotrophic agent, a phosphodiesterase inhibitor, a beta-adrenergic receptor antagonist, a calcium channel blocker, a nitrate, an alpha blocker, a central alpha antagonist, a statin, a cardiac glycoside, Digoxin, Nitrates, chlorthalidone, amlodipine, lisinopril, doxazosin, or a combination of these agents. Additionally, poloxamer 188, such as a purified poloxamer 188 described herein, also can be used in conjunction with mechanical devices, including: implantable pacemakers, defibrillators, and left ventricular assist devices (LVAD). With the possible exception of the LVAD, when used individually, these therapies prolong life, but do not stop, or reverse, disease progression and deterioration of heart function.

H. EXAMPLES

The following examples are included for illustrative purposes only and are not intended to limit the scope of the invention.

Example 1

Preparation and Administration of Long Circulating Material Free (LCMF) Poloxamer 188

A. Supercritical Fluid Extraction (SFE) Process

A multi-step extraction batch process of poloxamer 188 was performed with extraction conducted at a pressure of 247±15 atm (approximately 200-260 bars) and a controlled step-wise increase of methanol of 7.4, 9.1 and 10.7 weight % methanol. Before purification, the poloxamer 188 raw material (BASF Corporation, Washington, N.J.) was characterized by Gel Permeation Chromatography (GPC). Molecular weight analysis demonstrated that raw material had an average molecular weight of the main peak of about 8,500±750 Da, no more than 6.0% low molecular weight (LMW) species of less than 4,500 Da and no more than 1% high molecular weight species (HMW) greater than 13,000 Da. In addition, the polydispersity was no more than 1.2.

A 50-L, high pressure, stainless steel, extractor vessel was charged with 14 kg of commercial grade poloxamer 188 (BASF Corporation, Washington, N.J.) and 7 kg of methanol, pressurized with $CO_2$ (49±10 atm, i.e. 720±147 psi) (Messer France, S. A. S., Lavera, France) and heated to 35° C. to 50° C. for 40-80 minutes until a homogenous solution was obtained. $CO_2$ (supplied either from a main supply tank or via recycling through an extraction system), was cooled in a heat exchanger and fed into a temperature-controlled, high pressure, stainless steel, solvent reservoir. A high-pressure pump increased the pressure of liquid $CO_2$ to the desired extraction pressure. The high pressure $CO_2$ stream was heated to the process temperature by a second heat exchanger. Methanol (Merck KGaA, Darmstadt, Germany) was fed from a main supply tank into the $CO_2$ solvent stream to produce the extraction methanol/$CO_2$ cosolvent, which was fed through inlet systems into the extractor vessel as a fine mist at a pressure of 247±15 atm (3600±psi) or 240 to 260 bars and a temperature of 40° C.

A 7.4% methanol/$CO_2$ extraction cosolvent was percolated through the poloxamer solution for 3 hours at a methanol flow rate typically at 8 kg/hr (range 6.8 kg/hr to 9.2 kg/hr; 108 kg/hr total flow rate). The extraction continued with a 9.1% methanol/$CO_2$ co-solvent for 4 more hours at a methanol flow rate typically at 10 kg/hour (range of 8.5 kg/hr to 11.5 kg/hr; 110 kg/hr total flow rate). The extraction further continued with a 10.7% methanol/$CO_2$ cosolvent for 8 more hours at a methanol flow rate typically at 12 kg per hour (range of 10.2 kg/hr to 13.8 kg/hr; 112 kg/hr total flow rate). Throughout the extraction process, extraction of soluble species were continuously extracted from the top of the extractor. The extraction solvent was removed from the top of the extractor and passed through two high pressure, stainless steel, cyclone separators arranged in series to reduce system pressure from 247 atm (3600 psi) to 59 atm (870 psi) and then from 59 atm to 49 atm (720 psi) and to separate $CO_2$ from the methanolic stream. The separated $CO_2$ was condensed, passed through the heat exchanger and stored in the solvent reservoir. Pressure of the methanol waste stream was further reduced by passing through another cyclone separator. The purified poloxamer 188 remained in the extractor.

After extraction, the purified poloxamer 188 solution was discharged from the bottom of the extractor into a mixer/dryer unit equipped with a stirrer. The poloxamer 188 product was precipitated under reduced pressure via a Particle from Gas Saturated Solutions (PGSS) technique. The precipitate contained approximately 20% to 35% methanol. The purified poloxamer 188 was dried under vacuum at not more than 40 or 45° C. to remove residual methanol. The feed yield of the product gave an average yield of 65%.

Molecular weight analysis of the purified product as determined by GPC demonstrated that the purified product met the acceptance specifications. There was an average molecular weight of the main peak of about 8,500±750 Da and an average molecular weight average of 8,500±750 Da, no more than 1.5% low molecular weight (LMW) species of less than 4,500 Da and no more than 1.5% high molecular weight species (HMW) greater than 13,000 Da. In addition, the polydispersity was no more than 1.05. Thus, the results showed that the procedures resulted in a measurable reduction in the LMW species, and an improvement in the polydispersity of the purified product.

The resulting purified poloxamer188 was formulated into a clear, colorless, sterile, non-pyrogenic, aqueous solution containing the purified poloxamer at 150 mg/ml, sodium chloride at 3.08 mg/ml, sodium citrate (dihydrate) at 2.38 mg/ml, and citric acid anhydrous at 0.366 mg/ml in water for injection. The solution was sterile filtered and filled into 100 ml glass vials, covered with a nitrogen blanket, and closed with a butyl rubber stopper and aluminum overseal. The resulting osmolarity of the solution was approximately 312 mOsm/L. The LCMF poloxamer-188 composition did not contain any bacteriostatic agents or preservatives.

B. Characterization of the Plasma Concentration Time Course Following Intravenous Administration of Purified (LCMF) Poloxamer 188 Using HPLC-GPC (Method 1)

Purified LCMF poloxamer 188 generated as described above was administered intravenously to 62 healthy volunteers as part of assessment to determine its effect on the QT/QTc interval. Eight of the 62 subjects were randomly selected for quantitative analysis of the plasma poloxamer levels using an HPLC-GPC method. Following administration, blood samples were obtained by venipuncture into heparin anti-coagulated tubes at baseline, during drug administration (hours 1, 2, 3, 4, 5, and 6) and post administration at hours 1, 1.5, 2, 2.5, 5, 6, and 18. Plasma was separated by centrifugation and stored frozen until analysis. The purified poloxamer 188 was administered as either a high dose of a loading dose of 300 mg/kg/hr for one hour followed by a maintenance dose of 200 mg/kg/hr for 5 hours or a lower dose of 100 mg/kg for 1 hour followed by 30 mg/kg/hr for 5 hours. A mean maximum concentration (Cmax) of the administered purified poloxamer 188 of 0.9 mg/mL was attained by the end of the one hour loading infusion. The mean concentration at steady state (Css) was about 0.4 mg/ml was attained during maintenance infusion. The plasma concentration declined rapidly following discontinuation of the maintenance infusion. The LCMF product purified as described above did not demonstrate the long circulating higher molecular weight material, observed with prior poloxamer 188 and as defined herein, in the plasma.

Figure 7A:
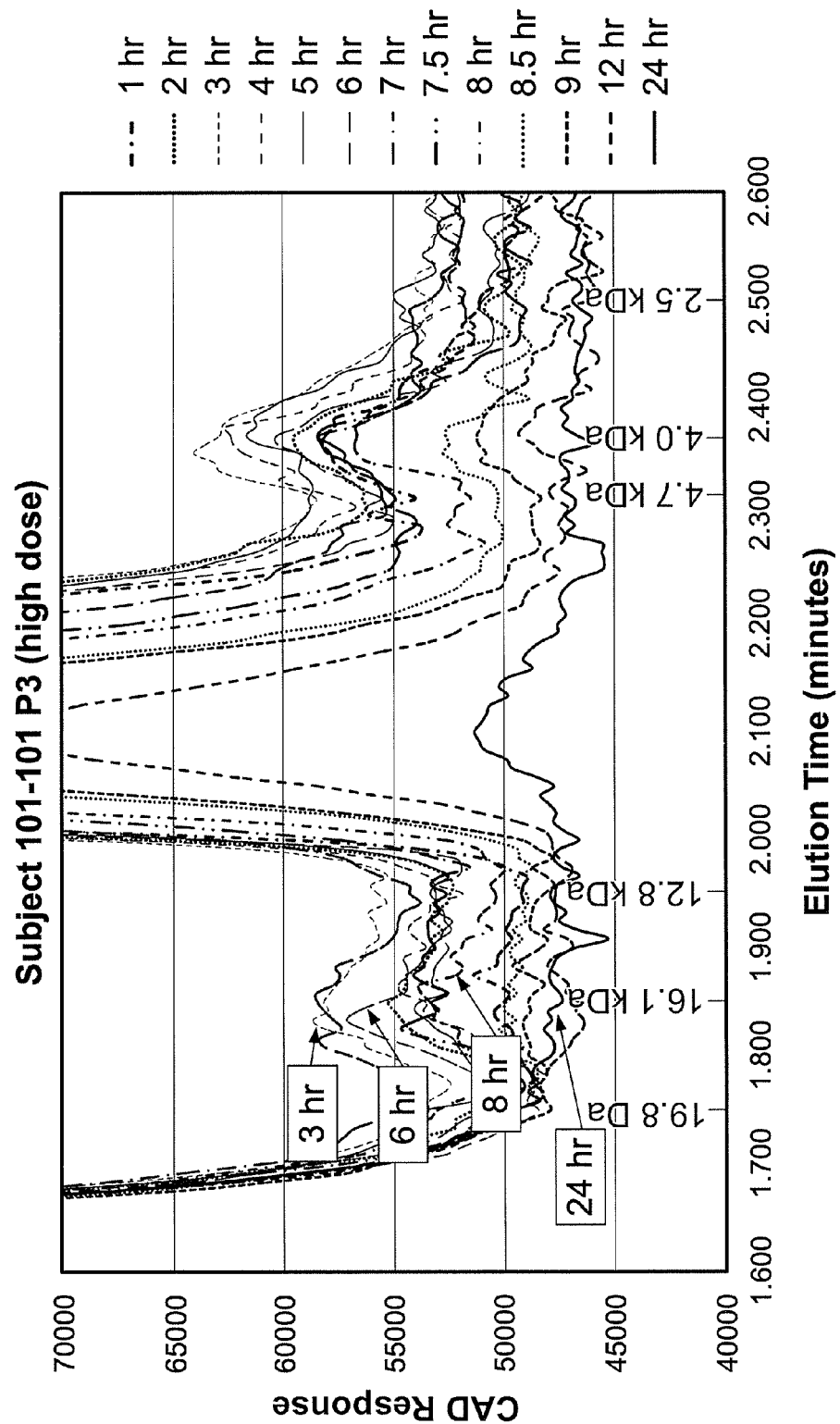
FIG. 7A-B shows enlarged HPLC-GPC chromatograms depicting the molecular weight distribution of components in plasma over time.
Figure 7B:
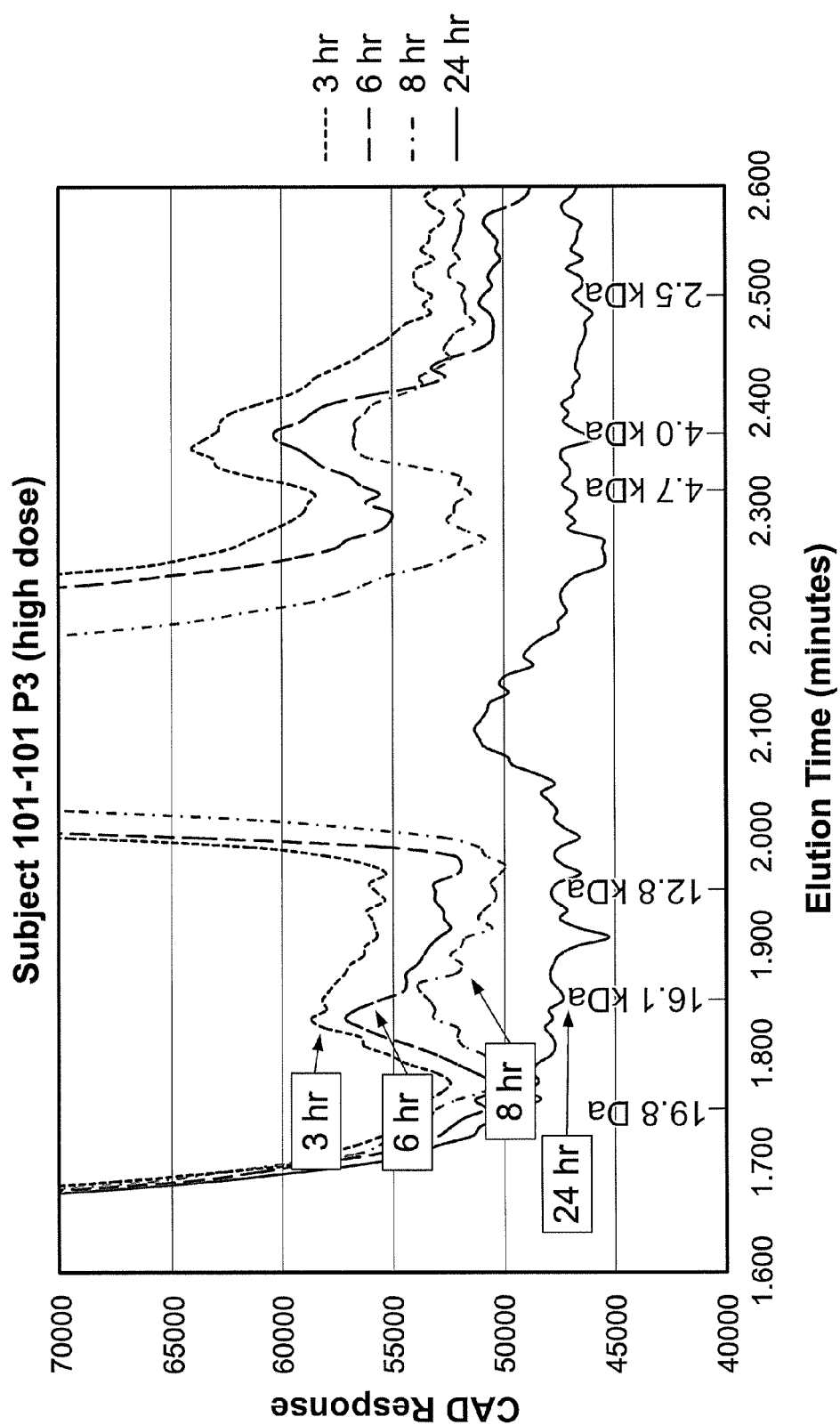

To confirm the absence of such long circulating material in plasma, plasma from subjects receiving the higher dose were similarly studied using HPLC-GPC. FIGS. 7A and 7B show serial HPLC-GPC of plasma obtained at various time points following administration of the purified LCMF poloxamer 188 for a single subject. FIG. 7A shows the chromatograms at all time points, while FIG. 7B shows selected time points for comparison. In both figures, the chromatogram is enlarged to show the high molecular weight portion (19.8 K Daltons-12.4 K Daltons) of the polymeric distribution. Also shown are the main peak portion (12.8-4.7 K Da) and the lower molecular weight portion (4.7-2.5 K Da). The HPLC-GPC method quantifies plasma levels based on the height of the eluting peak relative to standards of known concentration (i.e. the higher the eluting peak, the higher the plasma level). The GPC method also identifies the molecular weight range by comparison of the sample elution time to that of standards of known molecular weight.

The chromatograms show that over time the high molecular weight portion of the poloxamer 188 polymeric distribution declines in relative proportion to the main peak and lower molecular weight components. Thus, the polymeric distribution shows that the high molecular weight portion clears from the circulation in a substantially uniform manner. The results also show that the higher molecular weight species do not exhibit a longer circulating half-life (relative to the other polymeric components) and do not accumulate in the circulation following intravenous administration.

C. Comparison of the Plasma Concentration Time Course Following Intravenous Administration of Purified LCMF Poloxamer 188 and Purified LCM-Containing Poloxamer 188 by HPLC-GPC 1. Administration of the Long Circulating Material (LCM)-Containing Poloxamer 188

The (LCM-containing) purified poloxamer 188 was administered to 6 healthy volunteers as an intravenous loading dose of 100 mg/kg/hr for one hour followed by 30 mg/kg/hr for 48 hours as part of a safety and pharmacokinetics study (Grindel et al). Blood samples were obtained by venipuncture into EDTA anticoagulated tubes prior to drug administration (baseline), during administration (at 1 hour, 6 hours, 12 hours 18 hour 24 hours 36 and 48 hours) and at 30 minutes, 1 hour, 1.5 hours, 2 hours, 4 hours, 6 hours, 8 hours, 12 hours, 14 hours, 20 hours and 24 hours post drug administration. Plasma was separated and stored frozen until analysis using an HPLC-GPC method. Analysis of the plasma samples revealed the clearance kinetics of the main peak and the HMW peak for the (LCM-containing) purified poloxamer 188

HMW Peak (the Long Circulating Material)

Following administration at the above dose, the HMW component (detected in the HPLC-GPC assay as a peak of approximately 16,000 Daltons) was accumulating during the drug administration period and did not reach its mean Cmax concentration of 225 µg/ml (n=6) until 2 hours after the end of drug administration. By 6 hours after discontinuation of infusion, mean plasma levels remained at 202 ug/ml, a concentration that had declined by only about 10% from the Cmax value. Over the 24 hour post infusion blood collection period, mean plasma levels only declined by 22.5% to a plasma concentration of 165 µg/ml. Based on these changes in the plasma concentration time course an elimination half-life of >48 hours is estimated.

Main Peak

Following administration at the dose above, the main peak achieved an apparent mean steady state concentration of 522 µg/ml (n=6) that was maintained during drug infusion. One hour after discontinuation of infusion, plasma levels dropped from the steady state concentration by 52% to 255 µg/ml. By 6 hours after discontinuation, plasma levels had dropped by 85% to 81 µg/ml. By 24 hours post infusion, plasma levels declined by 96% to a plasma concentration of about 19 µg/ml (n=6). Based on these changes in the plasma concentration time course the half-life is estimated to be about 5 hours.

2. LCMF Poloxamer 188 (Prepared as Described Above)

LCMF poloxamer was administered to 62 healthy volunteers at a dose of 300 mg/kg for one hour followed by 200 mg/kg/hr for 5 hours as part of the assessment to determine its effect on the QT/QTc interval as previously described. Eight of the 62 subjects were randomly selected for quantitative analysis of the plasma poloxamer levels using a similar HPLC-GPC method as described in part (B) above but with improved linearity at lower plasma levels.

HMW Peak

Following administration at the above dose, the HMW component, which was detected in the HPLC-GPC assay as a peak of approximately 16,000 Daltons, accumulated to a small extent during drug administration, and achieved its Cmax (mean value of 117 µg/ml, n=8) by end infusion. By 1 hour after discontinuation of drug administration, plasma levels had declined by 27% from the Cmax value to 86 µg/ml. By 6 hours after the end of drug administration, mean plasma levels had declined by 71% from the Cmax value to 34 µg/ml. By 18 hours after the end of infusion, the mean plasma level had declined by 82% to a concentration of 19 µg/ml (n=8). Based on these changes in the plasma concentration over time, the elimination half-life for the HMW component was estimated to be between 6-9 hours.

Main Peak

Following administration at the dose above, the main peak achieved an apparent mean steady state concentration of 2,637 µg/ml that was maintained during the 6 hour infusion period (n=8). One hour after discontinuation of infusion, mean plasma levels had decreased from steady state by 67% to 872 µg/ml and by 6 hours after discontinuation, mean plasma levels had declined by 93% (from steady state) to 184 µg/ml. By 18 hours after discontinuation of infusion, mean plasma levels declined by over 98% (from steady state) to a plasma concentration of about 34 µg/ml (n=6). Based on these changes in the plasma concentration time course, the elimination half-life is estimated to be about 3 hours.

c. Summary Comparison Table

A comparison of the relative rates of clearance from the plasma at similar time points following administration is shown in TABLE 1 below. The data demonstrate a marked difference in the rate of decline in plasma concentration between (LCM-containing) purified poloxamer 188 and the LCMF poloxamer 188, demonstrating that LCMF poloxamer 188 clears faster. The difference is apparent for the HMW peak and for the main peak. The difference is most apparent for the HMW peak. This shows that the LCMF poloxamer is different from the LCM-containing poloxamer of the prior art.

TABLE 1

|  | HMW Peak | | Main Peak | |
| --- | --- | --- | --- | --- |
|  | LCMF | (LCM-containing) purified poloxamer 188 | LCMF | (LCM-containing) purified poloxamer 188 |
| % decrease 1 hr | 27 | 0 | 67 | 52 |
|  | 71 | 10 | 93 | 85 |
| Apparent elimination t½ | 6-9 hours | >48 hours | About 3 hours | About 5 hours |

D. Analytical Data Confirming that Purified LCMF Poloxamer 188 is Different from Purified Poloxamer 188 Containing LCM 1. Analytical Test (RP-HPLC Assay) to Compare Various Poloxamers In reversed phase chromatography there is a hydrophobic stationary phase (the column) and a more polar mobile phase. Because of this "reversed" phase condition, RP-HPLC is commonly used to separate compounds based on relative hydrophobicity. More hydrophobic compounds exhibit a longer column retention time compared to more hydrophilic compounds.

The following HPLC conditions were used to compare column retention times for various poloxamers with known differences in their hydrophilic/lipophilic balance (HLB), along with purified poloxamer containing LCM and the LCMF poloxamer 188:

| Column | Xterra RP18, 3.5 um, 4.6 × 100 mm |
| --- | --- |
| Mobile Phase | A: 0.1% HOAc in Water<br>B: Acetonitrile |

| Gradient | Time | % B |
| --- | --- | --- |
|  | 0 | 50 |
|  | 1.0 | 50 |
|  | 15.0 | 90 |
|  | 16.0 | 90 |
|  | 16.1 | 50 |
|  | 20.0 | 50 |

| Flow Rate | 0.50 ml/min |
| --- | --- |
| Column Temp | 40° C. |
| ELS*Detection | $N_2$: 0.5 liter/minute,<br>Nebulizer: 75° C., Evaporator: 75° C. |
| Sample Preparation | Drug Product - No dilution<br>Purified Poloxamer 188, 150 mg/mL in 10 mM NaCitrate pH 6 |
| Injection Volume | 10 µL |

*ELS = evaporative light scattering

Results

The results show that the LCMF poloxamer 188 is different from the prior art purified poloxamer 188. It has different pharmacokinetic properties, which reflect that it is more hydrophilic than the prior art material that contains the long circulating material.

FIG. 9 shows the RP-HPLC chromatograms for a highly hydrophilic polymer (PEG 8000), the LCMF poloxamer 188, the LCM-containing purified poloxamer 188, and two poloxamers with decreasing HLB values (increasing hydrophobicity), Poloxamer 338 and Poloxamer 407, respectively. The most hydrophilic polymer, PEG 8000, exhibits little retention on the column consistent with its highly hydrophilic nature. Poloxamer 338 (HLB>24) and Poloxamer 407 (HLB 18-23) exhibit far longer retention times (add the $t_R$ and k' values) in accord with their known HLB values. The LCMF purified poloxamer 188 elutes more quickly than the LCM-containing purified poloxamer 188, (the average $t_R$ and k' for LCMF purified poloxamer is about 8.8 (8.807) and about 3.2 (3.202), respectively, compared to about 10.0 (9.883) and 3.7 (3.697) for LCM containing purified poloxamer) indicating that the LCMF poloxamer 188 is relatively more hydrophilic than the LCM containing purified poloxamer 188.

FIG. 10 shows the chromatograms for 3 different lots of purified LCMF poloxamer 188 and two (2) different lots of purified (LCM-containing) poloxamer 188. These results demonstrate a robust reproducibility for the different lots of materials, and show that the difference between the two materials cannot be accounted for by assay variability. These results demonstrate that the polymeric distribution of LCMF poloxamer 188 is more hydrophilic than purified poloxamer 188.

2. The Different Pharmacokinetic Behavior of the LCMF Purified Poloxamer and the LCM-Containing Poloxamer Correlate with the Differences in their Hydrophilicity As described herein (see, e.g., Example 1B, above, and FIGS. 9-10) and TABLE 1), the LCMF poloxamer 188 exhibits a markedly different pharmacokinetic behavior following administration to human subjects when compared to purified poloxamer 188, which contains the long circulating material (LCM) following in vivo administration. The data provided in this example indicate that LCMF poloxamer 188 is more hydrophilic compared to purified poloxamer 188 that gives rise to the long circulating material.

The polymeric size distribution of purified variants of poloxamer 188 purified LCM-containing poloxamer 188, and the LCMF poloxamer 188 is similar with regard to size as shown by HPLC-GPC. Both meet the criteria:

| Test Attribute | Acceptance Criteria | Test Method |
|---|---|---|
| Molecular Weight Analysis | | |
| Peak MW | 8500 ± 750 Da | HPLC-GPC |
| Weight Average MW | 8500 ± 750 Da | |
| % LMW (<4500 Da) | NMT* 1.5% | |
| % HMW (>13000 Da) | NMT 1.5% | |
| Polydispersity | NMT 1.05 | |

*NMT = Not More Than

While the polymeric size distribution, as shown by HPLC-GPC, of both purified poloxamers is similar, as demonstrated by the RP-HPLC herein, the molecules that comprise the polymeric distribution of LCMF poloxamer 188 are more hydrophilic. When injected into an animal, a more hydrophilic polymeric distribution clears from the circulation at a faster rate. This accounts for the decreased presence of a long circulating material in the LCMF poloxamer 188 preparation. The results also indicate that, as observed and described above, the main peak of the polymeric distribution clears faster. For example, the plasma concentration time course data from a clinical trial show a shorter elimination half-life for the main peak and the high molecular weight peak of the LCMF poloxamer 188 compared to the purified poloxamer 188 containing LCM.

Since the rheologic, cytoprotective, anti-adhesive and antithrombotic effects of P188 are optimal within the predominant or main copolymers of the distribution, which are approximately 8,400 to 9,400 Daltons (which have a circulating half life of about 4-7 hours), the presence of larger, more hydrophobic, long circulating half-life components of poloxamer 188 is not desirable. For example, among the desired activities of P188 is its rheologic effect to reduce blood viscosity and inhibit red blood cell (RBC) aggregation, which account for its ability to improve blood flow in damaged tissues. In contrast, more hydrophobic, higher molecular weight poloxamers such as P338 (also called Pluronic® F108) and P308 (Pluronic® F98), increase blood viscosity and RBC aggregation (Armstrong et al. (2001) *Biorheology*, 38:239-247). This is the opposite effect of P188 and indicates that higher molecular weight, hydrophobic poloxamer species can have undesirable biological effects. The results, thus, indicate that the hydrophobic components contained in the high molecular weight peak of purified (LCM-containing) poloxamer 188 are an unwanted impurity. Thus a poloxamer 188, such as LCMF poloxamer with a reduced amount of these components, is desirable Example 2

Acute Intravenous Infusion of a Poloxamer-188 in Dogs with Advanced Heart Failure The effect of a single dose of LCMF, was evaluated in an experimental model of advanced heart failure in 21 male dogs. In the model, advanced heart failure (HF) defined as a stable (for at least 2 weeks) left ventricular ejection fraction (EF) of ≤30% was produced by multiple sequential intracoronary microembolizations in purpose-bred, mongrel dogs age 1-2 years and weighing between 20.6 and 30.7 kg (Marshall Farms, North Rose, N.Y. 14516) using the methods described in Sabbah et al. ((1991) *Am. J. Physiol.* 260 (Heart Circ. Physiol. 20): H1379-H1384). The model manifests many of the conditions of heart failure observed in humans, including marked and progressive depression of left ventricular (LV) systolic and diastolic function, reduced cardiac output and increased LV filling pressure.

Dogs with HF were randomized to one of three groups (n=7) to assess the effects of either LCMF at 225 mg/kg (Group I, low dose), 450 mg/kg (Group II, high dose) or Normal Saline (NS, 0.9% sodium chloride solution; Group III, control), administered as a single, volume matched, 2 hour, intravenous infusion.

At baseline, 2 hours, 24 hours, 1 week and 2 weeks post-infusion, animals were assessed for hemodynamic parameters, cardiac biomarkers and/or inflammatory biomarkers as described in Examples 3-5. All 21 dogs entered into the study completed the study. None of the dogs developed de-novo ventricular or atrial arrhythmias during infusion of poloxamer product or during the 2 week follow-up period. There were no clinical in-life side effects or adverse events throughout the study period. All studies conformed to the National Institute of Health "Guide and Care for Use of Laboratory Animals" (NIH publication No. 85-23).

Example 3

Evaluation of the Clinical Effects of Acute Intravenous Infusion of a Poloxamer-188 on Left Ventricular Function in Dogs with Advanced Heart Failure Dogs treated as described in Example 2 were evaluated for left ventricular (LV) systolic and diastolic cardiac function and other heart functions to assess the effect of a single infusion of low dose and high dose of the poloxamer product for treating advanced heart failure.

A. Clinical Assessment

To assess heart function, hemodynamic, ventriculographic, echocardiographic, and electrocardiographic measurements were made at baseline prior to drug administration, and at the end of 2 hours of drug infusion. Measurements also were repeated 24 hours, 48 hours, 1 week and 2 weeks after completion of the 2 hours of drug infusion. All measurements were performed under general anesthesia and sterile conditions and all dogs fasted for 12 hours prior to cardiac catheterization. Induction of anesthesia was initiated with IV hydromorphone (0.22 mg/kg) and diazepam (0.17 mg/kg) and plane of anesthesia was maintained with 1-1.5% isofluorane.

i. Hemodynamic and Ventriculographic Measurements

All hemodynamic measurements were made during left and right heart catheterizations in anesthetized dogs at each specified study time point. The following parameters were evaluated in all dogs: 1) aortic and LV pressures using catheter tip micromanometers (Millar Instruments), 2) peak rate of change of LV pressure during isovolumic contraction (peak+dP/dt) and relaxation (peak−dP/dt), 3) LV end-diastolic pressure, and 4) cardiac output (CO) using standard methods (Sabbah et al. (1991) *Am. J. Physiol.* 260 (Heart Circ. Physiol. 20): H1379-H1384; Zaca et al. (2007) *J. Am. Coll. Cardiol.*, 50:551-557). In addition, the following parameters were calculated: 1) LV stroke volume (SV) and 2) systemic vascular resistance (SVR).

Left ventriculograms were performed during cardiac catheterization after completion of the hemodynamic measurements. Ventriculograms were performed with the dog placed on its right side and were recorded on digital media at 30 frames/sec during a power injection of 20 mL of contrast material (ISOVUE-300, Bracco Diagnostics, Inc., Princeton, N.J.). Correction for image magnification was made using radiopaque markers placed on the distal end of the LV ventriculographic catheter. LV end-systolic (ESV) and end-diastolic (EDV) volumes were calculated from angiographic silhouettes using the area length method (Dodge et al. (1966) The American Journal of Cardiology, 18:10-24). Premature beats and postextrasystolic beats were excluded from the analysis. LV ejection fraction (EF) was calculated as the ratio of the difference of end-diastolic and end-systolic volumes to end-diastolic volume times 100.

ii. Echocardiographic and Doppler Measurements

Echocardiographic and Doppler studies were performed in all dogs at all specified study time points using a VIVID 7 ultrasound system (General Electric) with a 3.5 MHz transducer. All echocardiographic measurements were made with the dog placed on its right side and recorded on digital media for subsequent off-line analysis. LV fractional area of shortening (FAS), a measure of LV systolic function, was measured from a short axis view at the level of the papillary muscles. LV thickness of the posterior wall and interventricular septum were measured, summed, and divided by 2 to obtain average LV wall thickness (h), used for calculation of wall stress. LV major and minor semiaxes were measured and used for calculation of LV end-diastolic circumferential wall stress (EDWS; Sabbah et al. (2007) The American Journal of Cardiology, 99:41A-46A)). Wall stress was calculated as follows:

$$\text{Stress} = Pb/h(1-h/2b)(1-hb/2a^2),$$

where P is LV end-diastolic pressure, a is LV major semi-axis, b is LV minor semiaxis, and h is LV wall thickness.

Mitral inflow velocity was measured by pulsed-wave Doppler echocardiography to indexes of LV diastolic function. The velocity waveforms were used to calculate 1) peak mitral flow velocity in early diastole (PE), 2) peak mitral inflow velocity during left atrial (LA) contraction (PA), 3) ratio of PE to PA, 4) time-velocity integral of the mitral inflow velocity waveform representing early filling (Ei), 5) time-velocity integral representing LA contraction (Ai), 6) ratio of Ei/Ai, and 7) deceleration time (DCT) of early mitral inflow velocity using standard methods (Sabbah et al. (2007) Am. J. Cardiol., 99:41A-46A).

iii. Electrocardiographic Measurements

Lead-II of the electrocardiogram was monitored throughout the study and recorded at all specified study time points. If de-novo ventricular arrhythmias were to develop at any time during the study, the electrocardiogram would be recorded continuously. If at any time arrhythmias developed and were associated with hemodynamic compromise, drug infusion would be stopped and the study terminated for that day.

B. Data Analysis

To determine whether differences in hemodynamic, angiographic, echocardiographic, and Doppler variables between study groups were present, within group (inter-group) comparisons were performed using repeated measures analysis of variance (ANOVA) with alpha set at $p<0.05$. If significance was attained, pairwise comparisons between pre-treatment and 2 hours, 24 hours, 1 week and 2 weeks and between 2 hours and 24 hours, 1 week and 2 weeks were performed using the Student-Newman-Keuls Test with significance set at $p<0.05$.

Treatment effect ($\Delta$), for each measured variable, was calculated as the difference between pre-treatment values and subsequent values obtained at 2 hours, 24 hours, 1 week and 2 weeks. To assess treatment effect, the change ($\Delta$) in each measurement among study groups (intragroup) was assessed using one way ANOVA with alpha set at $p<0.05$. If significance was attained, comparisons between the Group III (control group) and each of the two active treatment groups, Group II (low dose LCMF Poloxamer-188) and Group I (high dose LCMF Poloxamer-188) animals, were made using the Student-Newman-Keuls Test with significance set at $p<0.05$. All data are reported as the mean±standard error of the mean (SEM).

C. Results

1. Intergroup Comparisons

The results of the hemodynamic, ventriculographic, and Doppler-echocardiographic results in each of the treatment groups are shown in Tables 1-3, and summarized below. The Tables set forth measured values for the following assessed variables: systolic and mean aortic pressure (AoP); left ventricular end-diastolic pressure (LV EDP); peak rate of change of LV pressure during isovolumic contraction (peak+dP/dt) and relaxation (peak−dP/dt); LV end-diastolic volume (LV EDV); LV endsystolic volume (LV ESV); LV ejection fraction (LV EF); cardiac output (CO); stroke volume (SV); systemic vascular resistance (SVR); fractional area of shortening (FAS); ratio of peak mitral inflow velocity in early diastole (PE) to peak mitral inflow velocity during left atrial contraction (PA) (PE/PA); ratio of integral of mitral inflow velocity in early diastole (Ei) to integral of mitral inflow velocity during left atrial contraction (Ai) (Ei/Ai); deceleration time of early mitral inflow velocity (DCT); end-diastolic circumferential wall stress (EDWS). The results are depicted as the mean value±standard error of the mean (SEM).

a. Findings in Control Dogs (Group III, Normal Saline)

Hemodynamic, ventriculographic, and Doppler-echocardiographic results in control dogs are shown in Table 1. There were no significant changes in heart rate, systolic aortic pressure, mean aortic pressure or LV end-diastolic pressure. Systolic and mean aortic pressures tended to increase at 1 week, but the increase did not reach statistical significance. Peak LV+dP/dt and LV−dP/dt increased at 1 week. This increase was most likely driven by an increase in aortic blood pressure also seen at 1 week. Treatment with NS had no significant effects on CO, SV, FAS, SVR or any of the indexes of LV diastolic function, namely PE/PA, Ei/Ai, DCT, and LV EDWS.

In this group, EDV tended to increase but the change did not reach statistical significance. LV ESV also tended to increase during the course of 2 weeks. The increase reached statistical significant at the 24-hours, 1-week and 2-week time points compared to pre-treatment (Table 1).

TABLE 1

Hemodynamic, Ventriculographic, and Doppler-Echocardiographic Results in Control Dogs (n = 7)

| | PRE-Treatment | 2 Hours | 24 Hours | 1 Week | 2 Weeks |
|---|---|---|---|---|---|
| Heart Rate (beats/min) | 82 ± 2.4 | 82 ± 1.7 | 83 ± 2.1 | 81 ± 2.0 | 82 ± 2.7 |
| Systolic AoP (mmHg) | 93 ± 2.5 | 97 ± 2.3 | 93 ± 1.7 | 100 ± 3.9 | 93 ± 2.6 |
| Mean AoP (mmHg) | 79 ± 2.5 | 83 ± 1.8 | 78 ± 1.3 | 84 ± 4.4 | 78 ± 3.4 |
| LV EDP (mmHg) | 14.4 ± 0.8 | 15.3 ± 1.0 | 15.1 ± 0.6† | 13.3 ± 0.5 | 13.6 ± 0.5 |
| Peak LV + dP/dt (mmHg/sec) | 1264 ± 76 | 1481 ± 137 | 1353 ± 82 | 1629 ± 176* | 1396 ± 58 |
| Peak LV − dP/dt (mmHg/sec) | 1184 ± 61 | 1217 ± 69 | 1253 ± 48 | 1404 ± 97*† | 1280 ± 68 |
| LV EDV (mL) | 70 ± 3.7 | 71 ± 3.5 | 72 ± 3.4 | 73 ± 3.4 | 72 ± 3.4 |
| LV ESV (mL) | 48 ± 2.8 | 48 ± 2.5 | 49 ± 2.5* | 50 ± 2.5* | 50 ± 2.7*† |
| LV EF (%) | 32 ± 0.6 | 32 ± 0.6 | 32 ± 0.7 | 31 ± 0.6 | 31 ± 0.8 |
| CO (L/min) | 1.86 ± 0.12 | 1.89 ± 0.12 | 1.93 ± 0.11 | 1.87 ± 0.11 | 1.80 ± 0.10 |
| SV (mL) | 23 ± 1.0 | 23 ± 1.1 | 23 ± 1.0 | 23 ± 1.0 | 22 ± 1.0 |
| SVR (dynes-cm-sec-5) | 3507 ± 255 | 3629 ± 299 | 3264 ± 161 | 3693 ± 348 | 3519 ± 257 |
| LV FAS (%) | 28 ± 1.5 | 29 ± 1.5 | 29 ± 1.6 | 29 ± 1.6 | 28 ± 1.5 |
| PE/PA | 1.75 ± 0.07 | 1.67 ± 0.08 | 1.71 ± 0.09 | 1.78 ± 0.10 | 1.70 ± 0.05 |
| Ei/Ai | 4.06 ± 0.56 | 3.67 ± 0.33 | 3.80 ± 0.47 | 3.75 ± 0.35 | 3.58 ± 0.32 |
| DCT (msec) | 76 ± 2 | 77 ± 3 | 76 ± 1 | 77 ± 1 | 77 ± 2 |
| LV EDWS (g/cm$^2$) | 66 ± 7 | 69 ± 6 | 74 ± 6 | 62 ± 5 | 66 ± 4 |

\* = $p < 0.05$ vs. Pre-Treatment
† = $p < 0.05$ vs. 2 hours b. Findings in Dogs Treated with Low Dose LCMF Poloxamer-188 (Group II, 225 mg/kg)

Hemodynamic, ventriculographic, and Doppler-echocardiographic results in dogs infused with Low Dose LCMF poloxamer-188 are shown in Table 2. There were no significant changes in heart rate, LV end-diastolic pressure or SVR at any of the study time points. Systolic and mean aortic pressure tended to increase and reached statistical significance at 1 week post treatment. A similar trend was seen with respect to peak LV+dP/dt and peak LV−dP/dt. Low dose LCMF poloxamer-188 tended to increase CO and SV at all study time points compared to pre-treatment and the increase reached statistical significance at 2 hours, 24 hours and 1 week for SV and at 2 hours and 1 week for CO. FAS increased significantly at all study time points compared to pre-treatment. Indices of LV diastolic function improved modestly for up to 1 week post treatment. The ratio Ei/Ai increased significantly at 2 hours and 24 hours post treatment and DCT increased significantly at 2 hours post treatment.

In this group, EDV decreased at all study time points but the change did not reach statistical significance. Similarly, ESV decreased during the follow-up period. The decrease compared to pre-treatment was significant at 2 hours, 24 hours and 1 week. LV EF increased during the follow-up period reaching statistical significance at 2 hours, 24 hours and 1 week post treatment (Table 2).

TABLE 2

Hemodynamic, Ventriculographic, and Doppler-Echocardiographic Results in Dogs (n = 7) Treated with Low Dose (225 mg/kg) LCMF Poloxamer-188

| | PRE-Treatment | 2 Hours | 24 Hours | 1 Week | 2 Weeks |
|---|---|---|---|---|---|
| Heart Rate (beats/min) | 85 ± 1.5 | 85 ± 1.6 | 83 ± 2.3 | 85 ± 1.8 | 86 ± 1.4 |
| Systolic AoP (mmHg) | 89 ± 0.9 | 94 ± 2.0 | 91 ± 1.3 | 104 ± 5.9* | 100 ± 3.9 |
| Mean AoP (mmHg) | 76 ± 0.9 | 81 ± 1.7 | 77 ± 2.1 | 90 ± 6.2* | 87 ± 3.6 |
| LV EDP (mmHg) | 14 ± 0.9 | 15 ± 0.9 | 15 ± 0.7 | 15 ± 0.7 | 15 ± 0.9 |
| Peak LV + dP/dt (mmHg/sec) | 1140 ± 71 | 1355 ± 67 | 1238 ± 37 | 1547 ± 113* | 1451 ± 94* |
| Peak LV − dP/dt (mmHg/sec) | 1148 ± 71 | 1187 ± 40 | 1166 ± 29 | 1344 ± 113 | 1377 ± 120 |
| LV EDV (mL) | 70 ± 2.1 | 66 ± 1.8 | 68 ± 1.6 | 69 ± 2.0 | 68 ± 2.3 |
| LV ESV (mL) | 48 ± 2.0 | 39 ± 1.5* | 42 ± 2.1* | 42 ± 1.9* | 44 ± 1.8† |
| LV EF (%) | 31 ± 1.4 | 41 ± 1.4* | 38 ± 1.9* | 40 ± 1.9* | 35 ± 1.5† |
| CO (L/min) | 1.84 ± 0.09 | 2.27 ± 0.07* | 2.14 ± 0.11 | 2.37 ± 0.11* | 2.06 ± 0.12 |
| SV (mL) | 22 ± 0.9 | 27 ± 1.1* | 26 ± 1.0* | 28 ± 1.5* | 24 ± 1.4 |
| SVR (dynes-cm-sec-5) | 3352 ± 176 | 2870 ± 93 | 2927 ± 194 | 3109 ± 287 | 3479 ± 266 |
| LV FAS (%) | 29 ± 1.6 | 35 ± 1.4* | 35 ± 1.9* | 36 ± 2.2* | 35 ± 2.9* |
| PE/PA | 1.68 ± 0.19 | 1.97 ± 0.15 | 1.88 ± 0.07 | 1.70 ± 0.13 | 1.71 ± 0.07 |
| Ei/Ai | 3.53 ± 0.32 | 4.69 ± 0.38* | 4.40 ± 0.34* | 4.21 ± 0.34 | 3.85 ± 0.34† |
| DCT (msec) | 77 ± 3 | 84 ± 2* | 83 ± 4 | 82 ± 3 | 78 ± 3 |
| LV EDWS (g/cm2) | 61 ± 7 | 65 ± 8 | 70 ± 8 | 66 ± 6 | 67 ± 7 |

\* = $p < 0.05$ vs. Pre-Treatment
† = $p < 0.05$ vs. 2 hours c. Findings in Dogs Treated with High Dose LCMF Poloxamer-188 (Group I, 450 mg/kg)

Hemodynamic, ventriculographic, and Doppler-echocardiographic results in dogs infused with High Dose LCMF poloxamer-188 are shown in Table 3. There were no significant changes in heart rate, LV end-diastolic pressure or SVR at any of the study time points. Systolic and mean aortic pressure increased after pre-treatment and reached statistical significance at 1 week post treatment. A similar trend was seen with respect to peak LV+dP/dt and peak LV−dP/dt. High Dose LCMF poloxamer-188 increased CO and SV at all study time points compared to pre-treatment and the increase reached statistical significance at 2 hours and 1 week for SV, and at 1 week for CO. FAS increased significantly at all study time points compared to pre-treatment with the exception of 2 weeks. Indexes of LV diastolic function improved modestly for up to 1 week post treatment. The ratio Ei/Ai increased significantly at 2 hours post treatment and DCT increased significantly at 2 hours, 24 hours and 1 week post treatment.

In this group, EDV tended to decrease at all study time points and reached significance at 24 hours post treatment. Similarly, ESV tended to decrease during the follow-up period. The decrease compared to pre-treatment was significant at 2 hours, 24 hours and 1 week. LV EF increased during the follow-up period reaching significance at 2 hours, 24 hours and 1 week post treatment (Table 3).

4. The Table sets forth the difference in the assessed parameter between baseline and 2 hours (Δ 2 hrs Post), baseline and 24 hours (Δ 24 hrs Post), baseline and 1 week (Δ 1 Wk Post) and baseline and 2 weeks (Δ 2 Wks Post). The results show that treatment with low and high dose of the LCMF poloxamer-188 improved LV systolic and diastolic functions compared to the control group treated with normal saline.

For example, compared to the Control group, low dose LCMF poloxamer-188 increased Ei/Ai and DCT at 2 hours with improvements lasting for at least 1 week post drug administration. Low dose LCMF poloxamer-188 tended to decrease EDV but the changes were not significant. In contrast, ESV decreased significantly at 2 hours and the significant decrease persisted for 2 weeks. EF, FAS, SV and CO all increased significantly at 2 hours and remained elevated for at least 1 week post drug administration. Low Dose LCMF poloxamer-188 had no effect on heart rate, aortic pressure, LV end diastolic pressure, LV+dP/dt and LV−dP/dt, and end-diastolic wall stress at all time points compared to the control group.

High dose LCMF poloxamer-188 increased Ei/Ai and DCT significantly at 2 hours and 24 hours, with improvements lasting for at least 1 week post drug administration. High dose LCMF poloxamer-188 tended to decrease EDV but the changes were not significant compared to control. In contrast, ESV decreased significantly at 2 hours and the significant decrease persisted for 2 weeks. EF, FAS, SV and CO all increased significantly at 2 hours and remained elevated for at least 1 week post drug administration. Like low dose LCMF poloxamer-188, high dose LCMF polox-

TABLE 3

Hemodynamic, Ventriculographic, and Doppler-Echocardiographic Results in Dogs (n = 7) Treated with High Dose (450 mg/kg) LCMF Poloxamer-188

|  | PRE-Treatment | 2 Hours | 24 Hours | 1 Week | 2 Weeks |
| --- | --- | --- | --- | --- | --- |
| Heart Rate (beats/min) | 85 ± 1.8 | 82 ± 1.5 | 86 ± 2.0 | 88 ± 1.6 | 87 ± 1.2 |
| Systolic AoP (mmHg) | 90 ± 1.1 | 99 ± 4.5 | 95 ± 3.6 | 105 ± 4.3* | 100 ± 3.9 |
| Mean AoP (mmHg) | 78 ± 0.4 | 85 ± 4.6 | 82 ± 3.8 | 91 ± 4.3* | 88 ± 3.5 |
| LV EDP (mmHg) | 15 ± 0.5 | 14 ± 0.5 | 14 ± 0.3 | 14 ± 0.5 | 13 ± 0.5 |
| Peak LV + dP/dt (mmHg/sec) | 1272 ± 104 | 1514 ± 122 | 1355 ± 117 | 1699 ± 149* | 1572 ± 121 |
| Peak LV − dP/dt (mmHg/sec) | 1162 ± 68 | 1256 ± 86 | 1191 ± 58 | 1413 ± 68* | 1354 ± 73 |
| LV EDV (mL) | 74 ± 3.6 | 70 ± 3.4 | 70 ± 3.4* | 73 ± 3.9 | 74 ± 3.9 |
| LV ESV (mL) | 50 ± 2.6 | 41 ± 2.3* | 42 ± 2.3* | 43 ± 3.0* | 47 ± 2.81 |
| LV EF (%) | 32 ± 0.5 | 42 ± 1.6* | 40 ± 1.9* | 40 ± 2.3* | 36 ± 2.4† |
| CO (L/min) | 1.99 ± 0.9 | 2.45 ± 0.11 | 2.37 ± 0.18 | 2.56 ± 0.21* | 2.30 ± 0.23 |
| SV (mL) | 23 ± 1.1 | 30 ± 1.7* | 28 ± 2.1 | 29 ± 2.4* | 27 ± 2.6 |
| SVR (dynes-cm-sec-5) | 3158 ± 140 | 2815 ± 160 | 2851 ± 206 | 2932 ± 217 | 3204 ± 295 |
| LV FAS (%) | 31 ± 1.5 | 40 ± 2.1* | 37 ± 1.5* | 35 ± 2.0* | 34 ± 2.3† |
| PE/PA | 1.67 ± 0.09 | 1.97 ± 0.10 | 1.79 ± 0.17 | 1.57 ± 0.08† | 1.72 ± 0.15 |
| Ei/Ai | 3.54 ± 0.22 | 4.56 ± 0.31* | 4.33 ± 0.35 | 3.49 ± 0.28 | 3.73 ± 0.35† |
| DCT (msec) | 73 ± 3 | 81 ± 3* | 80 ± 3* | 76 ± 3* | 75 ± 3† |
| LV EDWS (g/cm2) | 59 ± 3 | 61 ± 5 | 61 ± 5 | 60 ± 5 | 62 ± 4 |

\* = $p < 0.05$ vs. Pre-Treatment
† = $p < 0.05$ vs. 2 hours

2. Intragroup Comparisons

The treatment effect (Δ) for each measured variable at various time points after infusion compared to the pretreatment value for each of the study groups are set forth in Table amer-188 also had no effect on heart rate, aortic pressure, LV end-diastolic pressure, LV+dP/dt and LV−dP/dt, and end-diastolic wall stress at all time points compared to the control group.

TABLE 4

Treatment Effect (Δ) of Control, Low Dose LCMF Poloxamer-188 (225 mg/kg), and High Dose LCMF Poloxamer-188 (450 mg/kg) in Dogs

|  | Δ 2 hrs Post | Δ 24 hrs Post | Δ 1 Wk Post | Δ 2 Wks Post |
|---|---|---|---|---|
| EDV (mL) | | | | |
| Control | 0.1 ± 0.5 | 2 ± 0.7 | 2 ± 0.8 | 1 ± 0.5 |
| Low Dose | −4 ± 1.7 | −1 ± 2.8 | −0.1 ± 1.6 | −1 ± 1.5 |
| High Dose | −3 ± 1.0 | −4 ± 1.2 | −1 ± 0.7 | 0.1 ± 0.8 |
| ESV (mL) | | | | |
| Control | −0.1 ± 0.3 | 1 ± 0.3 | 2 ± 0.5 | 2 ± 0.4 |
| Low Dose | −9 ± 1.2* | −5 ± 2.1* | −6 ± 2.3* | −4 ± 1.7* |
| High Dose | −10 ± 1.4* | −8 ± 1.3* | −7 ± 1.3* | −3 ± 2.1* |
| EF (%) | | | | |
| Control | 0.1 ± 0.4 | 0.1 ± 0.5 | −0.9 ± 0.3 | −1.4 ± 0.5 |
| Low Dose | 10 ± 0.6* | 7 ± 0.8* | 9 ± 2.4* | 4 ± 1.5 |
| High Dose | 11 ± 1.9* | 8 ± 2.0* | 8 ± 2.1* | 4 ± 2.4 |
| SV (mL) | | | | |
| Control | 0.3 ± 0.3 | 0.7 ± 0.6 | 0.3 ± 0.4 | −0.6 ± 0.4 |
| Low Dose | 5 ± 0.7* | 4 ± 0.69 | 6 ± 1.6* | 2 ± 1.1 |
| High Dose | 6 ± 1.4* | 4 ± 1.8 | 6 ± 1.8* | 3 ± 2.0 |
| CO (L/min) | | | | |
| Control | 0.04 ± 0.06 | 0.08 ± 0.06 | 0.01 ± 0.07 | −0.05 ± 0.07 |
| Low Dose | 0.4 ± 0.07* | 0.3 ± 0.12 | 0.5 ± 0.13* | 0.2 ± 0.10 |
| High Dose | 0.5 ± 0.13* | 0.4 ± 0.21 | 0.6 ± 0.18* | 0.3 ± 0.21 |
| HR (beats/min) | | | | |
| Control | 0.4 ± 2.2 | 1.0 ± 1.5 | −0.6 ± 1.6 | 0 ± 3.1 |
| Low Dose | 0.3 ± 1.8 | −1.6 ± 3.2 | 0.7 ± 2.5 | 1.7 ± 1.9 |
| High Dose | −2.7 ± 1.7 | 0.7 ± 2.7 | 2.6 ± 2.0 | 1.7 ± 2.4 |
| Systolic AoP (mmHg) | | | | |
| Control | 4 ± 1.0 | 1 ± 1.6 | 7 ± 2.9 | 0.1 ± 3.1 |
| Low Dose | 5 ± 2.0 | 2 ± 1.4 | 15 ± 5.3 | 11 ± 3.9 |
| High Dose | 9 ± 3.7 | 4 ± 3.3 | 14 ± 3.9 | 9 ± 3.3 |
| Mean AoP (mmHg) | | | | |
| Control | 4 ± 1.8 | −2 ± 1.8 | 4 ± 3.6 | −1 ± 3.2 |
| Low Dose | 5 ± 2.3 | 1 ± 1.9 | 14 ± 6.2 | 12 ± 3.9* |
| High Dose | 8 ± 4.2 | 5 ± 3.6 | 14 ± 4.2 | 10 ± 3.2* |
| LV EDP (mmHg) | | | | |
| Control | 0.9 ± 0.3 | 0.7 ± 0.6 | −1.1 ± 0.6 | 0.9 ± 0.8 |
| Low Dose | 1 ± 0.4 | 0.9 ± 0.3 | 1 ± 0.7 | 1.4 ± 0.6 |
| High Dose | 0.4 ± 0.3 | −0.3 ± 0.7 | −0.4 ± 0.8 | −0.6 ± 0.8 |
| LV Peak + dP/dt (mmHg/sec) | | | | |
| Control | 216 ± 76 | 89 ± 81 | 364 ± 122 | 132 ± 81 |
| Low Dose | 214 ± 53 | 98 ± 59 | 407 ± 130 | 310 ± 124 |
| High Dose | 242 ± 59 | 83 ± 96 | 427 ± 137 | 300 ± 70 |
| LV Peak − dP/dt (mmHg/sec) | | | | |
| Control | 32 ± 28 | 69 ± 50 | 220 ± 60 | 96 ± 67 |
| Low Dose | 40 ± 70 | 18 ± 62 | 196 ± 116 | 229 ± 150 |
| High Dose | 95 ± 42 | 29 ± 70 | 252 ± 70 | 192 ± 78 |
| SVR (dynes-sec-cm$^{-5}$) | | | | |
| Control | 122 ± 103 | −242 ± 144 | 186 ± 182 | 12 ± 130 |
| Low Dose | −483 ± 125* | −426 ± 173 | −244 ± 329 | 126 ± 266 |
| High Dose | −343 ± 211* | −307 ± 276 | −226 ± 238 | 46 ± 245 |
| FAS (%) | | | | |
| Control | 1 ± 0.2 | 0.7 ± 0.3 | 0.6 ± 0.4 | −0.01 ± 0.6 |
| Low Dose | 6.6 ± 1.1* | 6.1 ± 1.1* | 7.8 ± 1.7* | 5.9 ± 1.8* |
| High Dose | 8.7 ± 1.4* | 5.5 ± 1.2* | 4.1 ± 1.9 | 2.5 ± 1.7 |
| Ei/Ai | | | | |
| Control | −0.4 ± 0.3 | −0.3 ± 0.4 | −0.3 ± 0.5 | −0.5 ± 0.3 |
| Low Dose | 1.2 ± 0.2* | 0.9 ± 0.2* | 0.7 ± 0.3 | 0.3 ± 0.4 |
| High Dose | 1.0 ± 0.2* | 0.8 ± 0.2* | 0.5 ± 0.3 | 0.2 ± 0.3 |

TABLE 4-continued

Treatment Effect (Δ) of Control, Low Dose LCMF Poloxamer-188
(225 mg/kg), and High Dose LCMF Poloxamer-188 (450 mg/kg) in Dogs

|  | Δ 2 hrs Post | Δ 24 hrs Post | Δ 1 Wk Post | Δ 2 Wks Post |
|---|---|---|---|---|
| DCT (msec) | | | | |
| Control | 1 ± 0.8 | 0.6 ± 1.7 | 0.7 ± 1.7 | 0.9 ± 1.1 |
| Low Dose | 7.4 ± 1.7* | 6.1 ± 2.5 | 5.3 ± 2.8 | 1.3 ± 2.3 |
| High Dose | 8.3 ± 1.4* | 6.4 ± 0.7 | 2.4 ± 1.5 | 1.9 ± 1.1 |
| EDWS (g/cm$^2$) | | | | |
| Control | 3 ± 2.0 | 8 ± 3.1 | −4 ± 3.0 | −0.4 ± 4 |
| Low Dose | 4 ± 4.6 | 8 ± 4.1 | 4 ± 3.8 | 5 ± 3.7 |
| High Dose | 3 ± 3.0 | 2 ± 3.3 | 1 ± 4.1 | 3 ± 3.6 |

*= $p < 0.05$ vs. Control.

D. Summary

The results show that compared to control treated animals, a single infusion of a low dose or a high dose of LCMF, improves LV systolic and diastolic functions. For example, treatment with low dose or high dose poloxamer-188 resulted in reduced ESV, and increased EF, CO, SV and FAS. The results also show a more moderate effect of treatment on LV diastolic function, for example, as evidenced by increased Ei/Ai and DCT. These improvements on LV systolic and diastolic functions occurred without affecting heart rate or aortic pressure. These changes persisted for at least 1 week and in some instances 2 weeks after the end of infusion. Thus, the results show that intravenous infusion of LCMF elicits improvements in LV systolic and diastolic function that last for at least 1 week after the end of infusion.

Heart rate was essentially unchanged during each of the study time points and, therefore, the improvements in LV function could not be attributed to changes in the chronotropic state. Administration of the single infusion of a poloxamer-188 had minimal or no effects on LV end-diastolic pressure and end-diastolic volume. Therefore, the improvements in LV function could not be attributed to vasodilation, such as alteration in cardiac loading conditions. Furthermore, systemic blood pressure did not fall, but rather increased demonstrating there was an increased LV stroke output in the absence of a change in vascular resistance.

Example 4

Effect of Acute Intravenous Infusion of a Single Infusion of a Poloxamer-188 on Biomarkers of Cardiac and Hemodynamic Stress Plasma obtained from the dogs treated as described in Example 2 was assessed for the biomarkers troponin-I (TnI) and N-terminal pro-brain natriuretic peptide (nt-pro BNP). TnI is an intracellular protein that is released from cardiomyocytes (heart muscle cells) following injury to and/or death of these cells, and thus is a biomarker of cardiomyocyte injury and death. In patients with heart failure, elevated troponin levels have been associated with more severe disease and a worse clinical progression. NT-pro BNP is released from the heart during periods of increased cardiac wall stress, typically as a result of the increased fluid volumes that are common in heart failure. Generally, higher levels of nt-pro BNP correlates to poor prognosis and increased mortality.

A. Methods for Measuring Cardiac Biomarkers

Peripheral venous blood samples were obtained at baseline, at the end of 2 hours of drug infusion and at 24 hours, 1 week and 2 weeks after drug infusion to assess TnI and nt-pro BNP. The blood samples were centrifuged at 3000 rpm for 10 minutes and plasma withdrawn and placed in cryo-storage tubes and stored upright at −70° C. until needed. Plasma samples from 6 normal dogs (same breed, age and weight as study dogs) were also obtained and stored for comparison.

Plasma levels of TnI and nt-pro BNP were determined by an antibody sandwich enzyme-linked immunosorbent assay (ELISA) using commercially available kits for TnI (ALPCO Diagnostics, Salem, N.H.) or for nt-pro BNP (Kamiya Biomedical Company; Cat# KT-23770). Concentrations were determined from standard curves and expressed as ng/mL (TnI) and pg/mL (nt-pro BNP). Data analysis of TnI and nt-pro BNP levels, and determination of statistical significance, was performed as described in Example 3.

B. Results

1. Plasma Troponin-I (TnI) Levels

The pre-treatment levels of plasma TnI were significantly elevated in the dogs with induced advanced heart failure compared to levels found in normal dogs. For example, the concentration of TnI in normal dogs was on average about 0.1-0.2 ng/mL, but was elevated to about 0.4 ng/mL in dogs with induced heart failure.

Thus, at pre-treatment, all dogs with induced heart failure exhibited increased levels of plasma TnI of about 0.4 ng/mL. The results of the treatments with normal saline, low dose or high dose of LCMF on plasma TnI levels are set forth in Table 5. The results show that in control dogs treated with normal saline, the elevated levels of TnI at pre-treatment remained essentially unchanged. In both Groups treated with the single infusion of the low and high dose LCMF, the plasma TnI levels decreased significantly after treatment. In animals treated with the low dose, a significant decrease in plasma TnI levels was observed at 1 week and 2 weeks after treatment compared to pre-treatment. In animals treated with high dose, a significant decrease in plasma TnI levels was observed at 24 hours, 1 week and 2 weeks after treatment compared to pre-treatment.

The treatment effect (Δ), i.e. difference between pre-treatment values and subsequent values obtained at 2 hours, 24 hours, 1 week and 2 weeks, for the treated Groups also is depicted in Table 6. Compared to NS controls, plasma TnI levels were unchanged at 2 hours but tended to decrease at 24 hours and the reduction reached statistical significance at 1 week and 2 weeks for low dose treatment, and at 24 hours, 1 week and 2 weeks after treatment with high dose.

Thus, the results show that a single infusion of a poloxamer-188 resulted in statistically significant and progressive reductions in TnI, at one week and two weeks after administration. Specifically, at two weeks post-administration, compared to baseline values, mean reduction (improvement) in TnI was 46.7% for the low dose group and 48.8% for the high dose group. In contrast, in the control group, TnI increased 7.7%. These results demonstrate that a single infusion of LCMF poloxamer-188 administered over two hours protects myocardial cells with stable, advanced heart failure for at least two weeks as evidenced by reduced levels of TnI.

TABLE 5

Plasma troponin-I (TnI)

TnI (ng/mL)

| | Normal Levels | PRE-Treatment | 2 Hours | 24 Hours | 1 Week | 2 Weeks |
|---|---|---|---|---|---|---|
| Control | 0.11 ± 0.02 | 0.39 ± 0.06 | 0.39 ± 0.05 | 0.41 ± 0.06 | 0.42 ± 0.06 | 0.42 ± 0.05 |
| Low Dose | 0.13 ± 0.02 | 0.45 ± 0.03 | 0.45 ± 0.03 | 0.41 ± 0.03 | 0.35 ± 0.02* | 0.24 ± 0.02* |
| High Dose | 0.14 ± 0.03 | 0.41 ± 0.05 | 0.41 ± 0.05 | 0.34 ± 0.04* | 0.27 ± 0.03* | 0.21 ± 0.03* |

*= $p < 0.05$ vs. Pre-Treatment

TABLE 6

Treatment Effect ($\Delta$) of Control, Low Dose LCMF Poloxamer-188 (225 mg/kg), and High Dose LCMF Poloxamer-188 (450 mg/kg) in Dogs

| TnI (ng/mL) | $\Delta$ 2 hrs Post | $\Delta$ 24 hrs Post | $\Delta$ 1 Wk Post | $\Delta$ 2 Wks Post |
|---|---|---|---|---|
| Control | 0.00 ± 0.0 | 0.02 ± 0.01 | 0.02 ± 0.01 | 0.03 ± 0.01 |
| Low Dose | 0.00 ± 0.0 | −0.04 ± 0.02 | −0.11 ± 0.02* | −0.21 ± 0.03* |
| High Dose | 0.00 ± 0.1 | −0.07 ± 0.03* | −0.14 ± 0.02* | −0.2 ± 0.03* |

*= $p < 0.05$ vs. Control.

2. Plasma Nt-Pro BNP Levels

The pre-treatment levels of plasma nt-pro BNP were significantly elevated in dogs with induced advanced heart failure dogs compared to levels found in normal dogs. For example, the concentration of nt-pro BNP in normal dogs was on average about 300 pg/mL, but was elevated to about 1100-1300 pg/mL in dogs with induced advanced heart failure.

Thus, at pre-treatment, all dogs with induced heart failure exhibited elevated levels of plasma nt-pro BNP of about 1100-1300 pg/mL. The results of the treatments with normal saline, low dose LCMF poloxamer-188 or high dose LCMF poloxamer-188 on plasma nt-pro BNP levels are set forth in Table 7. The results show that in control dogs treated with normal saline, the elevated levels of nt-pro BNP at pre-treatment remained essentially unchanged. In the Groups treated with low and the high dose LCMF poloxamer-188, plasma nt-pro BNP levels decreased significantly after treatment. In animals treated with a low dose, a significant decrease in plasma nt-pro BNP levels was observed at 1 week and 2 weeks after treatment compared to pre-treatment. In animals treated with the high dose, a significant decrease in plasma nt-pro BNP levels was observed at 24 hours, 1 week and 2 weeks after treatment compared to pre-treatment.

The treatment effect ($\Delta$), i.e. difference between pre-treatment values and subsequent values obtained at 2 hours, 24 hours, 1 week and 2 weeks, for the treated Groups also is depicted in Table 8. Compared to controls, plasma nt-pro BNP levels tended to decrease at 2 hours and 24 hours and the reduction reached statistical significance at 2 weeks after treatment with low dose and at 1 week and 2 weeks after treatment with high dose.

Thus, the results show that a single infusion of LCMF poloxamer-188 administered over two hours resulted in a statistically significant and progressive reduction in hemodynamic stress as evidenced by a reduction in plasma nt-pro BNP, with such effect persisting for at least two weeks after administration. Specifically, at two weeks post-administration, compared to baseline values, mean reduction (improvement) in nt-pro BNP was 54.5% for the low dose group and 61.4% for the high dose group. In contrast, in the control group, nt-pro BNP increased 3.5%.

TABLE 7

N-terminal pro-brain natriuretic (nt-pro BNP)

Nt-Pro BNP (pg/mL)

| | Normal Levels | PRE-Treatment | 2 Hours | 24 Hours | 1 Week | 2 Weeks |
|---|---|---|---|---|---|---|
| Control | 348 ± 46 | 1373 ± 262 | 1342 ± 210 | 1349 ± 158 | 1438 ± 181 | 1421 ± 174 |
| Low Dose | 312 ± 52 | 1131 ± 158 | 1116 ± 150 | 1019 ± 146 | 924 ± 124* | 515 ± 58* |
| High Dose | 290 ± 44 | 1223 ± 239 | 1105 ± 193 | 852 ± 104* | 577 ± 58* | 472 ± 60* |

*= $p < 0.05$ vs. Pre-Treatment

TABLE 8

Treatment Effect ($\Delta$) of Control, Low Dose LCMF Poloxamer-188 (225 mg/kg), and High Dose LCMF Poloxamer-188 (450 mg/kg) in Dogs

| Nt-Pro BNP (pg/mL) | $\Delta$ 2 hrs Post | $\Delta$ 24 hrs Post | $\Delta$ 1 Wk Post | $\Delta$ 2 Wks Post |
|---|---|---|---|---|
| Control | 31 ± 57 | −24 ± 144 | 65 ± 393 | 47 ± 148 |
| Low Dose | −15 ± 11 | −112 ± 33 | −207 ± 47 | −616 ± 102* |
| High Dose | −119 ± 52 | −371 ± 140 | −646 ± 211* | −751 ± 223* |

*= $p < 0.05$ vs. Control.

Example 5

Effect of Acute Intravenous Infusion of a Poloxamer-188 on Inflammatory Biomarkers of Heart Failure The dogs treated as described in Example 2 were assessed for plasma levels of various inflammatory biomarkers of heart failure, including matrix metalloproteinase-2 (MMP-2), Interleukin 6 (IL-6), C-reactive protein (CRP) and TNF-alpha (TNFα). Elevated levels of these biomarkers are known to be associated with cardiac risk. For example, increased levels of the proinflammatory cytokine TNFα are associated with myocardial dysfunction and remodeling, IL-6 is an acute phase cytokine that promotes production of other inflammatory mediators and is associated with decreased cardiac functional status, elevated levels of CRP are known to be associated with an increased risk for coronary artery disease and acute coronary syndromes (ACS), and MMP-2 can degrade collagen fibrils and its upregulation results in unstable plaques and is associated with cardiovascular disease progression. In addition, the biomarker Procollagen type I N-terminal propeptide (PINP) also was assessed, which is an indicator of collagen synthesis and remodeling of the myocardium.

A. Methods for Measuring Biomarkers

Peripheral venous blood samples were obtained at baseline, at the end of 2 hours of drug infusion and at 24 hours, 1 week and 2 weeks after drug infusion. The blood samples were centrifuged at 3000 rpm for 10 minutes and plasma withdrawn and placed in cryo-storage tubes and stored upright at −70° C. until assay. Plasma samples from 6 normal dogs (same breed, age and weight as study dogs) were also obtained and stored for comparison.

An antibody sandwich enzyme-linked immunosorbent assay (ELISA) was used to measure each marker using commercially available ELISA kits. Kits for IL-6 were purchased from ALPCO Diagnostics. Protein concentrations were determined from standard curves. The concentration of MMP-2 was expressed as ng/ml, IL-6, PINP and TNFα as pg/mL and CRP as µg/mL. Data analysis, and determination of statistical significance, was performed as described in Example 3.

B. Results

The results show that the pre-treatment plasma levels of all tested biomarkers were elevated in dogs with induced heart failure compared to levels found in normal dogs. Infusion of normal saline into heart failure dogs had no effect on the levels of any of the biomarkers. Treatment with low and high poloxamer-188 reduced plasma levels of TNFα, IL-6, CRP and MMP-2 at 1 week and 2 weeks post-treatment. The results were dose-dependent, with increased reduction in plasma levels occurring in the group of dogs treated with a high dose of poloxamer-188. No effect on plasma levels of PINP was observed after treatment at either tested dose compared to controls. The results show that a single, 2 hour infusion of a poloxamer-188 in dogs with heart failure elicits improvements in biomarkers of inflammation, and to a lesser extent collagen deposition, that persisted for at least 2 weeks post-treatment.

TABLE 6

Treatment Effect of Control, Low Dose LCMF Poloxamer-188 (225 mg/kg), and High Dose LCMF Poloxamer-188 (450 mg/kg) in Dogs

| | TNFα (pg/ml) | | | | | |
|---|---|---|---|---|---|---|
| | Normal | Pre-Treatment | 2 hrs | 24 hrs | 1 Wk | 2 Wk |
| Control | 1.9 ± .05 | 4.11 ± 0.38 | 4.11 ± 0.38 | 4.99 ± .39 | 4.29 ± 0.38 | 4.35 ± 0.37 |
| Low Dose | 1.91 ± .05 | 4.48 ± .10 | 4.37 ± .06 | 4.84 ± .38 | 4.17 ± .19 | 3.74 ± .12 |
| High Dose | 1.89 ± .07 | 4.38 ± 0.37 | 4.40 ± 0.36 | 3.93 ± .21 | 3.30 ± 0.23 | 3.05 ± 0.15* |

| | Normal | Pre | 2 hrs | 24 hrs | 1 Wk | 2 Wk |
|---|---|---|---|---|---|---|
| | IL-6 (pg/ml) | | | | | |
| Control | 8.98 ± 0.70 | 22.56 ± 1.73 | 23.51 ± 1.69 | 36.23 ± 2.16 | 24.66 ± 1.51 | 27.68 ± 1.25 |
| Low Dose | 8.06 ± 1.10 | 24.66 ± 2.50 | 24.41 ± 2.61 | 31.87 ± 3.08 | 22.76 ± 2.23* | 19.91 ± 2.38* |
| High Dose | 7.59 ± 0.49 | 26.76 ± 1.97 | 28.13 ± 4.10 | 27.93 ± 2.98 | 14.04 ± 1.66*† | 12.56 ± 1.30*† |
| | CRP (µg/ml) | | | | | |
| Control | 5.21 ± 0.62 | 21.0 ± 0.70 | 26.0 ± 1.6 | 48.75 ± 1.74 | 22.1 ± 0.6 | 21.3 ± 0.5 |
| Low Dose | 5.39 ± 0.61 | 22.92 ± 0.58 | 21.24 ± 0.61 | 46.65 ± 1.05 | 17.54 ± 0.51* | 14.72 ± 0.48* |
| High Dose | 5.25 ± 0.36 | 22.54 ± 0.75 | 21.47 ± 1.17 | 38.87 ± 2.97*† | 12.84 ± 0.60*† | 7.24 ± 0.40*† |
| | MMP-2 (ng/ml) | | | | | |
| Control | 8.34 ± 0.45 | 13.4 ± 0.67 | 13.56 ± 0.66 | 13.76 ± 0.64 | 14.06 ± 0.67 | 13.63 ± 1.02 |
| Low Dose | 6.97 ± 0.62 | 12.71 ± 0.70 | 12.61 ± 0.69 | 12.45 ± 0.67 | 12.20 ± 0.67* | 11.09 ± 0.48* |
| High Dose | 7.52 ± 0.40 | 12.80 ± 0.57 | 12.53 ± 0.59 | 12.20 ± 0.60 | 10.10 ± 0.40*† | 9.12 ± 0.37*† |
| | PINP (pg/ml) | | | | | |
| Control | 266.67 ± 18.70 | 342.07 ± 46.91 | 342.51 ± 41.89 | 353.40 ± 45.45 | 365.34 ± 50.06 | 366.78 ± 46.89 |
| Low Dose | 273.67 ± 22.02 | 347.89 ± 53.77 | 344.20 ± 47.01 | 355.48 ± 52.58 | 345.98 ± 46.00 | 339.40 ± 42.91 |
| High Dose | 289.52 ± 21.73 | 334.68 ± 35.01 | 337.05 ± 33.86 | 330.64 ± 37.17 | 355.73 ± 46.07 | 323.89 ± 33.20 |

*=p < 0.05 vs. Control.
†= p < 0.05 vs. Low Dose.

Example 6

Figure 11A:
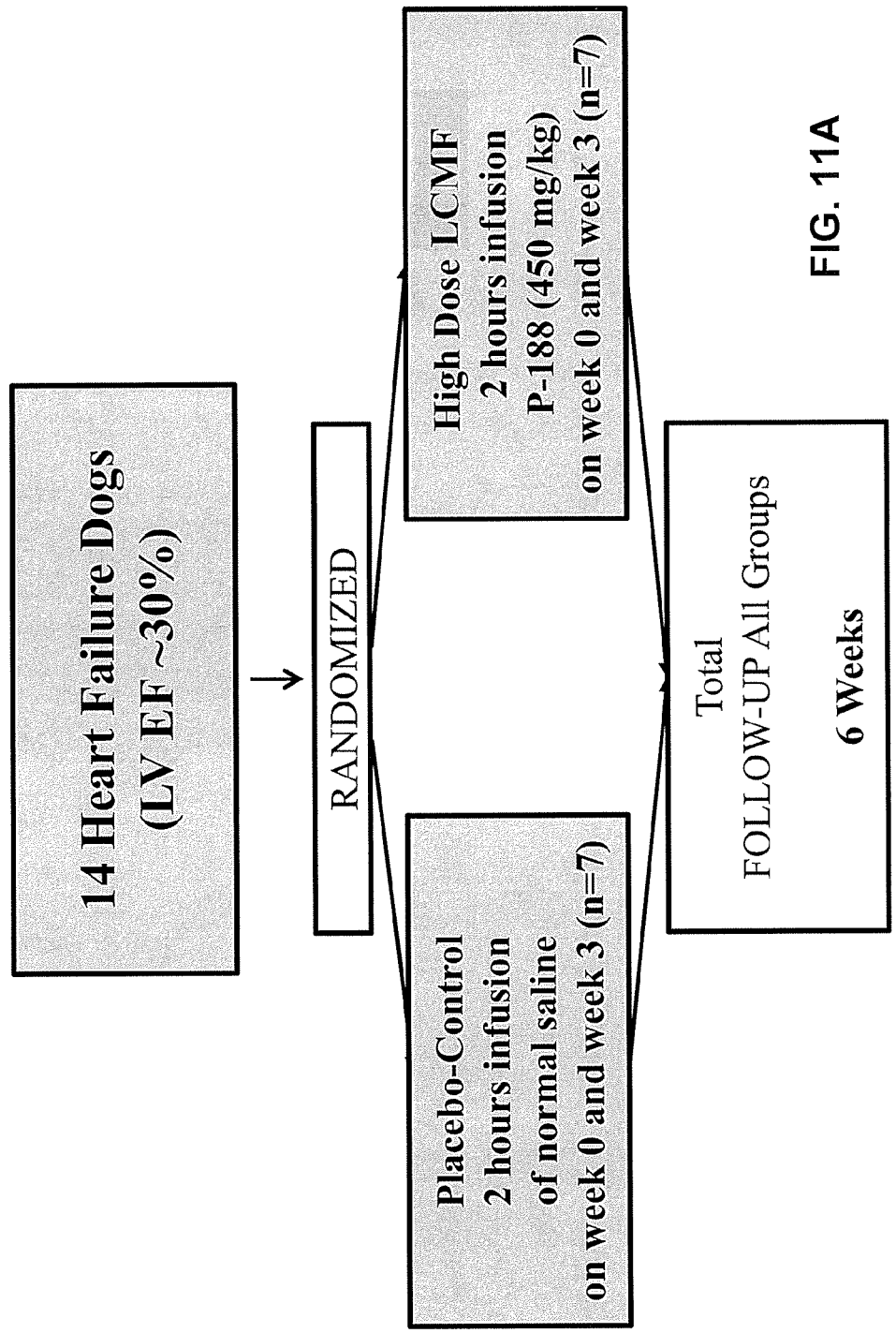

The Effects of Repeat Administration of Purified Poloxamer 188 on Left Ventricular (LV) Systolic and Diastolic Function in Dogs with Advanced Heart Failure The study was performed in 14 dogs with advanced heart failure (HF) produced by multiple sequential intracoronary microembolizations to produce a left ventricular (LV) ejection fraction≤30%. The protocol for the study is depicted in FIGS. 11A and 11B. The P-188 was prepared as described in Example 1.

Following microembolization, dogs with stable ejection fractions of 30% or less were randomized into 2 groups. Group-I (n=7) was treated with an intravenous infusion of P-188 (450 mg/kg administered over a period of 2 hours) followed with complete hemodynamic, ventriculographic, and echocardiographic assessments at 24 hours, 1 week, 2 weeks, and 3 weeks post infusion. Following the 3 week assessment, dogs were treated with a second dose of P-188 (450 mg/kg administered over 2 hours) and again received complete hemodynamic, ventriculographic and echocardiographic assessment at 24 hours, 1 week, 2 weeks and 3 weeks. Dogs randomized to group II served as the control and received identical treatments and assessments except intravenous infusion of normal saline was substituted for the P-188. The volume of saline administered over the course of 2 hours in Group II was identical to the volume of MST-188 administered over 2 hours in Group I.

All hemodynamic, ventriculographic and echocardiographic measurements were performed under general anesthesia and sterile conditions. Induction of anesthesia was initiated with intravenous hydromorphone (0.22 mg/kg) and diazepam (0.17 mg/kg) and plane of anesthesia was maintained with 1-1.5% isofluorane. Studies were initiated once the protocol was approved by Henry Ford Health System Institutional Animal Care and Use Committee. All studies conformed to the National Institute of Health "Guide and Care for Use of Laboratory Animals" (NIH publication No. 85-23).

All hemodynamic measurements were made during left and right heart catheterizations in anesthetized dogs at each specified study time point. The following parameters were evaluated in all dogs: 1) aortic and LV pressures using catheter tip micromanometers (Millar Instruments), 2) peak rate of change of LV pressure during isovolumic contraction (peak+dP/dt) and relaxation (peak−dP/dt), 3) LV end-diastolic pressure, and 4) cardiac output (CO). The following parameters were calculated: 1) LV stroke volume (SV) and 2) systemic vascular resistance (SVR).

Left ventriculograms were performed during cardiac catheterization after completion of the hemodynamic measurements. Ventriculograms were performed with the dog placed on its right side and were recorded on digital media at 30 frames/sec during a power injection of 20 ml of contrast material (ISOVUE-300, Bracco Diagnostics, Inc., Princeton, N.J.). Correction for image magnification was made using radiopaque markers placed on the distal end of the LV ventriculographic catheter. LV end-systolic (ESV) and end-diastolic (EDV) volumes were calculated from angiographic silhouettes using the area length method (2). Premature beats and postextrasystolic beats were excluded from the analysis. LV ejection fraction (EF) was calculated as the ratio of the difference of end-diastolic and end-systolic volumes to end-diastolic volume times 100.

Echocardiographic and Doppler studies were performed in all dogs at all specified study time points using a VIVID 7 ultrasound system (General Electric) with a 3.5 MHZ transducer. All echocardiographic measurements were made with the dog placed on its right side and recorded on a digital media for subsequent off-line analysis. LV fractional area of shortening (FAS), a measure of LV systolic function, was measured from a short axis view at the level of the papillary muscles. LV major and minor semiaxes were measured and used for calculation of LV end-diastolic circumferential wall stress (EDWS) (3). Wall stress will be calculated as follows: Stress=Pb/h(1−h/2b)(1−hb/2a$^2$), where P is LV end-diastolic pressure, a is LV major semiaxis, b is LV minor semiaxis, and h is LV wall thickness.

Mitral inflow velocity was measured by pulsed-wave Doppler echocardiography to indexes of LV diastolic function. The velocity waveforms were used to calculate 1) peak mitral flow velocity in early diastole (PE), peak mitral inflow velocity during LA contraction (PA), 3) ratio of PE to PA, 4) time-velocity integral of the mitral inflow velocity waveform representing early filling (Ai), 5) time-velocity integral representing LA contraction (Ai), 6) ratio of Ei/Ai, and 7) deceleration time (DCT) of early mitral inflow velocity.

Figure 12A:
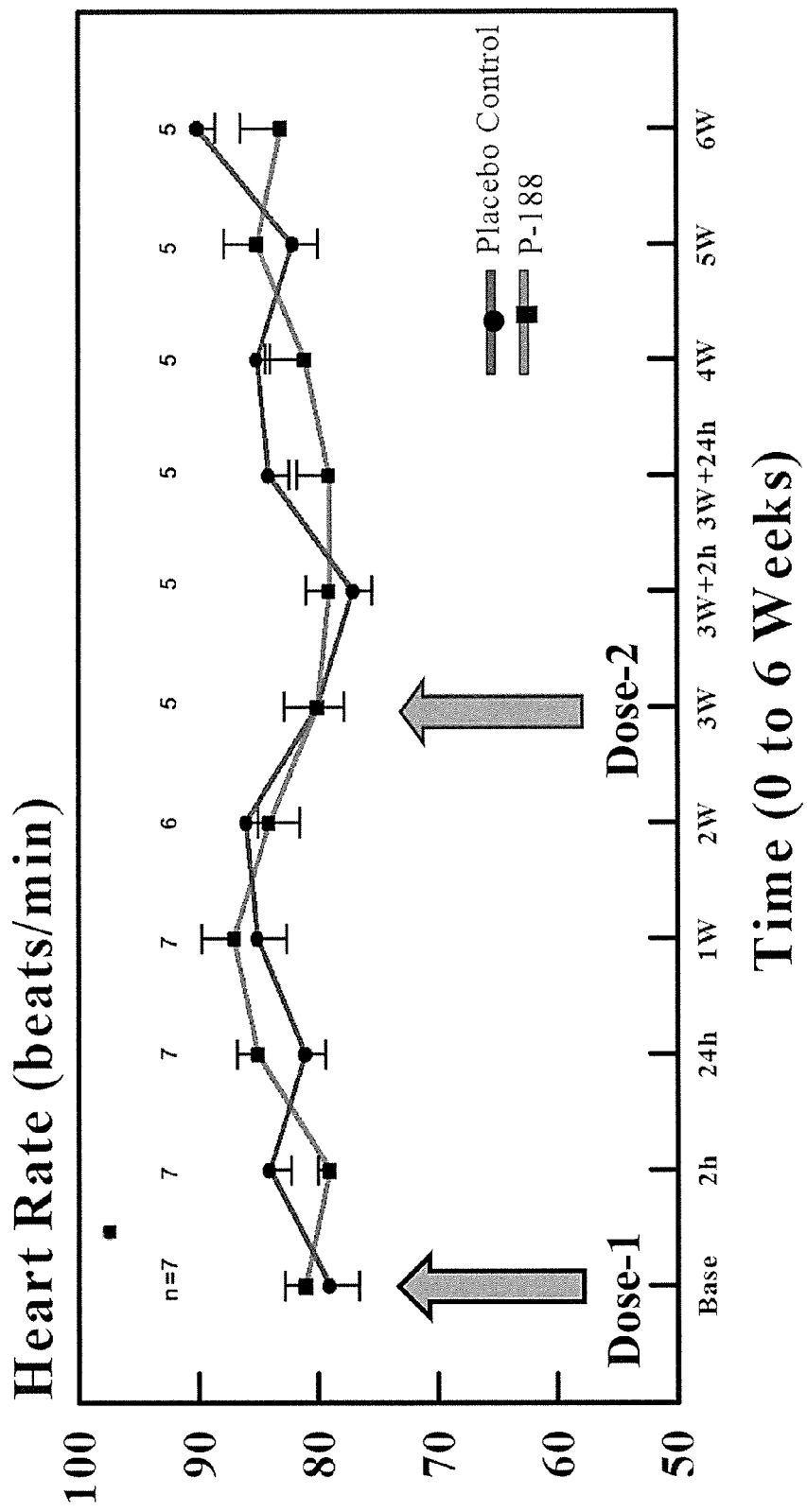
Figure 12B:
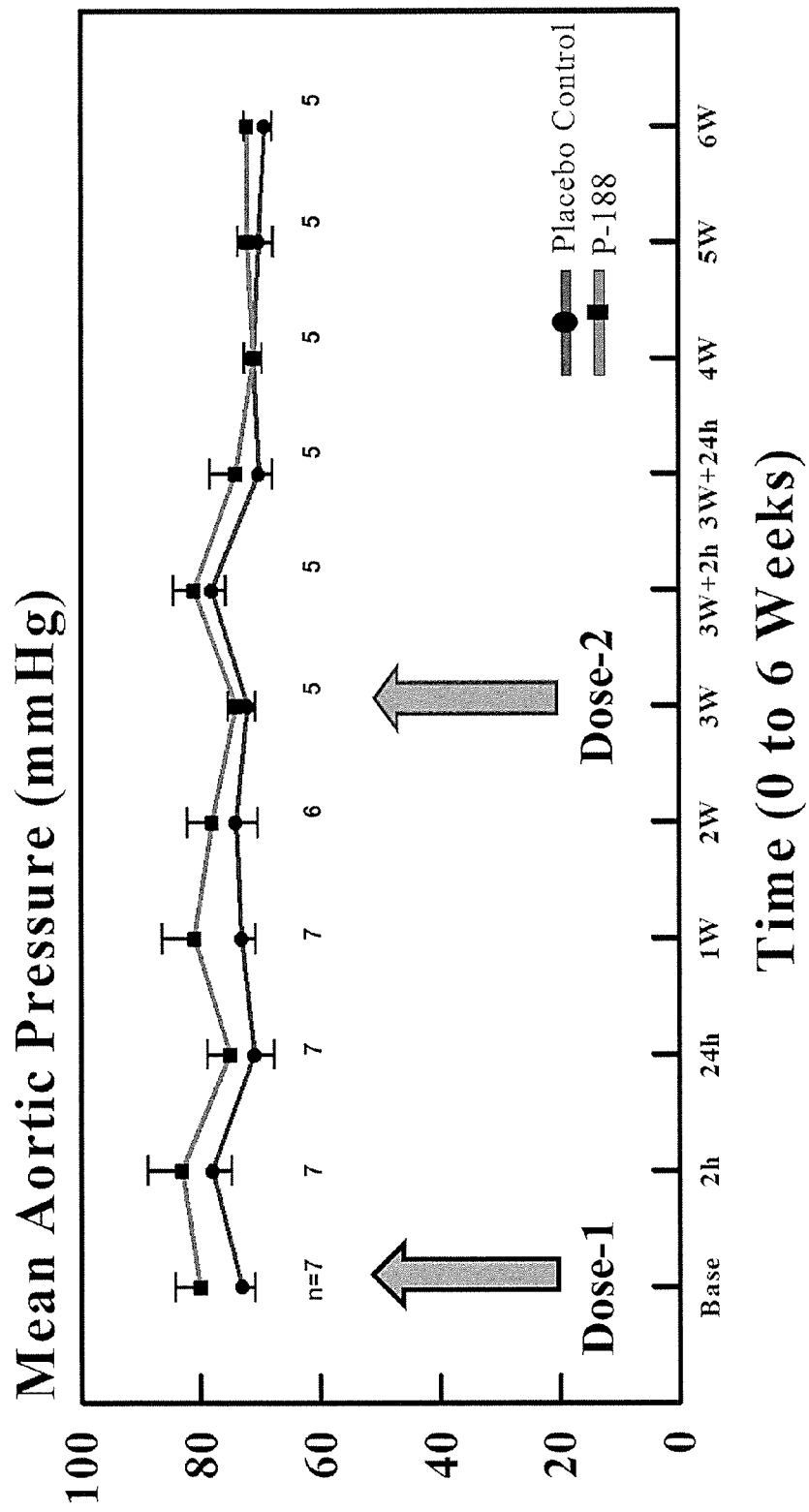
Figure 12C:
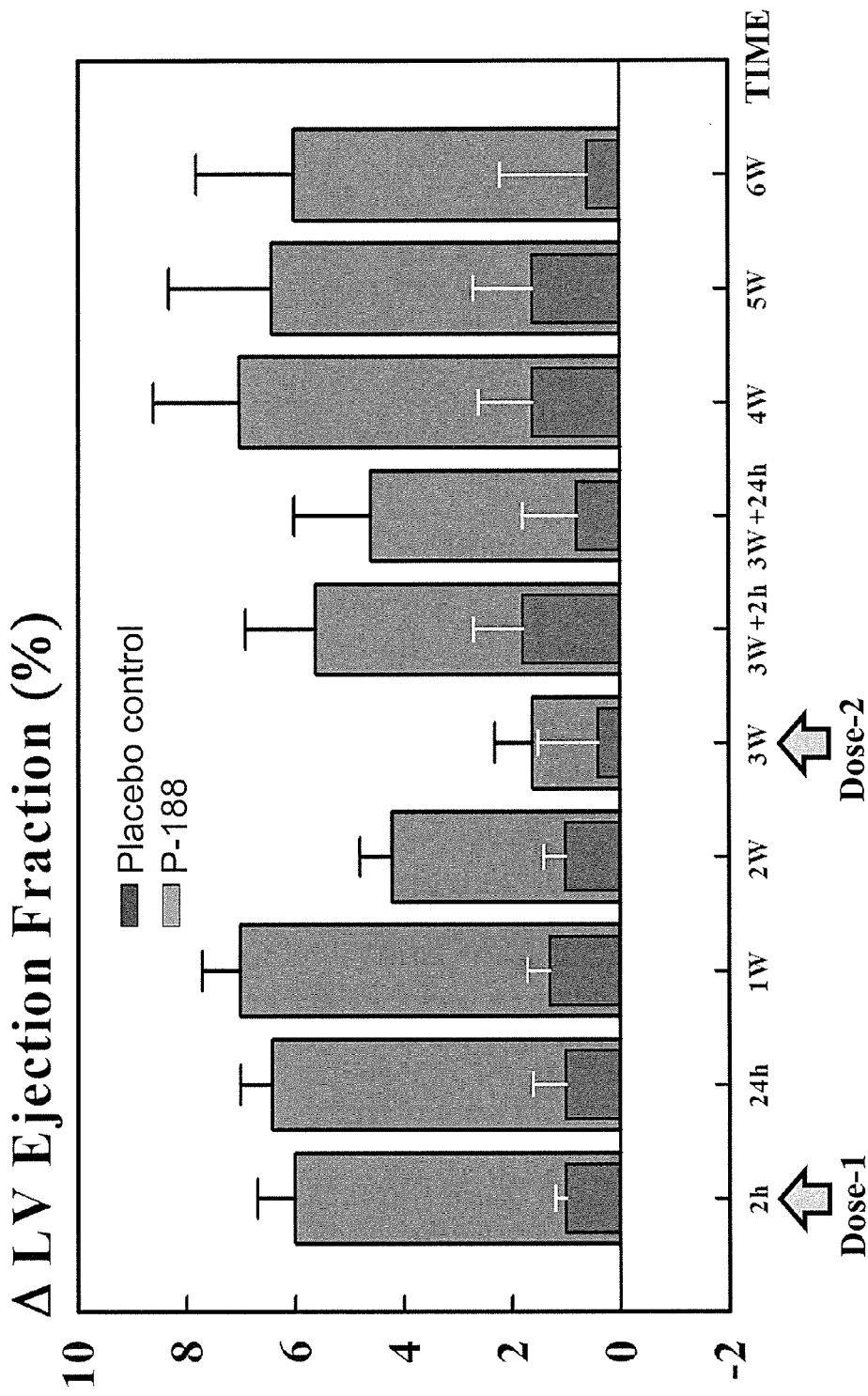
Figure 12D:
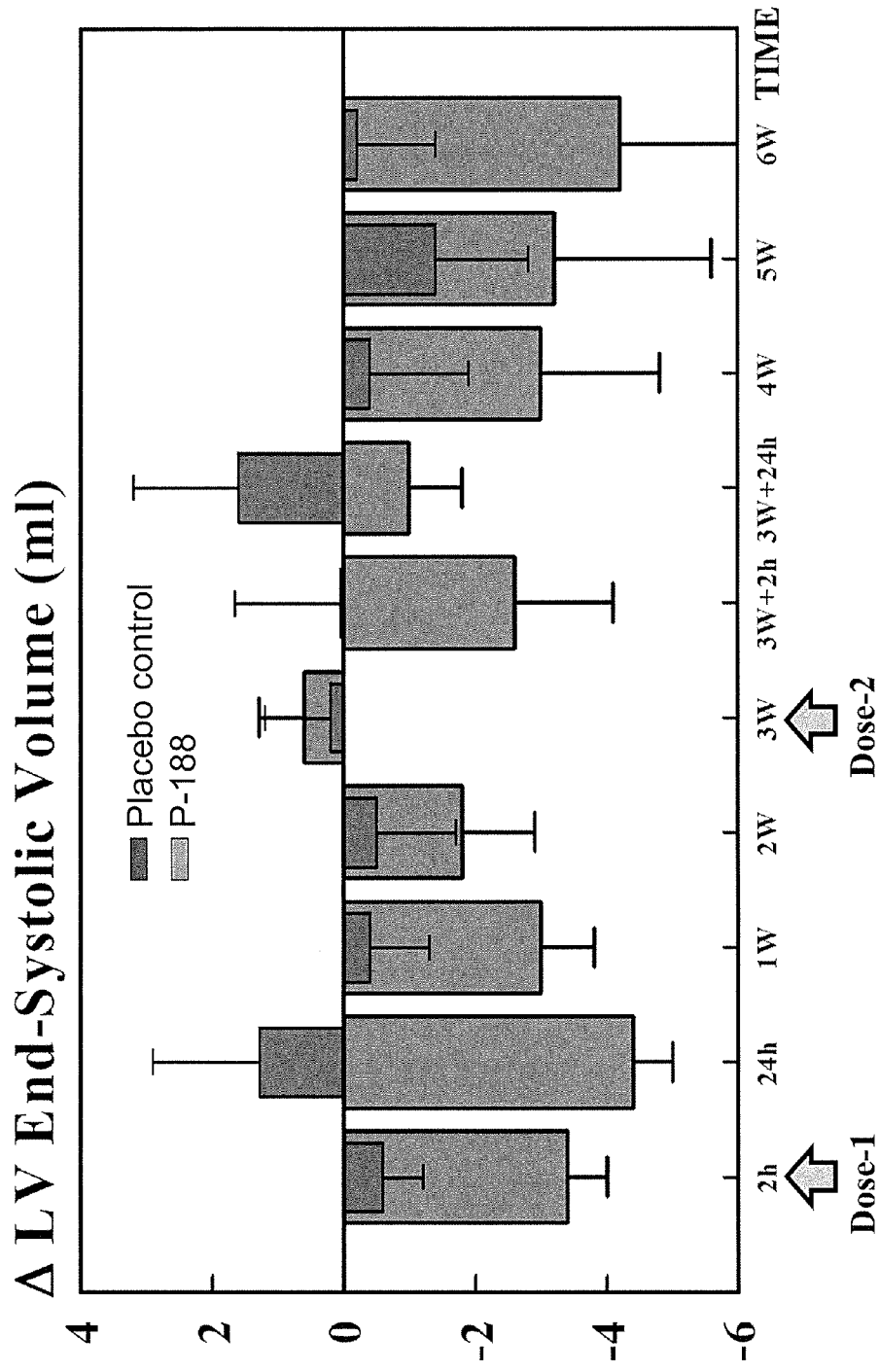
Figure 12E:
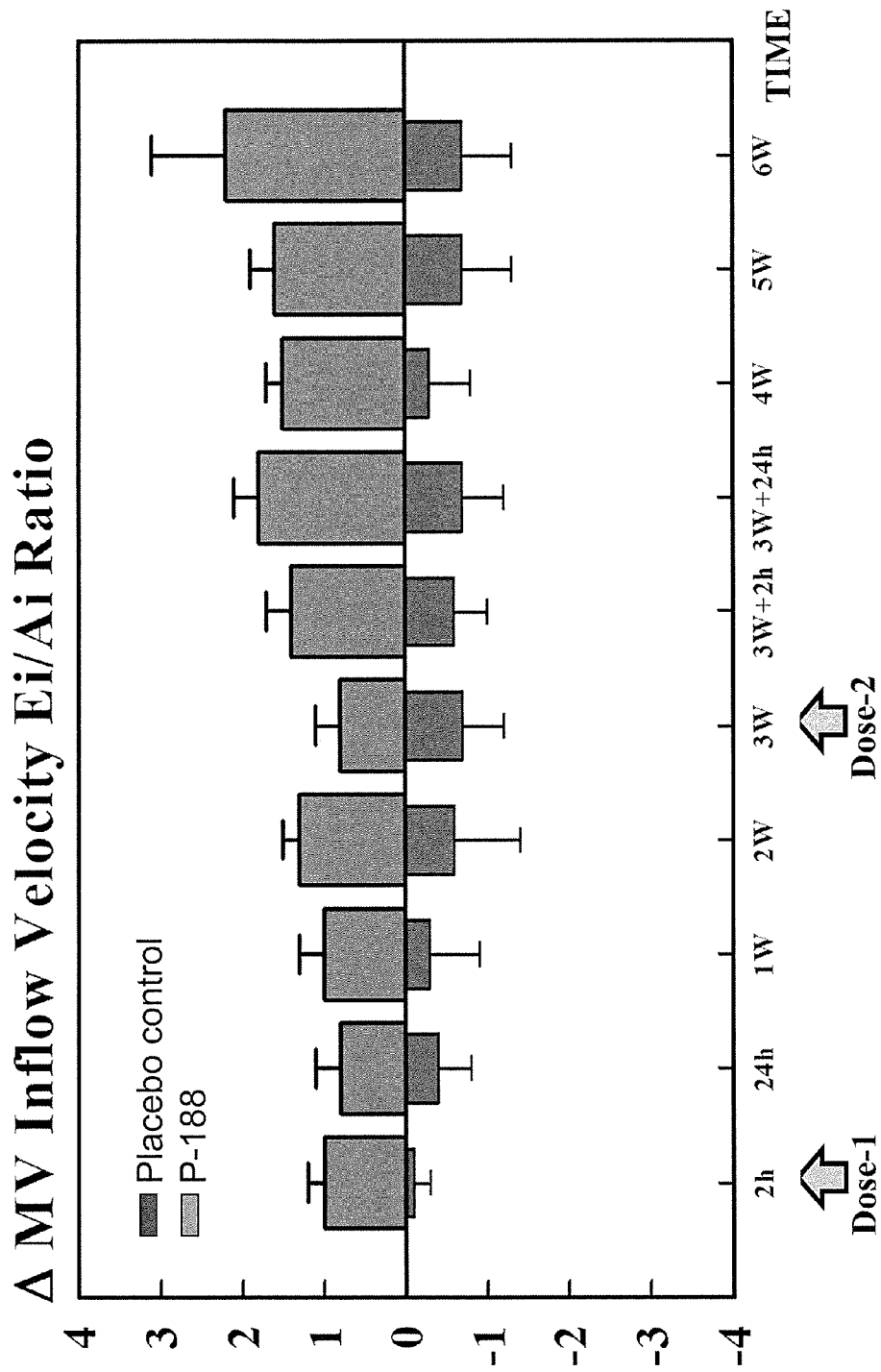

The results are shown in FIGS. 12A-12F. FIGS. 12A and 12B show the results for heart rate and blood pressure (mean aortic pressure), respectively. There were no significant changes in either parameter for control or P-188 treated dogs. FIGS. 12C and 12D show systolic ventricular function as measured by the absolute change in left ventricular ejection fraction and end systolic volume, respectively. For both parameters no change was observed following either the first or second administration in dogs treated with saline. In marked contrast, ejection fraction and end systolic volume markedly improved by the end of the two hour infusion and remained improved for at least two weeks in P-188 treated dogs. By three weeks, values were returning or had returned to baseline values. Following a second infusion with P-188, both parameters again improved and remained improved for three weeks (end of the study). FIGS. 12E and 12F show ventricular diastolic function as measured by the absolute change in Ei/Ai ratio and deceleration time (DT) respectively. For both parameters no change was observed following either the first or second administration in dogs treated with saline. The Ei/Ai ratio and DT improved following a single administration in dogs treated with P-188. Following the second administration, improvements in greater magnitude were observed for both parameters.

A single administration of intravenous P-188, elicits improvements in LV systolic and diastolic function that are sustained for up to 3 weeks. Following a second administration of P-188, (at 3 weeks post first treatment) improvements of greater magnitude and longer duration occur. When a dose of P-188 of 450 mg/kg is administered, and then the same dose is re-administered at 3 weeks, the improvement seems to build upon what was observed from the first administration. In particular, there is an improved durability of the effect, and also, for some measurements, the magnitude. The improved durability indicates that over time treatment can be effected with either lower doses and/or less frequent intervals.

Since modifications will be apparent to those of skill in this art, it is intended that this invention be limited only by the scope of the appended claims.

What is claimed is:

1. A method of treating heart failure, comprising:
    a) administering to the subject in need thereof, a composition comprising an amount of a of a long circulating material free (LCMF) poloxamer 188 wherein:
    the LCMF poloxamer 188 is a polyoxyethylene/polyoxypropylene copolymer having the chemical formula: $HO(C_2H_4O)_{a'}\text{—}(C_3H_6O)_b\text{—}(C_2H_4O)_aH$, wherein:
    the copolymer preparation has been purified to remove low molecular weight impurities;
    a' and a are the same or different and each is an integer, whereby the hydrophile portion represented by $(C_2H_4O)$ constitutes approximately 60% to 90% or 60%-90% by weight of the compound;
    b is an integer, whereby the hydrophobe represented by $(C_3H_6O)$ has a molecular weight of about 1,200 Da to about 2,300 Da or 1,200 to 2,300 Da;
    no more than 1.5% of the total components in the distribution of the co-polymer are low molecular weight components having an average molecular weight of less than 4,500 Daltons;
    no more than 1.5% of the total components in the distribution of the co-polymer are high molecular weight components having an average molecular weight of greater than 13,000 Daltons; and
    the copolymer is administered as a single infusion of at least 100 mg/kg weight of the subject; and
    b) after one week or at least one week, repeating the administration at least one more time, wherein a second infusion and a subsequent infusion of the polyoxyethylene/polyoxypropylene copolymer is administered 2 to 4 weeks following the prior infusion.

2. The method of claim 1, wherein the single infusion is administered in 2 to 6 hours or in less than 24 hours.

3. The method of claim 1, wherein a second infusion and any subsequent infusion of the polyoxyethylene/polyoxypropylene copolymer is administered 2 to 3 weeks following the prior infusion.

4. The method of claim 1, wherein the second infusion and any subsequent infusion is administered at 3-4 week intervals following the prior infusion.

5. The method claim 1, further comprising additional infusions, wherein the interval between infusions is increased for each infusion.

6. The method of claim 5, wherein the interval is increased by at least 1 week, whereby a third infusion is administered at 4-5, 5-6 or 4-6 weeks after the second infusion.

7. The method of claim 6, wherein the dosage is decreased with each infusion.

8. The method of claim 1, wherein performance of the heart is monitored between infusions.

9. The method of claim 8, wherein the dose is decreased as the performance of the heart improves.

10. The method of claim 1, wherein the first dosage of the copolymer is between about 100 mg/kg and about 675 mg/kg.

11. The method of claim 1, wherein the heart failure is manifested by the presence of one or more of arrhythmias, elevated blood pressure, narrowing arteries, catheterization or altered cardiac output.

12. The method of claim 1, wherein the heart failure is systolic heart failure.

13. The method of claim 1, wherein the heart failure is diastolic heart failure.

14. The method of claim 1, wherein:
    the polyoxyethylene/polyoxypropylene copolymer is a poloxamer with a hydrophobe having a molecular weight of about 1,400 to 2,000 Da or 1,400 Da to 2,000 Da, and a hydrophile portion constituting approximately 70% to 90% or 70% to 90% by weight of the copolymer;
    the polyoxyethylene/polyoxypropylene copolymer has a polydispersity value of less than approximately 1.07 or less than 1.07;
    no more than 1.5% of the total components in the distribution of the co-polymer are low molecular weight components having an average molecular weight of less than 4,500 Daltons; and
    no more than 1.5% of the total components in the distribution of the co-polymer are high molecular weight components having an average molecular weight of greater than 13,000 Daltons.

15. The method of claim 1, wherein:
    the average molecular weight of the polyoxyethylene/polyoxypropylene copolymer is approximately 8,400-8,800 Da; and
    the polyoxyethylene/polyoxypropylene copolymer comprises poloxamer 188.

16. The method of claim 1, wherein:
    the LCMF poloxamer 188 is a polyoxyethylene/polyoxypropylene copolymer that has the formula $HO(CH_2CH_2O)_{a'}\text{—}[CH(CH_3)CH_2O]_b\text{—}(CH_2CH_2O)_aH$;
    each of a and a' is an integer such that the percentage of the hydrophile $(C_2H_4O)$ is between approximately 60% and 90% by weight of the total molecular weight of the copolymer;
    a and a' are the same or different;
    b is an integer such that the molecular weight of the hydrophobe $(C_3H_6O)$ is between approximately 1,300 Daltons and 2,300 Daltons;
    no more than 1.5% of the total components in the distribution of the co-polymer are low molecular weight components having an average molecular weight of less than 4,500 Daltons;
    no more than 1.5% of the total components in the distribution of the co-polymer are high molecular weight components having an average molecular weight of greater than 13,000 Daltons;
    the polydispersity value of the copolymer is less than approximately 1.07 or less than 1.07; and
    following intravenous administration to a human subject, the circulating plasma half-life of any components not comprising the main peak in the distribution of copolymer is no more than 5.0 fold the circulating half-life of the main component in the distribution of the copolymer.

17. The method of claim 16, wherein all components in the distribution of the copolymer, when administered to a human subject, have a circulating half-life in the plasma of the subject that is no more than 12 hours, 10 hours, 9 hours, 8 hours or 7 hours.

18. The method of claim 1, wherein:
    the LCMF poloxamer 188 is a polyoxyethylene/polyoxypropylene copolymer that has the formula $HO(CH_2CH_2O)_{a'}\text{—}[CH(CH_3)CH_2O]_b\text{—}(CH_2CH_2O)_aH$;
    each of a and a' is an integer such that the percentage of the hydrophile $(C_2H_4O)$ is between approximately 60% and 90% by weight of the total molecular weight of the copolymer;
    a and a' are the same or different;

b is an integer such that the molecular weight of the hydrophobe ($C_3H_6O$) is between approximately 1,300 Daltons and 2,300 Daltons;

no more than 1.5% of the total components in the distribution of the co-polymer are low molecular weight components having an average molecular weight of less than 4,500 Daltons;

no more than 1.5% of the total components in the distribution of the co-polymer are high molecular weight components having an average molecular weight of greater than 13,000 Daltons;

the polydispersity value of the copolymer is less than approximately 1.07 or less than 1.07; and the LCMF poloxamer 188 is more hydrophilic than purified poloxamer 188 that contains the long circulating material (LCM) or compared to a standard, wherein LCM material in the poloxamer, when administered to a human subject, has more than about or more than 5-fold the half-life of the main component of the poloxamer preparation.

19. The method of claim 1, wherein:

the LCMF poloxamer 188 is a polyoxyethylene/polyoxypropylene copolymer that has the formula $HO(CH_2CH_2O)_a$—$[CH(CH_3)CH_2O]_b$—$(CH_2CH_2O)_{a'}H$;

each of a and a' is an integer such that the percentage of the hydrophile ($C_2H_4O$) is between approximately 60% and 90% by weight of the total molecular weight of the copolymer;

a and a' are the same or different;

b is an integer such that the molecular weight of the hydrophobe ($C_3H_6O$) is between approximately 1,300 Daltons and 2,300 Daltons;

no more than 1.5% of the total components in the distribution of the co-polymer are low molecular weight components having an average molecular weight of less than 4,500 Daltons;

no more than 1.5% of the total components in the distribution of the co-polymer are high molecular weight components having an average molecular weight of greater than 13,000 Daltons;

the polydispersity value of the copolymer is less than approximately 1.07 or less than 1.07; and the LCMF poloxamer 188 has a mean retention time ($t_R$) as assessed by reverse phase-high performance liquid chromatography (RP-HPLC) that is shorter than purified long circulating material (LCM)-containing poloxamer 188 under the same conditions.

20. The method of claim 1, wherein:

the LCMF poloxamer 188 is a polyoxyethylene/polyoxypropylene copolymer that has the formula $HO(CH_2CH_2O)_a$—$[CH(CH_3)CH_2O]_b$—$(CH_2CH_2O)_{a'}H$, wherein:

each of a and a' is an integer such that the percentage of the hydrophile ($C_2H_4O$) is between approximately 60% and 90% by weight of the total molecular weight of the copolymer;

a and a' are the same or different;

b is an integer such that the molecular weight of the hydrophobe ($C_3H_6O$) is between approximately 1,300 Daltons and 2,300 Daltons;

no more than 1.5% of the total components in the distribution of the co-polymer are low molecular weight components having an average molecular weight of less than 4,500 Daltons;

no more than 1.5% of the total components in the distribution of the co-polymer are high molecular weight components having an average molecular weight of greater than 13,000 Daltons;

the polydispersity value of the copolymer is less than approximately 1.07 or less than 1.07; and the capacity factor (k') of the LCMF poloxamer 188 as assessed by RP-HPLC is less than the k' for purified LCM-containing poloxamer 188 under the same conditions.

21. The method of claim 1, wherein the polyoxyethylene/polyoxypropylene copolymer is a poloxamer with a hydrophobe having a molecular weight of about 1,400 Da to 2,000 Da or 1,400 Da to 2,000 Da, and a hydrophile portion constituting approximately 70% to 90% or 70% to 90% by weight of the copolymer.

22. The method of claim 21, wherein the average molecular weight of the polyoxyethylene/polyoxypropylene copolymer is 8,400-8,800 Daltons.

23. The method of claim 1, wherein the dosage of the copolymer in each infusion that is administered is from or from about 200 mg/kg to 450 mg/kg.

24. The method of claim 1, wherein the concentration of the copolymer in the composition that is administered in each infusion is at least 10.0 mg/mL, at least 20 mg/mL, at least 30 mg/mL, at least 40 mg/mL, at least 50 mg/mL, at least 60 mg/mL, at least 70 mg/mL, at least 80 mg/mL, at least 90 mg/mL, at least 100 mg/mL, at least 115 mg/mL, at least 130 mg/mL, at least 150 mg/mL, at least 200 mg/mL or at least 225 mg/mL.

25. The method of claim 1, wherein each infusion lasts from 1 to 24 hours, or 2 to 10 hours, or 2 to 6 hours, or less than 3 hours.

26. The method of claim 1, wherein the second infusion is repeated at least 7 days, 8 days, 9 days, 10 days, 11 days, 12 days, 13 days or 14 days, 3 weeks or 4 weeks following completion of the first dose.

27. The method of claim 1, wherein the intervals between infusions are increased by at least a week.

28. The method of claim 1, wherein the second infusion is more than a week after the first infusion, the third infusion is administered at 4-5 weeks or 5-6 weeks after the second infusion.

29. The method of claim 1, wherein, for each administration, the gravimetric dose of the poloxamer copolymer is the same or different.

30. The method of claim 1, wherein the status of the condition of the subject's heart is assessed between each dose and the dose and/or timing of administration is adjusted in accord with the condition of the heart.

31. The method of claim 1, wherein the treatment is continued for more than a month or more than a year.

32. The method of claim 1, wherein the subject has acute heart failure.

33. The method of claim 1, wherein the subject has chronic heart failure.

34. The method of claim 1, wherein the subject has coronary artery disease, myocardial infarction or hypertension.

35. The method of claim 1, wherein the method comprises treatment with a second agent or treatment for treating heart failure.

36. The method of claim 33, wherein:

the second agent is selected from among a diuretic, loop diuretic, a potassium sparing agent, a vasodilator, an ACE inhibitor, ARBs (angiotensin receptor blockers), an angiotensin II antagonist, Aldosterone antagonist, a positive inotrophic agent, a phosphodiesterase inhibitor, a beta-adrenergic receptor antagonist, a calcium channel blocker, a nitrate, an alpha blocker, a central alpha antagonist, a statin, a cardiac glycoside, Digoxin, Nitrates, chlorthalidone, amlodipine, lisinopril, doxazosin, and a combination of these agents; or the second agent is a treatment provided by implantable pacemakers, defibrillators, or left ventricular assist devices (LVAD).

37. The method of claim 1, wherein a single dose of the composition contains 5 gm-50 gm of the polyoxyethylene/polyoxypropylene copolymer formulated for a single intravenous infusion of 100-675 mg/kg in a time period of 2-6 hours.

* * * * *